US012793810B2

(12) United States Patent
Parnaby et al.

(10) Patent No.: US 12,793,810 B2
(45) Date of Patent: Nov. 10, 2026

(54) TILE LOCATION AND/OR CYCLE BASED WEIGHT SET SELECTION FOR BASE CALLING

(71) Applicant: Illumina, Inc., San Diego, CA (US)

(72) Inventors: Gavin Derek Parnaby, Laguna Niguel, CA (US); Mark David Hahm, Hartland, WI (US); Andrew Christopher Du Preez, Poway, CA (US); Dorna Kashefhaghighi, Menlo Park, CA (US); Kishore Jaganathan, San Francisco, CA (US)

(73) Assignee: Illumina, Inc., San Diego, CA (US)

( * ) Notice: Subject to any disclaimer, the term of this patent is extended or adjusted under 35 U.S.C. 154(b) by 1216 days.

(21) Appl. No.: 17/687,551

(22) Filed: Mar. 4, 2022

(65) Prior Publication Data

US 2022/0301657 A1 Sep. 22, 2022

Related U.S. Application Data

(60) Provisional application No. 63/161,896, filed on Mar. 16, 2021, provisional application No. 63/161,880, filed on Mar. 16, 2021.

(51) Int. Cl.

| | |
|---|---|
| ***G16B 30/00*** | (2019.01) |
| ***G06N 3/04*** | (2023.01) |
| ***G06N 3/0464*** | (2023.01) |
| ***G06N 3/0495*** | (2023.01) |
| ***G06N 3/08*** | (2023.01) |
| ***G16B 40/00*** | (2019.01) |

(52) U.S. Cl.
CPC ............... *G16B 30/00* (2019.02); *G06N 3/04* (2013.01); *G06N 3/0464* (2023.01); *G06N 3/0495* (2023.01); *G06N 3/08* (2013.01); *G16B 40/00* (2019.02)

(58) Field of Classification Search
CPC ........ G16B 30/00; G16B 40/00; G16B 40/20; G06N 3/04; G06N 3/0464; G06N 3/0495; G06N 3/08; G06N 3/09; G06N 3/048; G06N 3/063
See application file for complete search history.

(56) References Cited

U.S. PATENT DOCUMENTS

| | | | |
|---|---|---|---|
| 5,302,509 | A | 4/1994 | Cheeseman |
| 5,502,773 | A | 3/1996 | Tibbetts et al. |
| 5,641,658 | A | 6/1997 | Adams et al. |
| 6,090,592 | A | 7/2000 | Adams et al. |
| 7,057,026 | B2 | 6/2006 | Barnes et al. |
| 7,115,400 | B1 | 10/2006 | Adessi et al. |
| 7,133,782 | B2 | 11/2006 | Odedra |
| 7,209,836 | B1 | 4/2007 | Schermer et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,427,673 | B2 | 9/2008 | Balasubramanian et al. |
| 7,541,444 | B2 | 6/2009 | Milton et al. |
| 7,566,537 | B2 | 7/2009 | Balasubramanian et al. |
| 7,592,435 | B2 | 9/2009 | Milton et al. |
| 8,149,464 | B2 | 4/2012 | Kim |
| 8,182,993 | B2 | 5/2012 | Tomaney et al. |
| 8,241,573 | B2 | 8/2012 | Banerjee et al. |
| 8,392,126 | B2 | 3/2013 | Mann |
| 8,401,258 | B2 | 3/2013 | Hargrove et al. |
| 8,407,012 | B2 | 3/2013 | Erlich et al. |
| 8,594,439 | B2 | 11/2013 | Staelin et al. |
| 8,612,161 | B2 | 12/2013 | Gordon et al. |
| 8,703,422 | B2 | 4/2014 | Tomaney et al. |
| 8,725,425 | B2 | 5/2014 | Heiner et al. |
| 8,795,971 | B2 | 8/2014 | Kersey et al. |
| 8,965,076 | B2 | 2/2015 | Garcia et al. |

(Continued)

FOREIGN PATENT DOCUMENTS

| | | |
|---|---|---|
| CA | 2894317 A1 | 12/2016 |
| CA | 3065927 A1 | 7/2019 |

(Continued)

OTHER PUBLICATIONS

Ramesh, Nisha, et. al., “Cell Segmentation Using a Similarity Interface With a Multi-Task Convolutional Neural Network”; IEEE Journal of Biomedical and Health Informatics, vol. 23, No. 4, Jul. 2019, 12 pages.
Arpali et. al., High-throughput screening of large volumes of whole blood using structured illumination and fluoresecent on-chip imaging, Lab on a Chip, United Kingdom, Royal Society of Chemistry, Sep. 12, 2012, vol. 12, pp. 4968-4971.
Liu et. al., 3D Stacked Many Core Architecture for Biological Sequence Analysis Problems, 2017, Int J Parallel Prog, 45:1420-1460.
Wu et. al., FPGA-Based DNA Basecalling Hardware Acceleration, in Proc. IEEE 61st Int. Midwest Symp. Circuits Syst., Aug. 2018, pp. 1098-1101.
Wu et. al., FPGA-Accelerated 3rd Generation DNA Sequencing, in IEEE Transactions on Biomedical Circuits and Systems, vol. 14, Issue 1, Feb. 2020, pp. 65-74.

(Continued)

*Primary Examiner* — Janna Nicole Schultzhaus
(74) *Attorney, Agent, or Firm* — Keller Preece PLLC

(57) ABSTRACT

A system for base calling includes memory storing a topology of a neural network, a plurality of weights sets, and sensor data for a series of sensing cycles. Sequencing events span temporal progression of the base calling operation through subseries of sensing cycles, and spatial progression of the base calling operation through locations on a biosensor. A configurable processor is configured to load the topology on the configurable processor, select a weight set in dependence upon a subject subseries of sensing cycles and/or a subject location on the biosensor, load subject sensor data for the subject subseries of sensing cycles and the subject location on the processing elements, configure the topology using the selected weight set, and cause the neural network to process the subject sensor data to produce base call classification data for the subject subseries and the subject location.

29 Claims, 31 Drawing Sheets

(56) References Cited

U.S. PATENT DOCUMENTS 9,175,343 B2 11/2015 Tomaney et al.
9,279,154 B2 3/2016 Previte et al.
9,453,258 B2 9/2016 Kain et al.
9,708,656 B2 7/2017 Turner et al.
10,023,911 B2 7/2018 Tomaney et al.
10,068,053 B2 9/2018 Kermani et al.
10,068,054 B2 9/2018 Van Rooyen et al.
10,152,776 B2 12/2018 Langlois et al.
10,168,438 B2 1/2019 Dennis et al.
10,241,075 B2 3/2019 Davey et al.
10,354,747 B1 7/2019 DePristo et al.
10,378,053 B2 8/2019 Staker et al.
10,423,861 B2 9/2019 Gao et al.
10,491,239 B1 11/2019 Hubara
10,527,549 B2 1/2020 Rebetez et al.
10,540,591 B2 1/2020 Gao et al.
10,619,195 B2 4/2020 Lamb et al.
10,648,027 B2 5/2020 Mannion et al.
10,711,299 B2 7/2020 Rothberg et al.
10,713,794 B1 7/2020 He et al.
10,740,880 B2 8/2020 Paik et al.
10,740,883 B2 8/2020 Zerfass et al.
10,755,810 B2 8/2020 Buckler et al.
10,943,255 B1 3/2021 Andreou
10,963,673 B2 3/2021 Schaumberg et al.
11,056,220 B2 7/2021 Lyman et al.
11,107,554 B2 8/2021 Pratt et al.
11,138,496 B2 10/2021 Seth
11,210,554 B2 12/2021 Dutta et al.
11,263,450 B2 3/2022 Bandyopadhyay et al.
11,276,480 B2 3/2022 Pratt et al.
11,347,965 B2 5/2022 Dutta et al.
11,436,429 B2 9/2022 Jaganathan et al.
11,462,300 B2 10/2022 Bartov et al.
11,538,556 B2 12/2022 Rothberg et al.
11,783,917 B2 10/2023 Jaganathan et al.
11,972,583 B2 4/2024 Shen et al.
12,211,589 B2 1/2025 Li et al.
12,385,899 B2 8/2025 Stoiber et al.
2002/0055100 A1 5/2002 Kawashima et al.
2002/0147548 A1 10/2002 Walther et al.
2003/0062485 A1 4/2003 Fernandez et al.
2003/0087289 A1 5/2003 Zuzan et al.
2003/0120471 A1 6/2003 Izmailov et al.
2004/0002090 A1 1/2004 Mayer et al.
2004/0062360 A1 4/2004 Holeva
2004/0096853 A1 5/2004 Mayer
2005/0032076 A1 2/2005 Williams et al.
2006/0014151 A1 1/2006 Ogura et al.
2006/0040297 A1 2/2006 Leamon et al.
2006/0064248 A1 3/2006 Saidi et al.
2006/0188901 A1 8/2006 Barnes et al.
2006/0224529 A1 10/2006 Kermani
2006/0240439 A1 10/2006 Smith et al.
2006/0269130 A1 11/2006 Maroy et al.
2007/0118490 A1 5/2007 Soderman et al.
2007/0128624 A1 6/2007 Gormley et al.
2007/0166705 A1 7/2007 Milton et al.
2007/0177799 A1 8/2007 Tyurina
2007/0250274 A1 10/2007 Volkov et al.
2008/0009420 A1 1/2008 Schroth et al.
2008/0181296 A1 7/2008 Tian et al.
2008/0234136 A1 9/2008 Drmanac et al.
2008/0242560 A1 10/2008 Gunderson et al.
2009/0024331 A1 1/2009 Tomaney et al.
2009/0081775 A1 3/2009 Hodneland et al.
2010/0034444 A1 2/2010 Emhoff et al.
2010/0046830 A1 2/2010 Wang et al.
2010/0088255 A1 4/2010 Mann
2010/0111370 A1 5/2010 Black et al.
2010/0157086 A1 6/2010 Segale et al.
2011/0007981 A1 1/2011 Osher et al.
2011/0059865 A1 3/2011 Smith et al.
2011/0065607 A1 3/2011 Kersey et al.
2011/0144991 A1 6/2011 Fousek et al.
2011/0281736 A1 11/2011 Drmanac et al.
2011/0286628 A1 11/2011 Goncalves et al.
2011/0295902 A1 12/2011 Mande et al.
2012/0015825 A1 1/2012 Zhong et al.
2012/0020537 A1 1/2012 Garcia et al.
2013/0059740 A1 3/2013 Drmanac et al.
2013/0079232 A1 3/2013 Kain et al.
2013/0090860 A1 4/2013 Sikora et al.
2013/0124100 A1 5/2013 Drmanac et al.
2013/0137091 A1 5/2013 Gordon et al.
2013/0188866 A1 7/2013 Obrador et al.
2013/0250407 A1 9/2013 Schaffer et al.
2014/0051588 A9 2/2014 Drmanac et al.
2014/0152801 A1 6/2014 Fine et al.
2014/0228223 A1 8/2014 Gnirke et al.
2015/0079596 A1 3/2015 Eltoukhy et al.
2015/0117784 A1 4/2015 Lin et al.
2015/0169824 A1 6/2015 Kermani et al.
2016/0042511 A1 2/2016 Chukka et al.
2016/0078272 A1 3/2016 Hammoud
2016/0102348 A1 4/2016 Donnet
2016/0110498 A1 4/2016 Bruand et al.
2016/0196479 A1 7/2016 Chertok et al.
2016/0247034 A1 8/2016 Lee et al.
2016/0350914 A1 12/2016 Champlin et al.
2016/0356715 A1 12/2016 Zhong et al.
2016/0357903 A1 12/2016 Shendure et al.
2016/0371431 A1 12/2016 Haque et al.
2017/0044601 A1 2/2017 Crnogorac et al.
2017/0098032 A1 4/2017 Desai et al.
2017/0116520 A1 4/2017 Min et al.
2017/0161545 A1 6/2017 Champlin et al.
2017/0169313 A1 6/2017 Choi et al.
2017/0228496 A1 8/2017 Boutros et al.
2017/0249421 A1 8/2017 Eberle et al.
2017/0249744 A1 8/2017 Wang et al.
2017/0362634 A1 12/2017 Ota et al.
2018/0075279 A1 3/2018 Gertych et al.
2018/0101951 A1 4/2018 Xu et al.
2018/0107926 A1 4/2018 Choi et al.
2018/0107927 A1 4/2018 Frey
2018/0114337 A1 4/2018 Li et al.
2018/0165412 A1 6/2018 Frey et al.
2018/0189613 A1 7/2018 Wolf et al.
2018/0195953 A1 7/2018 Langlois et al.
2018/0197081 A1 7/2018 Ji et al.
2018/0201992 A1 7/2018 Wu et al.
2018/0204048 A1 7/2018 Chefd'Hotel et al.
2018/0211001 A1 7/2018 Gopalan et al.
2018/0253528 A1 9/2018 Strauss et al.
2018/0274023 A1 9/2018 Belitz et al.
2018/0276333 A1 9/2018 Njie et al.
2018/0286040 A1 10/2018 Sashida
2018/0305751 A1 10/2018 Vermaas et al.
2018/0322327 A1 11/2018 Smith et al.
2018/0330824 A1 11/2018 Athey
2018/0334711 A1 11/2018 Kelley et al.
2018/0334712 A1 11/2018 Singer et al.
2018/0340234 A1 11/2018 Scafe et al.
2019/0034586 A1 1/2019 Pirrotte et al.
2019/0080450 A1 3/2019 Arar et al.
2019/0107642 A1 4/2019 Farhadi Nia et al.
2019/0114464 A1 4/2019 Nicolle et al.
2019/0114544 A1 4/2019 Sundaram et al.
2019/0128869 A1 5/2019 Chou et al.
2019/0156915 A1 5/2019 Zhang et al.
2019/0164010 A1 5/2019 Ma et al.
2019/0170680 A1 6/2019 Sikora et al.
2019/0180153 A1 6/2019 Buckler et al.
2019/0213473 A1 7/2019 Dutta et al.
2019/0237160 A1 8/2019 Rothberg et al.
2019/0237163 A1 8/2019 Wang et al.
2019/0244348 A1 8/2019 Buckler et al.
2019/0252041 A1 8/2019 Frey et al.
2019/0266491 A1 8/2019 Gao et al.
2019/0272638 A1 9/2019 Mouton et al.
2019/0318806 A1 10/2019 Wise et al.
2019/0332118 A1 10/2019 Wang et al.
2019/0340492 A1 11/2019 Burger et al.

(56) References Cited

U.S. PATENT DOCUMENTS

| | | | |
|---|---|---|---|
| 2019/0378248 | A1 | 12/2019 | Ida et al. |
| 2019/0385699 | A1 | 12/2019 | Garcia et al. |
| 2019/0392578 | A1 | 12/2019 | Chukka et al. |
| 2020/0027002 | A1 | 1/2020 | Hickson et al. |
| 2020/0054306 | A1 | 2/2020 | Mehanian et al. |
| 2020/0057838 | A1 | 2/2020 | Yekhanin et al. |
| 2020/0065675 | A1 | 2/2020 | Sundaram et al. |
| 2020/0097701 | A1 | 3/2020 | Chukka et al. |
| 2020/0123552 | A1 | 4/2020 | Lee et al. |
| 2020/0125947 | A1 | 4/2020 | Park et al. |
| 2020/0176082 | A1 | 6/2020 | Massingham |
| 2020/0185055 | A1 | 6/2020 | Debourg-Felonneau et al. |
| 2020/0193597 | A1 | 6/2020 | Fan et al. |
| 2020/0224243 | A1 | 7/2020 | Desai et al. |
| 2020/0226368 | A1 | 7/2020 | Bakalo et al. |
| 2020/0256856 | A1 | 8/2020 | Chou et al. |
| 2020/0272881 | A1 | 8/2020 | Lo |
| 2020/0285933 | A1 | 9/2020 | Zhang |
| 2020/0302223 | A1 | 9/2020 | Dutta et al. |
| 2020/0302224 | A1 | 9/2020 | Jaganathan et al. |
| 2020/0302276 | A1 | 9/2020 | Yang et al. |
| 2020/0302283 | A1 | 9/2020 | Zhu et al. |
| 2020/0302297 | A1 | 9/2020 | Jaganathan et al. |
| 2020/0302603 | A1 | 9/2020 | Barnes et al. |
| 2020/0320294 | A1 | 10/2020 | Mangal et al. |
| 2020/0327377 | A1 | 10/2020 | Jaganathan et al. |
| 2020/0342955 | A1 | 10/2020 | Guo et al. |
| 2020/0364565 | A1 | 11/2020 | Kostem |
| 2020/0388029 | A1 | 12/2020 | Saltz et al. |
| 2021/0019630 | A1 | 1/2021 | Yao et al. |
| 2021/0020314 | A1 | 1/2021 | Ehrich et al. |
| 2021/0027462 | A1 | 1/2021 | Bredno et al. |
| 2021/0056287 | A1 | 2/2021 | Schaumburg et al. |
| 2021/0064954 | A1 | 3/2021 | Choi et al. |
| 2021/0072391 | A1 | 3/2021 | Li et al. |
| 2021/0089827 | A1 | 3/2021 | Kumagai et al. |
| 2021/0115490 | A1 | 4/2021 | Embree et al. |
| 2021/0174172 | A1 | 6/2021 | Qadeer et al. |
| 2021/0183053 | A1 | 6/2021 | Zink et al. |
| 2021/0217171 | A1 | 7/2021 | Li et al. |
| 2021/0224658 | A1 | 7/2021 | Mathew et al. |
| 2021/0257050 | A1 | 8/2021 | Lam et al. |
| 2021/0264266 | A1 | 8/2021 | Dutta et al. |
| 2021/0264267 | A1 | 8/2021 | Dutta et al. |
| 2021/0265009 | A1 | 8/2021 | Jaganathan et al. |
| 2021/0265015 | A1 | 8/2021 | Parnaby et al. |
| 2021/0265016 | A1 | 8/2021 | Vessere et al. |
| 2021/0265017 | A1 | 8/2021 | Dutta et al. |
| 2021/0265018 | A1 | 8/2021 | Dutta et al. |
| 2021/0279635 | A1 | 9/2021 | GadelRab et al. |
| 2021/0324374 | A1 | 10/2021 | Feagin et al. |
| 2021/0366576 | A1* | 11/2021 | Bartov ................. G06N 3/0455 |
| 2021/0390278 | A1 | 12/2021 | Van Leeuwen et al. |
| 2022/0067489 | A1 | 3/2022 | Kashefhaghighi et al. |
| 2022/0067497 | A1 | 3/2022 | Dikici et al. |
| 2022/0075669 | A1 | 3/2022 | Shomron et al. |
| 2022/0101133 | A1 | 3/2022 | Ardywibowo et al. |
| 2022/0114479 | A1 | 4/2022 | Zhao et al. |
| 2022/0121884 | A1 | 4/2022 | Zadeh et al. |
| 2022/0129759 | A1 | 4/2022 | Yao et al. |
| 2022/0147760 | A1 | 5/2022 | Dutta et al. |
| 2023/0048206 | A1 | 2/2023 | Athreya et al. |
| 2023/0154208 | A1 | 5/2023 | Desroziers et al. |
| 2025/0226056 | A1 | 7/2025 | Wise et al. |

FOREIGN PATENT DOCUMENTS

| | | | |
|---|---|---|---|
| CA | 3104851 | A1 | 11/2020 |
| CN | 102676657 | B | 1/2015 |
| CN | 105899658 | A | 8/2016 |
| CN | 105980578 | A | 9/2016 |
| CN | 105989248 | A | 10/2016 |
| CN | 107679618 | A | 2/2018 |
| CN | 108203847 | A | 6/2018 |
| CN | 108319817 | A | 7/2018 |
| CN | 106770114 | A | 3/2019 |
| CN | 109416928 | A | 3/2019 |
| CN | 110245685 | A | 9/2019 |
| CN | 110880038 | A | 3/2020 |
| CN | 112418391 | A | 2/2021 |
| CN | 113166804 | A | 7/2021 |
| EP | 3130681 | A1 | 2/2017 |
| EP | 3373238 | A1 | 9/2018 |
| JP | 2007199397 | A | 8/2007 |
| JP | 2018-173943 | A | 11/2018 |
| JP | 2019-537157 | A | 12/2019 |
| JP | 2022-524562 | A | 5/2022 |
| NL | 2023310 | A | 9/2020 |
| NL | 2023311 | A | 9/2020 |
| NL | 2023312 | A | 9/2020 |
| NL | 2023314 | A | 9/2020 |
| NL | 2023316 | A | 9/2020 |
| RU | 2580425 | C1 | 4/2016 |
| RU | 2750706 | C2 | 7/2021 |
| SG | 10201913208 | | 2/2020 |
| WO | 9106678 | A1 | 5/1991 |
| WO | 9727317 | A1 | 7/1997 |
| WO | 2004018497 | A2 | 3/2004 |
| WO | 2005065814 | A1 | 7/2005 |
| WO | 2006064199 | A1 | 6/2006 |
| WO | 2007010251 | A2 | 1/2007 |
| WO | 2007/098049 | A2 | 8/2007 |
| WO | 2007123744 | A2 | 11/2007 |
| WO | 2008/097455 | A1 | 8/2008 |
| WO | 2008154317 | A1 | 12/2008 |
| WO | 2012058096 | A1 | 5/2012 |
| WO | 2014142921 | A1 | 9/2014 |
| WO | 2015084985 | A2 | 6/2015 |
| WO | 2016145516 | A1 | 9/2016 |
| WO | 2016201564 | A1 | 12/2016 |
| WO | 2017184997 | A1 | 10/2017 |
| WO | 2018-068014 | A1 | 4/2018 |
| WO | 2018/068600 | A1 | 4/2018 |
| WO | 2018-102748 | A1 | 7/2018 |
| WO | 2018129314 | A1 | 7/2018 |
| WO | 2018/175779 | A1 | 9/2018 |
| WO | 2018165099 | A1 | 9/2018 |
| WO | 2018203084 | A1 | 11/2018 |
| WO | 2018/236827 | A1 | 12/2018 |
| WO | 2018/236911 | A1 | 12/2018 |
| WO | 2019-036388 | A1 | 2/2019 |
| WO | 2019027767 | A1 | 2/2019 |
| WO | 2019028047 | A1 | 2/2019 |
| WO | 2019055856 | A1 | 3/2019 |
| WO | 2019079182 | A1 | 4/2019 |
| WO | 2019079202 | A1 | 4/2019 |
| WO | 2019-084515 | A1 | 5/2019 |
| WO | 2019090251 | A2 | 5/2019 |
| WO | 2019136284 | A1 | 7/2019 |
| WO | 2019136388 | A1 | 7/2019 |
| WO | 2019140402 | A1 | 7/2019 |
| WO | 2019147904 | A1 | 8/2019 |
| WO | 2020014280 | A1 | 1/2020 |
| WO | 2020/037571 | A1 | 2/2020 |
| WO | 2020/037574 | A1 | 2/2020 |
| WO | 2020123552 | A1 | 6/2020 |
| WO | 2020/185790 | A1 | 9/2020 |
| WO | 2020-191387 | A1 | 9/2020 |
| WO | 2020-191389 | A1 | 9/2020 |
| WO | 2020-191391 | A1 | 9/2020 |
| WO | 2020-205296 | A1 | 10/2020 |
| WO | 2020-232409 | A1 | 11/2020 |
| WO | 2020-232410 | A1 | 11/2020 |
| WO | 2020-243185 | A1 | 12/2020 |
| WO | 2022-056296 | A1 | 3/2022 |

OTHER PUBLICATIONS

Prabhakar et. al., Plasticine: A Reconfigurable Architecture for Parallel Patterns, ISCA '17, Jun. 24-28, 2017, Toronto, ON, Canada.
Lin et. al., Network in Network, in Proc. of ICLR, 2014.
Sifre, Rigid-motion Scattering for Image Classification, Ph.D. thesis, 2014.

(56) References Cited

OTHER PUBLICATIONS

Sifre et. al., Rotation, Scaling and Deformation Invariant Scattering for Texture Discrimination, in Proc. of CVPR, 2013.
Chollet, Xception: Deep Learning with Depthwise Separable Convolutions, in Proc. of CVPR, 2017. 8 pages.
Zhang et. al., ShuffleNet: An Extremely Efficient Convolutional Neural Network for Mobile Devices, 2017.
He et. al., Deep Residual Learning for Image Recognition, in Proc. of CVPR, 2016.
Xie et. al., Aggregated Residual Transformations for Deep Neural Networks, in Proc. of CVPR, 2017.
Howard et. al., Mobilenets: Efficient Convolutional Neural Networks for Mobile Vision Applications, 2017.
Sandler et. al., MobileNetV2: Inverted Residuals and Linear Bottlenecks, 2018.
Qin et. al., FD-MobileNet: Improved MobileNet with a Fast Downsampling Strategy, 2018.
Chen et. al., Rethinking atrous convolution for semantic image segmentation, 2017.
Huang et. al., Speed/accuracy trade-offs for modern convolutional detectors, 2016.
Oord et al., Wavenet: A Generative Model for Raw Audio, dated Sep. 19, 2016, 15 pages.
Arik et al., Deep Voice: Real-time Neural Text-to-Speech, dated 2017, 17 pages.
Yu et al., Multi-Scale Context Aggregation by Dilated Convolutions, ICLR 2016, dated Apr. 30, 2016, 13 pages.
He et. al., Deep Residual Learning for Image Recognition, 2015.
Srivastava et al., Highway Networks, dated 2015, 6 pages.
Huang et al., Densely Connected Convolutional Networks, dated Aug. 17, 2017, 9 pages.
Szegedy et. al., Going Deeper with Convolutions, dated 2014, 12 pages.
Ioffe et al., Batch Normalization Accelerating Deep Network Training by Reducing Internal Covariate Shift, dated 2015, 11 pages.
Wolterink et al., Dilated Convolutional Neural Networks for Cardiovascular MR Segmentation in Congenital Heart Disease, dated 2017, 9 pages.
Piqueras, Autoregressive Model Based on a Deep Convolutional Neural Network for Audio Generation, Tampere University of Technology, dated 2016, 58 pages.
Wu, Introduction to Convolutional Neural Networks, Nanjing University, dated 2017, 31 pages.
scikit-image/peak.py at master, Github, retrieved on Jun. 8, 2021, 10 pages, Retrieved from the internet <URL: https://github.com/scikit-image/scikit-image/blob/main/skimage/feature/peak.py>.
3.3.9.11.Watershed and random walker for segmentation, Scipy lecture notes, 2 pages. [retrieved on Jun. 8, 2021] Retrieved from the internet <URL: http:scipy-lectures.org/packages/scikit-image/auto_examples/plot_segmentations.html>.
Mordvintsev et. al., Image Segmentation with Watershed Algorithm, Revision 43532856, 2013, 6 pages. [retrieved on Jun. 8, 2021] Retrieved from the Internet <URL: https://opencv-python-tutroals.readthedocs.io/en/latest/py_tutorials/by_imgproc/py_watershed/py_watershed.html>.
Mzur, Watershed.py, Github, 3 pages. [retrieved on Jun. 8, 2021] Retrieved from the internet <URL: https://github.com/mzur/watershed/blob/master/Watershed.py>.
Thakur et. al., A Survey of Image Segmentation Techniques, International Journal of Research in Computer Applications and Robotics, vol. 2, Issue 4, Apr. 2014, p. 158-165.
Long et. al., Fully Convolutional Networks for Semantic Segmentation, IEEE Transactions on Pattern Analysis and Machine Intelligence, vol. 39, Issue 4, Apr. 1, 2017, 12 pages.
Ronneberger et. al., U-net: Convolutional networks for biomedical image segmentation, in International Conference on Medical Image computing and computer assisted intervention, May 18, 2015, 8 pages.
Xie et. al., Microscopy cell counting and detection with fully convolutional regression networks, Computer methods in biomechanics and biomedical engineering, Imaging and Visualization, 6(3), pp. 283-292, 2018.
Xie, Y., et. al., Beyond classification: structured regression for robust cell detection using convolutional neural network, International conference on medical image computing and computer assisted intervention, Oct. 2015, 12 pages.
Snuverink, Deep Learning for Pixelwise Classification of Hyperspectral Images, Master of Science Thesis, Delft University of Technology, Nov. 23, 2017, 128 pages.
Shevchenko, Keras weighted categorical_crossentropy, Github, [retrieved on Jun. 12, 2021], Retrieved from the internet <URL: https://gist.github.com/skeeet/cad06d584548fb45eece1d4e28cfa98b >, 2 pages.
Assem, Predicting periodic and chaotic signals using Wavenets, Master of Science thesis, Delft University of Technology, Aug. 18, 2017, pp. 3-38.
Goodfellow et al., Chapter 9—Convolutional Networks, Deep Learning, MIT Press, dated 2016, 41 pages.
Illumina, "Indexed Sequencing Overview Guide", Document No. 15057455, v. 5, Mar. 2019.
Albrecht et. al., Deep learning for single-molecule science, Nanotechnology (28), dated 2017, 423001, 11 pages.
MiSEQ: Imaging and Base Calling: Illumina, Inc. Online Training Course, dated Jan. 1, 2013 [retrieved on Jul. 13, 2020], Retrieved from <URL: https://support.illumina.com/training.html >, 13 pages.
MiSEQ: Imaging and Base Calling Script, retrieved on [Jun. 14, 2021], Retrieved from the internet <URL: https://support.illumina.com/content/dam/illumina-support/courses/MiSeq_Imaging_and_Base_Calling/story_content/external_files/MiSeq%20Imaging%20and%20Base%20Calling%20Script.pdf >.
Zhao et. al., Object detection with Deep Learning: A Review, dated Jul. 15, 2018, 22 pages.
Lee et. al., Fast Object Localization Using a CNN Feature Map Based Multi-Scale Search, dated Apr. 12, 2016, 16 pages.
Misiunas et. al., QuipuNet: convolutional neural network for single-molecule nanopore sensing, dated May 30, 2018, 7 pages.
Boza et. al., Deep Recurrent Neural Networks for Base Calling in MinION Nanopore Reads, dated Mar. 30, 2016, 12 pages.
Kao et. al., BayesCall: A model-based base-calling algorithm for high-throughput short-read sequencing, Genome Research (19), pp. 1884-1895, dated 2009.
Rang et. al., From squiggle to basepair: computational approaches for improving nanopore sequencing read accuracy, Genome Biology 2018, (19), 30.
Wang et. al., An adaptive decorrelation method removes Illumina DNA base-calling errors caused by crosstalk between adjacent clusters, Scientific Reports, published Feb. 20, 2017, 11 pages.
Cacho et. al., A comparison of Base Calling Algorithms for Illumina Sequencing Technology, dated Oct. 5, 2015, Briefings in Bioinformatics 2016 (17), 786-795.
Luo et. al., G-softmax: Improving Intra-class Compactness and Inter-class Separability of Features, dated Apr. 8, 2019, 15 pages.
Luo et. al., A multi-task convolutional deep neural network for variant calling in single molecule sequencing, Nature Communications (10), No. 1, dated Mar. 1, 2019.
Kingma et. al., Adam: A method for Stochastic Optimization, ICLR 2015, dated Jul. 23, 2015.
Luo et. al., Skyhawk: An Artificial Neural Network-based discriminator for reviewing clinically significant genomic variants, dated Jan. 28, 2019, 8 pages.
MiSEQ: Imaging and Base Calling: Illumina, Inc. Online Training Course, colored version, [retrieved on Oct. 11, 2020], Retrieved from <URL: https://support.illumina.com/training.html >, 9 pages.
Kircher et. al., Improved base-calling for the Illumina Genome Analyzer using Machine Learning Strategies, Genome Biology, published Aug. 14, 2009, 9 pages.
Angermueller, Christof, et. al., Deep learning for computational biology, Molecular Systems Biology, dated Jun. 6, 2016, 16 pages.
Smith et. al., Barcoding and demultiplexing Oxford nanopore native RNA sequencing reads with deep residual learning, bioRxiv, dated Dec. 5, 2019, 18 pages.

(56) References Cited

OTHER PUBLICATIONS

Aggarwal, Neural Networks and Deep Learning: A Textbook, Springer, dated Aug. 26, 2018, 512 pages.
Wang et. al., Deep Neural Network Approximation for Custom Hardware: Where We've Been, Where We're Going, Cornell University, dated Jan. 21, 2019, 37 pages.
Lavin et. al., Fast Algorithms for Convolutional Neural Networks, dated Nov. 10, 2015, 9 pages.
Liu et. al., A Uniform Architecture Design for Accelerating 2D and 3D CNNs on FPGAs, published Jan. 7, 2019, 19 pages.
Zeng et. al., Causalcall: Nanopore Basecalling Using a Temporal Convolutional Network, dated Jan. 20, 2020, 11 pages.
Kwon et. al., Understanding Reuse, Performance, and Hardware Cost of DNN Dataflow—A Data-Centric Approach, Proceedings of the 52nd Annual IEEE/ACM International Symposium on Microarchitecture, dated Oct. 12, 2019, 13 pages.
Sze et. al., Efficient Processing of Deep Neural Networks: A Tutorial and Survey, Cornell University Library, dated Mar. 27, 2017, 21 pages.
Sundaram, L. et. al., "Predicitng the clinical impact of human mutation with deep neural networks", Nat. Genet. 50, 1161-1170 (2018).
Jaganathan, K. et. al., "Predicting splicing from primary sequence with deep learning", Cell 176, 535-548, (2019).
Kircher, Martin, et al. "A general framework for estimating the relative pathogenicity of human genetic variants." Nature genetics 46.3 (2014): 310. (Year:2014).
Henikoff, S. & Henikoff, J. G. Amino acid substitution matrices from protein blocks. Proc. Natl. Acad. Sci. USA 89, 10915-10919 (1992).
Li, W. H., Wu, C. I. & Luo, C. C. Nonrandomness of point mutation as reflected in nucleotide substitutions in pseudogenes and its evolutionary implications. J. Molec. Evol. 21, 58-71 (1984).
Grantham, R. Amino acid difference formula to help explain protein evolution. Science 185, 862-864 (1974).
LeCun, Y., Botlou, L., Bengio, Y., & Haffner, P. Gradient based learning applied to document recognition. Proc. IEEE 86, 2278-2324 (1998).
Vissers, L. E., Gilissen, C., & Veltman, J. A. Genetic studies in intellectual disability and related disorders. Nat. Rev. Genet. 17, 9-18 (2016).
Neale, B. M. et al. Patterns and rates of exonic de novo mutations in autism spectrum disorders. Nature 485, 242-245 (2012).
Sanders, S. J. et al. De novo mutations revealed by whole-exome sequencing are strongly associated with autism. Nature 485, 237-241 (2012).
De Rubeis, S. et al. Synaptic, transcriptional and chromatin genes disrupted in autism. Nature 515, 209-215 (2014).
Deciphering Developmental Disorders Study. Large-scale discovery of novel genetic causes of developmental disorders. Nature 519, 223-228 (2015).
Deciphering Developmental Disorders Study. Prevalence and architecture of de novo mutations in developmental disorders. Nature 542, 433-438 (2017).
Iossifov, I. et al. The contribution of de novo coding mutations to autism spectrum disorder. Nature 515, 216-221 (2014).
Zhu, X. Need, A. C., Petrovski, S. & Goldstein, D. B. One gene, many neuropsychiatric disorders: lessons from Mendelian diseases. Nat. Neurosci. 17, 773-781, (2014).
Leffler, E. M. et al. Revisiting an old riddle: what determines genetic diversity levels within species? PLoS Biol. 10, e1001388 (2012), 9pages.
Estrada, A. et al. Impending extinction crisis of the world's primates—why primates matter. Sc. Adv. 3, e1600946 (2017), 17 pages.
Kent, W. J. et al. The human genome browser at UCSC. Genome Res. 12, 996-1006 (2002).
Tyner, C. et al. The UCSC Genome Browser database—2017 update. Nucleic Acids Res. 45, D626-D634 (2017).
Kabsch, W., & Sander, C. Dictionary of protein secondary structure—pattern recognition of hydrogen-bonded and geometrical features. Biopolymers 22, 2577-2637 (1983).
Joosten, R. P. et al. A series of PDB related databases for everyday needs. Nucleic Acids Res. 39, 411-419 (2011).
He, K, Zhang, X., Ren, S., & Sun, J. Identity mappings in deep residual networks. in 14th European Conference on Computer Vision—ECCV 2016. ECCV 2016. Lecture Notes in Computer Science, vol. 9908; 630 6,15 (Springer, Cham, Switzerland; 2016).
Ionita-Laza, I., McCallum, K., Xu, B., & Buxbaum, J. D. A spectral approach integrating functional genomic annotations for coding and noncoding variants. Nat. Genet. 48, 214-220 (2016).
Li, B. et al. Automated inference of molecular mechanisms of disease from amino acid substitutions. Bioinformatics 25, 2744-2750 (2009).
Lu, Q. et al. A statistical framework to predict functional non-coding regions in the human genome through integrated analysis of annotation data. Sci. Rep. 5, 10576 (2015), 13pgs.
Shihab, H. A. et al. Predicting the functional, molecular, and phenotypic consequences of amino acid substitutions using hidden Markov models. Human. Mutat. 34, 57-65 (2013).
Davydov, E. V. et al. Identifying a high fraction of the human genome to be under selective constraint using GERP++. Plos Comput. Biol. 6, Dec. 2, 2010, 13 pages.
Liu, X., Wu, C., Li, C., & Boerwinkle, E. dbNSFPv3.0 a one-stop database of functional predictions and annotations for human nonsynonymous and splice-site SNVs. Human. Mutat. 37, 235-241 (2016).
Jain, S., White, M., Radivojac, P. Recovering true classifier performance in positive-unlabeled learning. in Proceedings Thirty-First AAAI Conference on Artificial Intelligence. 2066-2072 (AAAI Press, San Francisco; 2017).
De Ligt, J. et al. Diagnostic exome sequencing in persons with severe intellectual disability. N. Engl. J. Med. 367, 1921-1929 (2012).
Iossifov, I. et al. De novo gene disruptions in children on the autistic spectrum. Neuron 74, 285-299 (2012).
Eraslan et. al., "Deep Learning: New computational modelling techniques for genomics", dated Jul. 2019, 15 pages.
Semantic Segmentation Examples—MATLAB and Simulink, 22 pages, [retrieved on Jul. 21, 2021], Retrieved from the Internet [URL: https://www.mathworks.com/help/vision/ug/semantic-segmentation-examples.html ].
Bentley et. al., Accurate Whole Human Genome Sequencing using Reversible Terminator Chemistry, Supplemental Information, Nature, dated Nov. 6, 2008, 55 pages, [retrieved on Jul. 21, 2021], retrieved from the internet [URL: https://media.nature.com/original/nature-assets/nature/journal/v456/n7218/extref/nature07517-s1.pdf ].
Grange, NGS: the basics, Institut Jacques Monod, dated Jun. 26, 2000, 59 pages.
Massingham et. al., All Your Base: a fast and accurate probabilistic approach to base calling, European Bioinformatics Institute, 22 pages, [retrieved on Jul. 22, 2021], Retrieved from the internet [URL: https://www.ebi.ac.uk/goldman-srv/AYB/references/ayb.pdf].
Krishnakumar et. al., Systematic and stochastic influences on the performance of the MinION nanopore sequencer across a range of nucleotide bias, Scientific Reports, published Feb. 16, 2018, 13 pages.
Tegfalk, Application of Machine Learning techniques to perform base-calling in next-generation DNA sequencing, KTH Royal Institue of Technology, dated 2020, 53 pages.
Kircher-etal_Improved-base-calling-for-the-Illumina-Genome-Analyzer-using-machine-learning-strategies_14August2009_10pages.
Kircher et al, Improved base-calling for the IIllumina Genome Analyzer using Machine Learning Strategies, Genome Biology 2009, I O:R83, Aug. 14, 2009, 10 pages.
Albrecht etal, "Deep Learning for single-molecule science", Nanotechnology 28, IOP Publishuigm Sep. 18, 2017 11 pages.
Adriana Romero et. al., FitNets: Hints for Thin Deep Nets, published Mar. 27, 2015, 13 pages.

(56) References Cited

OTHER PUBLICATIONS

Robinson et al., Computational Exome and Genome Analysis—Chapter 3 Illumina Technology, dated 2018, 25 pages.
Wang et. al., An adaptive decorrelation method removes Illumina DNA base-calling errors caused by crosstalk between adjacent clusters—with Supplemental Materials, Scientific Reports, published Feb. 20, 2017, 17 pages.
Pfeiffer et. al., Systematic evaluation of error rates and causes in short samples in next-generation sequencing, Scientific Reports, published Jul. 19, 2018, 14 pages.
Puckelwartz et al., Supercomputing for the parallelization of whole genome analysis, Bioinformatics, dated Feb. 12, 2014, pp. 1508-1513, 6 pages.
Kelly et al., Churchill: an ultra-fast, deterministic, highly scalable and balanced parallelization strategy for the discovery of human genetic variation in clinical and population-scale genomics, Genome Biology, Bio-Med Central Ltd, vol. 16, No. 1, dated Jan. 20, 2015, 14 pages.
Wang et al., Achieving Accurate and Fast Base-calling by a Block model of the Illumina Sequencing Data, Science Direct, vol. 48, No. 28, dated Jan. 1, 2015, pp. 1462-1465, 4 pages.
Gao et al., Deep Learning in Protein Structural Modeling and Design, Patterns—CelPress, dated Dec. 11, 2020, 23 pages.
Pejaver et al., Inferring the molecular and phenotypic impact of amino acid variants with MutPred2—with Supplementary Information, Nature Communications, dated 2020, 59 pages.
Pakhrin et al., Deep learning based advances in protein structure prediction, International Journal of Molecular sciences, published May 24, 2021, 30 pages.
Wang et al. Predicting the impacts of mutations on protein-ligand binding affinity based on molecular dynamics simulations and machine learning methods, Computational and Structural Biotechnology Journal 18, dated Feb. 20, 2022, pp. 439-454, 16 pages.
Iqbal et al., Comprehensive characterization of amino acid positions in protein structures reveals molecular effects of missense variants, and supplemental information, PNAS, vol. 117, No. 45, dated Nov. 10, 2020, 35 pages.
Forghani et al., Convolutional Neural Network Based Approach to In Silica Non-Anticipating Prediction of Antigenic Distance for Influenza Virus, Viruses, published Sep. 12, 2020, vol. 12, 20 pages.
Jing et al., Learning from protein structure with geometric vector perceptrons, Arxiv: 2009: 01411v2, dated Dec. 31, 2020, 18 pages.
Hacteria Wiki, HiSeq2000—Next Level Hacking—Hackteria Wiki, retrieved on Apr. 12, 2021, retrieved from the internet [URL: https://www.hackteria.org/wiki/HiSeq2000_-_Next_Level_Hacking ], 42 pages.
Pei et al., A Topological Measurement for Weighted Protein Interaction Network, IEEE Computational Systems Bioinformatics Conference dated 2005, 11 pages.
Chun, S. & Fay, J. C. Identification of deleterious mutations within three human genomes. Genome Res. 19, 1553-1561 (2009).
Schwarz, J. M., Rodelsperger, C., Schuelke, M. & Seelow, D. MutationTaster evaluates disease-causing potential of sequence alterations. Nat. Methods 7, 575-576 (2010).
Reva, B., Antipin, Y., & Sander, C. Predicting the functional impact of protein mutations—application to cancer genomics. Nucleic Acids Res. 39, e118 (2011), 14pgs.
Dong, C. et al. Comparison and integration of deleteriousness prediction methods for nonsynonymous SNVs in whole exome sequencing studies. Hum. Mol. Genet. 24, 2125-2137 (2015).
Carter, H., Douville, C., Stenson, P. D., Cooper, D. N., & Karchin, R. Identifying Mendelian disease genes with the variant effect scoring tool. BMC Genom, (2013), 13 pages.
Choi, Y., Sims, G. E., Murphy, S., Miller, J. R., & Chan, A. P. Predicting the functional effect of amino acid substitutions and indels. PLoS One 7, e46688 (2012).
Gulko, B., Hubisz, M. J., Gronau, I., & Siepel, A. A method for calculating probabilities of fitness consequences for point mutations across the human genome. Nat. Genet. 47, 276-283 (2015).
Shihab, H. A. et al. An integrative approach to predicting the functional effects of non-coding and coding sequence variation. Bioinformatics 31, 1536-1543 (2015).
Bell, C. J. et al. Comprehensive carrier testing for severe childhood recessive diseases by next generation sequencing. Sci. Transl. Med. 3, Jan. 12, 2011, 28 pages.
Smedley, D. et al. A whole-genome analysis framework for effective identification of pathogenic regulatory variants in mendelian disease. Am. J. Hum. Genet. 99, 595-606 (2016).
Jagadeesh, K. A. et al. M-CAP eliminates a majority of variants of uncertain significance in clinical exomes at high sensitivity. Nat. Genet. 48, 1581-1586 (2016).
Grimm, D. G. The evaluation of tools used to predict the impact of missense variants is hindered by two types of circularity. Human. Mutat. 36, 513-523 (2015).
Hefferman, R. et al. Improving prediction of secondary structure, local backbone angles, and solvent accessible surface area of proteins by iterative deep learning. Sci. Rep. 5, 11476 (2015) 11 pages.
Wang, S., Peng, J., Ma, J. & Xu, J. Protein secondary structure prediction using deep convolutional neural fields. Sci. Rep. 6, 18962-18962 (2016).
Harpak, A., Bhaskar, A., & Pritchard, J. K. Mutation rate variation is a primary determinant of the distribution of allele frequencies in humans. PLoS Genet. Dec. 15, 2016, 22pgs.
Payandeh, J., Scheuer, T., Zheng, N. & Catterall, W. A. The crystal structure of a voltage-gated sodium channel. Nature 475, 353-358 (2011).
Shen, H. et al. Structure of a eukaryotic voltage-gated sodium channel at near-atomic resolution. Science 355, eaal4326 (2017), 19 pages.
Nakamura, K. et al. Clinical spectrum of SCN2A mutations expanding to Ohtahara syndrome. Neurology 81, 992-998 (2013).
Ioannidis, Nilah M., et al., "REVEL—An Ensemble Method for Predicting the Pathogenicity of Rare Missense Variants", Oct. 5, 2016, 9 pages.
Quang Daniel, et. al., "DANN—a deep learning approach for annotating the pathogenicity of genetic variants", Oct. 22, 2014, 3 pages.
Sundaram, et. al., "Predicting the clinical impact of human mutation with deep neural networks", Aug. 2018, 15pgs.
Xiong, et. al., "The human splicing code reveals new insights into the genetic determinants of disease", Jan. 9, 2015, 20pgs.
Yue, et. al., "Deep Learning for Genomics—A Concise Overview from internet", May 8, 2018, 40pgs.
Yuen, et. al., "Genome wide characteristics of de novo mutations in autism", Jun. 1, 2016, 10pgs.
Libbrecht, et. al., "Machine learning in genetics and genomics", Jan. 2, 2017, 30pgs.
Min, et. al., "Deep Learning in Bioinformatics", Jul. 25, 2016, 19 pgs.
Torng, Wen, et al., "3D deep convolutional neural networks for amino acid environment similarity analysis", 2017, 23pages.
Chen, Kathleen M., et. al., "Selene—a PyTorch based deep learning library for sequence level data", Oct. 10, 2018, 15pages.
Grob, C., et. al., "Predicting variant deleteriousness in non human species Applying the CADD approach in mouse", 2018, 11 pages.
Li, et. al., "FoldingZero—Protein Folding from Scratch in Hydrophobic Polar Model", Dec. 3, 2018, 10 pages.
Rentzsch, et. al.,_"CADD—predicting the deleteriousness of variants throughout the human genome", Oct. 11, 2018, 9 pages.
Zou, etal, "A primer on deep learning in genomics", Nov. 26, 2018, 7pages.
Alberts, Bruce, et al., "Molecular biology of the cell", Sixth Edition, 2015, 3 pages.
Wei etal_The Role of Balanced Training and Testing Data Sets for Binary Classifiers in Bioinformatics dated Jul. 9, 2013 12 pages.
Duggirala, Ravindranath, et.al., "Genome Mapping and Genomics in Human and Non Human Primate", 2015, 306pgs.
Brookes, Anthony J., "The essence of SNPs", 1999, pp. 177-186.
UniProtKB P04217 A1BG Human [retrieved on Mar. 13, 2019 from (www.uniprot.org/uniprot/P04217), 12pages.

(56) References Cited

OTHER PUBLICATIONS

Bahar, Protein Actions Principles and Modeling, Chapter 7, 2017 pp. 165-166.
Dunbrack, Roland L., Re Question about your Paper titled "The Role of Balanced Training and Testing Data Sets for Binary Classifiers in Bioinformatics", Message to Sikander Mohammed Khan, Feb. 3, 2019, E-mailm, 3pgs.
DbSNP rs2241788 [Retrieved on Mar. 13, 2019], Retrieved from the Internet<www.ncbi.nlm.nih.gov/snp/rs2241788>, 5 pages.
Wei, et. al., "Prediction of phenotypes of missense mutations in human proteins from biological assemblies", Feb. 2013, 28 pages.
Zhang, Jun, and Bin Liu. "PSFM-DBT—identifying DNA-binding proteins by combing position specific frequency matrix and distance-bigram transformation." International journal of molecular sciences 18.9 (2017) 1856.
Gao, Tingting, et al. "Identifying translation initiation sites in prokaryotes using support vector machine." Journal of theoretical biology 262.4 (2010) 644-649. (Year 2010).
Bi, Yingtao, et al. "Tree-based position weight matrix approach to model transcription factor binding site profiles." PloS one6.9 (2011) e24210.
Korhonen, Janne H., et al. "Fast motif matching revisited—high-order PWMs, SNPs and indels." Bioinformatics 33.4 (2016) 514-521.
Wong, Sebastien C., et al. "Understanding data augmentation for classification—when to warp?." 2016 international conference on digital image computing—techniques and applications (DICTA). IEEE, 2016.
Chang, Chia-Yun, et al. "Oversampling to overcome overfitting—exploring the relationship between data set composition, molecular descriptors, and predictive modeling methods." Journal of chemical information and modeling 53.4 (2013) 958-971.
Li, Gangmin, and Bei Yao. "Classification of Genetic Mutations for Cancer Treatment with Machine Learning Approaches." International Journal of Design, Analysis and Tools for Integrated Circuits and Systems 7.1 (2018) pp. 63-67.
Martin-Navarro, Antonio, et al. "Machine learning classifier for identification of damaging missense mutations exclusive to human mitochondrial DNA-encoded polypeptides." BMC bioinformatics 18.1 (2017) p. 158.
Krizhevsky, Alex, et al, ImageNet Classification with Deep Convolutional Neural Networks, 2012, 9 Pages.
Assfalg et. al., "3DString, A Feature String Kernel for 3D Object Classification on Voxelized Data", dated Nov. 6, 2006, 10 pages.
Sifre et. al., Rigid-motion Scattering for Texture Classification, Ph.D. thesis submitted for publishing.
Linder, Modeling the intronic regulation of Alternative Splicing using Deep Convolutional Neural Nets, KTH Institute of Technology, dated Jun. 14, 2015, 53 pages.
Bentley et. al., Accurate Whole Human Genome Sequencing using Reversible Terminator Chemistry, Nature, Nov. 2008, 21 pages.
Illumina CMOS Chip and One-Channel SBS Chemistry, Illumina Inc, 2018, 4 pages.
Ilumina, Calculating Percent Passing Filter for Patterned and Nonpatterned Flow Cells, 2017, 2 pages.
Fritzilas, An Overview of Illumina's Sequencing Technology and its Applications, University of Primorska, dated Mar. 4, 2011, 47 pages.
Python Implementation of the color map function for the Pascal Voc data set, Github, 4 pages, retrieved on Jul. 23, 2021. Retrieved from [URL: https://gist.github.com/wllhf/a4533e0adebe57e3ed0 6d4b50c8419ae ].
Illumina, Quality Score Encoding, 2 pages, retrieved on Jul. 23, 2021. Retrieved from [URL: https://support.illumina.com/help/BaseSpace_OLH_009008/Content/Source/Informatics/BS/QualityScoreEncoding_swBS.htm ].
Illumina, Reducing Whole-Genome Data Storage Footprint, Illumina Whitepaper, 2010-2014, 4 pages.
Badrinarayanan et. al., SegNet: A Deep Convolutional Encoder-Decoder Architecture for Image Segmentation, dated Oct. 10, 2016, 14 pages.
Li et. al., CS231 Lecture 13 Segmentation and Attention, Stanford University, dated Feb. 24, 2016, 133 pages.
Whiteford et. al., Swift: Primary data analysis for the Illumina Solexa sequencing platform, Bioinformatics, vol. 25, No. 17, 2009, pp. 2194-2199, 7 pages.
Schilling, The Effect of Batch Normalization on Deep Convolutional Neural Networks, KTH Royal Institute of Technology, 2016, 113 pages.
Tutorial Image Segmentation, BoofCV, 6 pages, retrieved on Jul. 23, 2021. Retrieved from [URL: https://boofcv.org/index.php?title=Tutorial_Image_Segmentation ].
Illumina, Understanding Illumina Quality Scores, dated Apr. 23, 2014, 2 pages.
Zhang et. al., Estimating Phred scores of Illumina base calls by logistic regression and sparse modeling, Bio Med Central Bioinformatics, 2017, 14 pages.
Renaud et. al., freelbis: an efficient base caller with calibrated quality scores for Illumina sequencers, dated Mar. 6, 2013, 2 pages.
Kircher, Improving data quality of the Illumina Genome Analyzer platform, Max Planck Institute for Evolutionary Anthropology, dated Oct. 24, 2009, 46 pages.
Mitra et. al., Strategies for Achieving High Sequencing Accuracy for Low Diversity Samples and Avoiding Sample Bleeding Using Illumina Platform, PLOS One, published Apr. 10, 2015, 21 pages.
Datta et. al., Statistical Analyses of Next Generation Sequence Data: A Partial Overview, Journal of Proteomics and Bioinformatics, vol. 3, Issue 6, 2010, 8 pages.
Erlich et. al., Alta-Cyclic: a self-optimizing base-caller for next generation sequencing, Nature Methods, Aug. 2008, 7 pages.
Kao et. al., Algorithms for Next-Generation High-Throughput Sequencing Technologies, University of California, Berkeley, 2011, 106 pages.
Kircher et. al., Addressing challenges in the production and analysis of Illumina sequencing data, published Jul. 29, 2011, retrieved on Jul. 24, 2021, 25 pages. Retrieved from [URL: https://www.ncbi.nlm.nih.gov/pmc/articles/PMC3163567/ ].
Teng et. al., Chiron: translating nanopore raw signal directly into nucleotide sequence using deep learning, GigaScience, 7, 2018, 9 pages.
Ratkovic, Deep Learning Model for Base Calling of MinION Nanopore Reads, dated Jun. 2017, 48 pages.
Teng et. al., Chiron: translating nanopore raw signal directly into nucleotide sequence using deep learning, dated Aug. 23, 2017, 10 pages.
Stoiber et. al., BasecRAWller: Streaming Nanopore Basecalling Directly from Raw Signal, dated May 1, 2017, 15 pages.
Li et. al., DeepSimulator: a deep simulator for Nanopore sequencing, Bioinformatics 34(17), 2018, pp. 2899-2908, 10 pages.
Wick et. al., Performance of neural network basecalling tools for Oxford Nanopore sequencing, dated Feb. 7, 2019, 14 pages.
Ledergerber et. al., Base-calling for next-generation sequencing platforms, Briefings in Bioinformatics vol. 12, No. 5, pp. 489-497, dated Jan. 18, 2011, 9 pages.
Sheikh et. al., Chapter 5 Base-Calling for Bioinformaticians, 2012, 17 pages.
Kriseman et. al., BING: Biomedical informatics pipeline for Next Generation Sequencing, Journal of Biomedical Informatics, vol. 43, 2010, pp. 428-434, 7 pages.
Das et. al., Model-based sequential base calling for Illumina sequencing, IEEE, 2010, 4 pages.
Shamaiah et. al., Base calling error rates in next-generation DNA sequencing, IEEE Statistical Signal Processing Workshop, 2012, 4 pages.
Ye et. al., BlindCall: ultra-fast base-calling of high-throughput sequencing data by blind deconvolution, Bioinformatics, vol. 30, No. 9, 2014, pp. 1214-1219, 6 pages.
Wolowski, High-quality, high-throughput measurement of protein-DNA binding using HiTS-FLIP, Ludwig Maxmilian University, 2016, 251 pages.

(56) References Cited

OTHER PUBLICATIONS

Bravo et. al., Model-Based Quality Assessment and Base-Calling for Second-Generation Sequencing Data, Biometrics, 2009, 10 pages.
Illumina, RTA Theory of Operation, 2009, 8 pages.
Dash et. al., Artificial Intelligence and Evolutionary Computations in Engineering Systems, Advances in Intelligent Systems and Computing, vol. 1056, Springer 2020, 781 pages.
Ahmed, SIGNET: A Neural Network Architecture for Predicting Protein-Protein Interactions, The University of Western Ontario, dated May 7, 2017, 84 pages.
Deepa J, Development of Fully Automated Image Analysis Method for High Density cDNA and array CGH Microarray based genomic studies, Cochin University of Science and Technology, Mar. 2013, 232 pages.
Zhang et. al., Nanopore basecalling from a perspective of instance segmentation, BMC Bioinformatics, 2020, 9 pages.
Kao et. al., naiveBayesCall: An Efficient Model-Based Base-Calling Algorithm for High-Throughput Sequencing, Journal of Computational Biology, dated Mar. 2011, 16 pages.
Wick et. al., Performance of neural network basecalling tools for Oxford Nanopore sequencing, Genome Biology, 2019, 10 pages.
Baek et. al., LncRNAnet: long non-coding RNA identification using deep learning, Bioinformatics, vol. 34 (22), 2018, pp. 3889-3897, 9 pages.
Evans et. al., Estimating Change-Points in Biological Sequences via the Cross-Entropy Method, dated Sep. 20, 2010, 17 pages.
Shen et. al., ParticleCall: A particle filter for base calling in next-generation sequencing systems, BMC Bioinformatics, 2012, 10 pages.
Peresini et. al., Nanopore Base Calling on the Edge, dated Nov. 9, 2020, 15 pages.
Liang et. al., Bayesian Basecalling for DNA Sequence Analysis Using Hidden Markov Models, IEEE Transactions on Computational Biology and Bioinformatics, vol. 4, No. 3, Jul.-Sep. 2007, 11 pages.
Wang et. al., DeepDNA: a hybrid convolutional and recurrent neural network for compressing human mitochondrial genomes, IEEE International Conference on Bioinformatics and Biomedicine, 2018, 5 pages.
Anonymous, Vanishing Gradient Problem, Wikipedia, dated Jun. 16, 2018, retrieved on Jan. 12, 2020. Retrieved from [URL: https://en.wikipedia.org/w/index.php?title=Vanishing_gradient_problem&oldid=846115335 ].
Zhang Buanzhi et al., "Stable oligonucleotides Synthesis of silver nanocluster fluorescent probes High selection of synthetic and sulfhydryl-containing drugs" Selective Analytical Assay—Science China Chemistry, vol. 41, No. 6, (2011) 1031-1036.
Geeks for Geeks, "Underfitting and Overfilling in Machine Learning", [retrieved on Aug. 26, 2019]. Retrieved from the Internet <www.geeksforgeeks.org/underfitting-and-overfitting-in-machine--learning/>, 2 pages.
Despois, Julien, "Memorizing is not learning!—6 tricks to prevent overfitting in machine learning", Mar. 20, 2018, 17 pages.
Bhande, Anup What is underfitting and overfitting in machine learning and how to deal with it, Mar. 11, 2018, 10pages.
Carter et al., "Cancer-specific high-throughput annotation of somatic mutations—computational prediction of driver missense mutations," Cancer research 69, No. 16 (2009) pp. 6660-6667.
Min, et. al., "Deep Learning in Bioinformatics", Jun. 19, 2016, 46pgs.
Jiminez et. al., DeepSite—protein binding site predictor using 3D CNNs, dated Oct. 1, 2017, 7 pages.
Pu et. al., "DeepDrug3D: Classification of ligand-binding pockets in proteins with a convolutional neural network", dated Feb. 4, 2019, 23 pages.
Adam, "Deep learning, 3D technology to improve structure modeling for protein interactions, create better drugs", dated Jan. 9, 2020, 4 pages.
Varela, "Ligvoxel: A Deep Learning Pharmacore-Field Predictor", dated Mar. 19, 2019, 5 pages.
Li et. al., "Predicting changes in protein thermostability upon mutation with deep 3D convolutional neural networks", dated Feb. 28, 2020, 21 pages.
Raschka et. al., "Machine Learning and AI-based approaches for bioactive ligand discovery and GPCR-ligand recognition", dated Jun. 6, 2020, 33 pages.
Morrone et. al., "Combining docking pose rank and structure with deep learning improves protein-ligand binding mode prediction", dated Oct. 7, 2019, 13 pages.
Li, "Machine Learning Methods for Medical and Biological Image Computing", dated Summer 2016, 113 pages.
Rivera et. al., "A Deep Learning Approach to Protein Structure Prediction", dated Apr. 24, 2019, 22 pages.
Aritake et. al., "Single-molecule localization by voxel-wise regression using convolutional neural network", dated Nov. 3, 2020, 11 pages.
Townshend et. al., "End-to-End Learning on 3D Protein Structure for Interface Prediction", dated 2019, 10 pages.
Amidi et. al., "EnzyNet: enzyme classification using 3D convolutional neural networks on spatial representation", dated Jul. 25, 2017, 18 pages.
Luna, "Machine Learning in structural biology and chemoinformatics", dated 2019, 106 pages.
Anonymous, "Transferrable end-to-end learning for protein interface prediction", dated 2019, 12 pages.
Dias et. al., "Artificial intelligence in clinical and genomic diagnostics", dated 2019, 12 pages.
Luna et. al., "A Deep-Learning Approach toward Rational Molecular Docking Protocol Selection", dated May 27, 2020, 12 pages.
Li et. al., "DeepAtom: A Framework for Protein-Ligand Binding Affinity Prediction", dated 2019, 8 pages.
Zhang et. al., "Template-based prediction of protein structure with deep learning", dated Jun. 2, 2020, 16 pages.
Wallach et. al., AtomNet: A Deep Convolutional Neural Network for Bioactivity Prediction in Structure-based Drug Discovery, dated Oct. 10, 2015, 11 pages.
Illumina, Two-Channel SBS Sequencing Technology, 2016, 2 pages.
Illumina, Low-diversity sequencing on the Illumina HiSeq Platform, 2014, 2 pages.
Hedegaard, An introduction to "Next Generation" DNA Sequencing, dated Nov. 26, 2017, 63 pages.
Jordan , An overview of semantic image segmentation, dated May 21, 2018, 28 pages retrieved on Jul. 21, 2021. Retrieved from the internet [URL: https://www.jeremyjordan.me/semantic-segmentation/ ].
Lanchantin, Deep Motif Dashboard: Visualizing and Understanding Genomic Sequences Using Deep Neural Networks, Oct. 18, 2016, 11 pages.
Thalles Silva, Deeplab Image Semantic Segmentation Network, dated Jan. 29, 2018, 19 pages, retrieved on Jul. 21, 2021. Retrieved from [URL: https://sthalles.github.io/deep_segmentation_network/].
James Le, How to do Semantic Segmentation using Deep Learning, dated May 3, 2018, 17 pages, retrieved on Jul. 21, 2021. Retrieved from [URL: https://medium.com/nanonets/how-to-do-image-segmentation-using-deep-learning-c673cc5862ef].
Townley, Illumina Primary and Secondary Analysis, Illumina UK, 2010, 33 pages.
Silver, Literature Review: Fully Convolutional Networks, dated Jun. 12, 2017, 5 pages, retrieved on Jul. 21, 2021. Retrieved from [URL: https://medium.com/self-driving-cars/literature-review-fully-convolutional-networks-d0a11fe0a7aa ].
Bowen, Nanotechnology for a Genomic Revolution, Illumina, dated Dec. 14, 2016, 40 pages.
Han, Deconvolutions in Convolutional Neural Networks, Postech Computer Vision Lab, 2015, 20 pages.
Illumina, Illumina's Genotyping Data Normalization Methods, 2006, 6 pages.
Illumina, Quality Scores for Next-Generation Sequencing—Assessing sequencing accuracy using Phred quality scoring, 2011, 2 pages.

(56) References Cited

OTHER PUBLICATIONS

Restrepo, A Gentle Introduction to Semantic Segmentation—Inputs, Labels and Outputs, 2 pages, retrieved on Jul. 21, 2021. Retrieved from [URL: http://ronny.rest/tutorials/module/seg_01/segmentation_03_inputs_outputs/].
Illumina, An Introduction to Next-Generation Sequencing Technology, 2017, 16 pages.
Belanovic, Library of Parameterized Hardware Modules for Floating-Point Arithmetic with an Example Application, Northeastern University, Boston, MA, May 2002, 83 pages.
Massingham, Base Calling: methods, problems and alternatives, EMBL Advanced Course in Analysis of Short Read Sequencing Data, Jun. 8, 2009-Jun. 10, 2009, 84 pages.
Thoma, A Survey of Semantic Segmentation, dated May 11, 2016, 16 pages.
Rodriguez-Ezpeleta, Bioinformatics for High Throughput Sequencing, Springer, 2012, 266 pages.
Illumina, Optimizing Cluster Density on Illumina Sequencing Systems, 2016, 12 pages.
Boza et. al., DeepNano: Deep recurrent neural networks for base calling in MinION nanopore reads, Plos One, dated Jun. 5, 2017, 13 pages.
Kircher, Understanding and Improving high-throughput sequencing data production and analysis, Leipzig University, 2011, 216 pages.
Lutteropp, Error-Profile-Aware Correction of Next Generation Sequencing Reads, Karlsruhe Institute of Technology, dated Mar. 31, 2017, 96 pages.
Illumina, HCS 1.4/RTA 1.12 Theory of Operation, 2010, 32 pages.
Cacho, Base-Calling of High-throughput Sequencing Data Using a Random Effects Mixture Model, UC Riverside, Dec. 2016, 102 pages.
Zhou et. al., Incorporating Side-Channel Information into Convolutional Neural Networks for Robotic Tasks, 2017, 7 pages.
Gong et al., "Compressing Deep Convolutional Networks using Vector Quantization," Dec. 18, 2014, https://arxiv.org/abs/1412.6115.
O'Roak, B. J. et al. Sporadic autism exomes reveal a highly interconnected protein network of de novo mutations. Nature 485, 246-250 (2012).
Rauch, A. et al. Range of genetic mutations associated with severe non-syndromic sporadic intellectual disability—an exome sequencing study. Lancet 380, 1674-1682 (2012).
Epi, K. C. et al. De novo mutations in epileptic encephalopathies. Nature 501, 217-221 (2013).
EuroEPINOMICS-RES Consortium, Epilepsy Phenome/Genome Project, Epi4K Consortium. De novo mutations in synaptic transmission genes including DNM1 cause epileptic encephalopathies. Am. J. Hum. Genet. 95, 360-370 (2014).
Gilissen, C. et al. Genome sequencing identifies major causes of severe intellectual disability. Nature 511, 344-347 (2014).
Lelieveld, S. H. et al. Meta-analysis of 2, 104 trios provides support for 10 new genes for intellectual disability. Nat. Neurosci. 19, 1194-1196 (2016).
Famiglietti, M. L. et al. Genetic variations and diseases in UniProtKB Swiss-Prot—the ins and outs of expert manual curation. Human. Mutat. 35, 927-935 (2014).
Horaitis, O., Talbot, C. C.Jr., Phommarinh, M., Phillips, K. M., & Cotton, R. G. A database of locus-specific databases. Nat. Genet. 39, 425 (2007).
Stenson, P. D. et al. The Human Gene Mutation Database—building a comprehensive mutation repository for clinical and molecular genetics, diagnostic testing and personalized genomic medicine. Hum. Genet. 133, 1-9 (2014).
Alipanahi, et. al., "Predicting the Sequence Specificities of DNA and RNA Binding Proteins by Deep Learning", Aug. 2015, 9pgs.
Angermueller, et. al., "Accurate Prediction of Single Cell DNA Methylation States Using Deep Learning", Apr. 11, 2017, 13pgs.
Ching, et. al., "Opportunities and Obstacles for Deep Learning in Biology and Medicine", Jan. 19, 2018, 123pgs.
Ching, et. al., "Opportunities and Obstacles for Deep Learning in Biology and Medicine", May 26, 2017, 47pgs.
Gu et. al., Recent Advances in Convolutional Neural Networks, dated Jan. 5, 2017, 37 pages.
Leung, et. al., "Deep learning of the tissue regulated splicing code", 2014, 9pgs.
Leung, et. al., "Inference of the Human Polyadenylation Code", Apr. 27, 2017, 13pgs.
Leung, et. al., "Machine Learning in Genomic Medicine", Jan. 1, 2016, 22pgs.
Park, et. al., "Deep Learning for Regulatory Genomics", Aug. 2015, 2pgs.
MacArthur, D. G. et al. Guidelines for investigating causality of sequence variants in human disease. Nature 508, 469-476 (2014).
Rehm, H. L. et al. ClinGen—the Clinical Genome Resource. N. Engl. J. Med. 372, 2235-2242 (2015).
Bamshad, M. J. et al. Exome sequencing as a tool for Mendelian disease gene discovery. Nat. Rev. Genet. 12, 745-755 (2011).
Rehm, H. L. Evolving health care through personal genomics. Nat. Rev. Genet. 18, 259-267 (2017).
Richards, S. et al. Standards and guidelines for the interpretation of sequence variants—a joint consensus recommendation of the American College of Medical Genetics and Genomics and the Association for Molecular Pathology. Genet. Med. 17, 405-424 (2015).
Lek, M. et al. Analysis of protein-coding genetic variation in 60,706 humans. Nature 536, 285-291 (2016).
Mallick, S. et al. The Simons Genome Diversity Project—300 genomes from 142 diverse populations. Nature 538, 201-206 (2016).
Genomes Project Consortium. et al. A global reference for human genetic variation. Nature 526, 68-74 (2015).
Liu, X., Jian, X. & Boerwinkle, E. dbNSFP—a lightweight database of human nonsynonymous SNPs and their functional predictions. Human. Mutat. 32, 894-899 (2011).
Chimpanzee Sequencing Analysis Consortium. Initial sequence of the chimpanzee genome and comparison with the human genome. Nature 437, 69-87 (2005).
Takahata, N. Allelic genealogy and human evolution. Mol. Biol. Evol. 10, 2-22 (1993).
Asthana, S., Schmidt, S., & Sunyaev, S. A limited role for balancing selection. Trends Genet. 21, 30-32 (2005).
Leffler, E. M. et al. Multiple instances of ancient balancing selection shared between humans and chimpanzees. Science 339, 12 pages (2013).
Samocha, K. E. et al. A framework for the interpretation of de novo mutation in human disease. Nat. Genet. 46, 944-950 (2014).
Ohta, T. Slightly deleterious mutant substitutions in evolution. Nature 246, 96-98 (1973).
Reich, D. E. & Lander, E. S. On the allelic spectrum of human disease. Trends Genet. 17, 502-510 (2001).
Whiffin, N. et al. Using high-resolution variant frequencies to empower clinical genome interpretation. Genet. Med. 19, 1151-1158(2017).
Prado-Martinez, J. et al. Great ape genome diversity and population history. Nature 499, 471-475 (2013).
Klein, J., Satta, Y., O'HUigin, C., & Takahata, N. The molecular descent of the major histocompatibility complex. Annu. Rev. Immunol. 11, 269-295 (1993).
De Manuel, M. et al. Chimpanzee genomic diversity reveals ancient admixture with bonobos. Science 354, 477-481 (2016).
Locke, D. P. et al. Comparative and demographic analysis of orang-utan genomes. Nature 469, 529-533 (2011).
Rhesus Macaque Genome Sequencing Analysis Consortium. Evolutionary and biomedical insights from the rhesus macaque genome. Science 316, 222-234 (2007).
Worley, K. C. et al. The common marmoset genome provides insight into primate biology and evolution. Nat. Genet. 46, 850-857 (2014).
Sherry, S. T. et al. dbSNP—the NCBI database of genetic variation. Nucleic Acids Res. 29, 308-211 (2001).
Schrago, C. G., & Russo, C. A. Timing the origin of New World monkeys. Mol. Biol. Evol. 20, 1620-1625 (2003).
Landrum, M. J. et al. ClinVar—public archive of interpretations of clinically relevant variants. Nucleic Acids Res. 44, D862-868 (2016).

(56) References Cited

OTHER PUBLICATIONS

Brandon, E. P., Idzerda, R. L. & McKnight, G. S. Targeting the mouse genome—a compendium of knockouts (Part II). Curr. Biol. 5, 758-765 (1995).

Lieschke, J. G. & Currie, P. D. Animal models of human disease—zebrafish swim into view. Nat. Rev. Genet. 8, 353-367 (2007).

Sittig, L. J. et al. Genetic background limits generalizability of genotype-phenotype relationships. Neuron 91, 1253-1259 (2016).

Bazykin, G. A. et al. Extensive parallelism in protein evolution. Biol. Direct 2, 20, 13 pages (2007).

Ng, P. C., & Henikoff, S. Predicting deleterious amino acid substitutions. Genome Res. 11, 863-874 (2001).

Adzhubei, I. A. et al. A method and server for predicting damaging missense mutations. Nat. Methods 7, 248-249 (2010).

Eltoukhy, Helmy et al., "Modeling and base-calling for DNA Sequencing-by-Synthesis", 2006 IEEE International Conference on Acoustics Speech and Signal Processing Proceedings 2 (2006): II-II 1032-1035, May 14-19, 2006. DOI: 10.1109/ICASSP.2006.1660522.

Ewing, Brett et al., "Base-Calling of Automated Sequencer Traces Using Phred. I. Accuracy Assessment", Genome Research, Mar. 1, 1998, 8:175-185; doi:10.1101/gr.8.3.175.

Giddings, M.C. et al., "An adaptive, object oriented strategy for base calling in DNA sequence analysis", Nucleic Acid Research, 1993, vol. 21, No. 19, 4530-4550. https://academic.oup.com/nar/article/21/19/4530/1014808.

Ju, J. et al., "Four-color DNA sequencing by synthesis using cleavable fluorescent nucleotide reversible terminators", PNA, vol. 103 No. 52, 19635-19640, Dec. 26, 2006. https://www.pnas.org/doi/full/10.1073/pnas.0609513103.

Software Application, "Creating A Template of Nucleic Acid Site Locations on a Flow Cell", published Feb. 27, 2007 (accessed online Dec. 16, 2025), BCGSC, Canada's Michael Smith Genome Sciences Centre, 124,665 pages. URL: https://www.bcgsc.ca/downloads/parts/software/resources/src/.

* cited by examiner

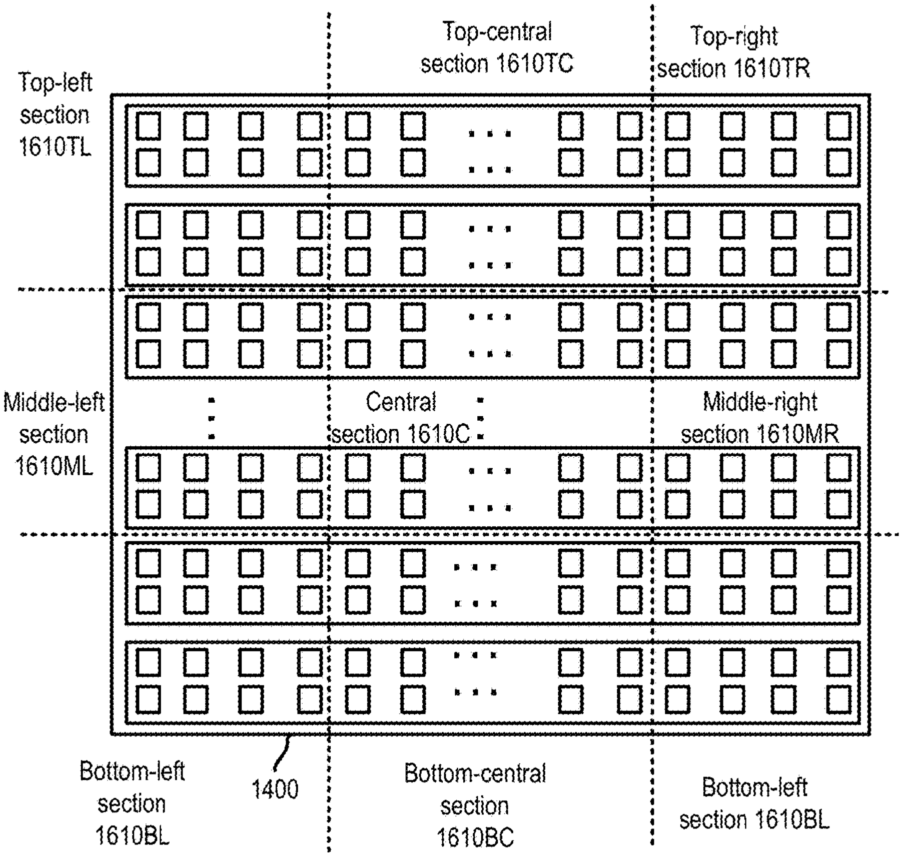

| | Cycles 1 to N1 | Cycles (N1+1) to N2 | Cycles (N2+1) to N |
|---|---|---|---|
| Top-left section 1610TL | Weight set (TL,(1-N1)) | Weight set (TL,(N1-N2)) | Weight set (TL,(N2-N)) |
| Top-central section 1610TC | Weight set (TC,(1-N1)) | Weight set (TC,(N1-N2)) | Weight set (TC,(N2-N)) |
| Top-right section 1610TR | Weight set (TR,(1-N1)) | Weight set (TR,(N1-N2)) | Weight set (TR,(N2-N)) |
| Middle-left section 1610ML | Weight set (ML,(1-N1)) | Weight set (ML,(N1-N2)) | Weight set (ML,(N2-N)) |
| Central section 1610C | Weight set (C,(1-N1)) | Weight set (C,(N1-N2)) | Weight set (C,(N2-N)) |
| Middle-right section 1610MR | Weight set (MR,(1-N1)) | Weight set (MR,(N1-N2)) | Weight set (MR,(N2-N)) |
| Bottom-left section 1610BL | Weight set (BL,(1-N1)) | Weight set (BL,(N1-N2)) | Weight set (BL,(N2-N)) |
| Bottom-central section 1610BC | Weight set (BC,(1-N1)) | Weight set (BC,(N1-N2)) | Weight set (BC,(N2-N)) |
| Bottom-left section 1610BL | Weight set (BL,(1-N1)) | Weight set (BL,(N1-N2)) | Weight set (BL,(N2-N)) |

2150

Fig. 21B

TILE LOCATION AND/OR CYCLE BASED WEIGHT SET SELECTION FOR BASE CALLING

PRIORITY APPLICATIONS

This application claims the benefit of U.S. Provisional Patent Application No. 63/161,880, titled "Tile Location and/or Cycle Based Weight Set Selection for Base Calling", filed Mar. 16, 2021. The priority provisional application is hereby incorporated by reference for all purposes.

This application claims the benefit of U.S. Provisional Patent Application No. 63/161,896, titled "Neural Network Parameter Quantization for Base Calling", filed Mar. 16, 2021. The priority provisional application is hereby incorporated by reference for all purposes.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as deep convolutional neural networks for analyzing data, and selective use of weight sets.

INCORPORATIONS

The following are incorporated by reference as if fully set forth herein:

- Nonprovisional patent application titled "NEURAL NETWORK PARAMETER QUANTIZATION FOR BASE CALLING," filed contemporaneously;
- U.S. Provisional Patent Application No. 62/979,384, titled "ARTIFICIAL INTELLIGENCE-BASED BASE CALLING OF INDEX SEQUENCES," filed 20 Feb. 2020;
- U.S. Provisional Patent Application No. 62/979,414, titled "ARTIFICIAL INTELLIGENCE-BASED MANY-TO-MANY BASE CALLING," filed 20 Feb. 2020;
- U.S. Provisional Patent Application No. 62/979,385, titled "KNOWLEDGE DISTILLATION-BASED COMPRESSION OF ARTIFICIAL INTELLIGENCE-BASED BASE CALLER," filed 20 Feb. 2020;
- U.S. Provisional Patent Application No. 63/072,032, titled "DETECTING AND FILTERING CLUSTERS BASED ON ARTIFICIAL INTELLIGENCE-PREDICTED BASE CALLS," filed 28 Aug. 2020;
- U.S. Provisional Patent Application No. 62/979,411, titled "DATA COMPRESSION FOR ARTIFICIAL INTELLIGENCE-BASED BASE CALLING," filed 20 Feb. 2020;
- U.S. Provisional Patent Application No. 62/979,399, titled "SQUEEZING LAYER FOR ARTIFICIAL INTELLIGENCE-BASED BASE CALLING," filed 20 Feb. 2020;
- U.S. Nonprovisional patent application Ser. No. 16/825,987, titled "TRAINING DATA GENERATION FOR ARTIFICIAL INTELLIGENCE-BASED SEQUENCING," filed 20 Mar. 2020;
- U.S. Nonprovisional patent application Ser. No. 16/825,991 titled "ARTIFICIAL INTELLIGENCE-BASED GENERATION OF SEQUENCING METADATA," filed 20 Mar. 2020;
- U.S. Nonprovisional patent application Ser. No. 16/826,126, titled "ARTIFICIAL INTELLIGENCE-BASED BASE CALLING," filed 20 Mar. 2020;
- U.S. Nonprovisional patent application Ser. No. 16/826,134, titled "ARTIFICIAL INTELLIGENCE-BASED QUALITY SCORING," filed 20 Mar. 2020;
- U.S. Nonprovisional patent application Ser. No. 16/826,168, titled "ARTIFICIAL INTELLIGENCE-BASED SEQUENCING," filed 21 Mar. 2020;
- U.S. Nonprovisional patent application Ser. No. 16/874,599, titled "Systems and Devices for Characterization and Performance Analysis of Pixel-Based Sequencing," filed May 14, 2020; and
- U.S. Nonprovisional patent application Ser. No. 17/176,147, titled "HARDWARE EXECUTION AND ACCELERATION OF ARTIFICIAL INTELLIGENCE-BASED BASE CALLER," filed Feb. 15, 2021.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

The rapid improvement in computation capability has made deep Convolution Neural Networks (CNNs) a great success in recent years on many computer vision tasks with significantly improved accuracy. During the inference phase, many applications demand low latency processing of one image with strict power consumption requirement, which reduces the efficiency of Graphics Processing Unit (GPU) and other general-purpose platform, bringing opportunities for specific acceleration hardware, e.g., Field Programmable Gate Array (FPGA), by customizing the digital circuit specific for the deep learning algorithm inference. However, deploying CNNs on portable and embedded systems is still challenging due to large data volume, intensive computation, varying algorithm structures, and frequent memory accesses.

As convolution contributes most operations in CNNs, the convolution acceleration scheme significantly affects the efficiency and performance of a hardware CNN accelerator. Convolution involves multiply and accumulate (MAC) operations with four levels of loops that slide along kernel and feature maps. The first loop level computes the MAC of pixels within a kernel window. The second loop level accumulates the sum of products of the MAC across different input feature maps. After finishing the first and second loop levels, a final output pixel is obtained by adding the bias. The third loop level slides the kernel window within an input feature map. The fourth loop level generates different output feature maps.

FPGAs have gained increasing interests and popularity in particular to accelerate the inference tasks, due to their (1) high degree of reconfigurability, (2) faster development time compared to application specific integrated circuits (ASICs) to catch up with the rapid evolving of CNNs, (3) good performance, and (4) superior energy efficiency compared to GPUs. The high performance and efficiency of an FPGA can be realized by synthesizing a circuit that is customized for a specific computation to directly process billions of operations with the customized memory systems. For instance, hundreds to thousands of Digital Signal Processing (DSP) blocks on modern FPGAs support the core convolution operation, e.g., multiplication and addition, with high parallelism. Dedicated data buffers between external on-chip memory and on-chip Processing Engines (PEs) can be designed to realize the preferred dataflow by configuring tens of Mbyte on-chip Block Random Access Memories (BRAM) on the FPGA chip.

Efficient dataflow and hardware architecture of CNN acceleration are desired to minimize data communication while maximizing resource utilization to achieve high performance. An opportunity arises to design methodology and framework to accelerate the inference process of various CNN algorithms on acceleration hardware with high performance, efficiency, and flexibility.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIGS. 19, 20, 21A, and 21B illustrate various example weight selection schemes based on (i) temporal progression of base calling cycle numbers and (ii) spatial locations of tiles.

DETAILED DESCRIPTION

Figure 1:
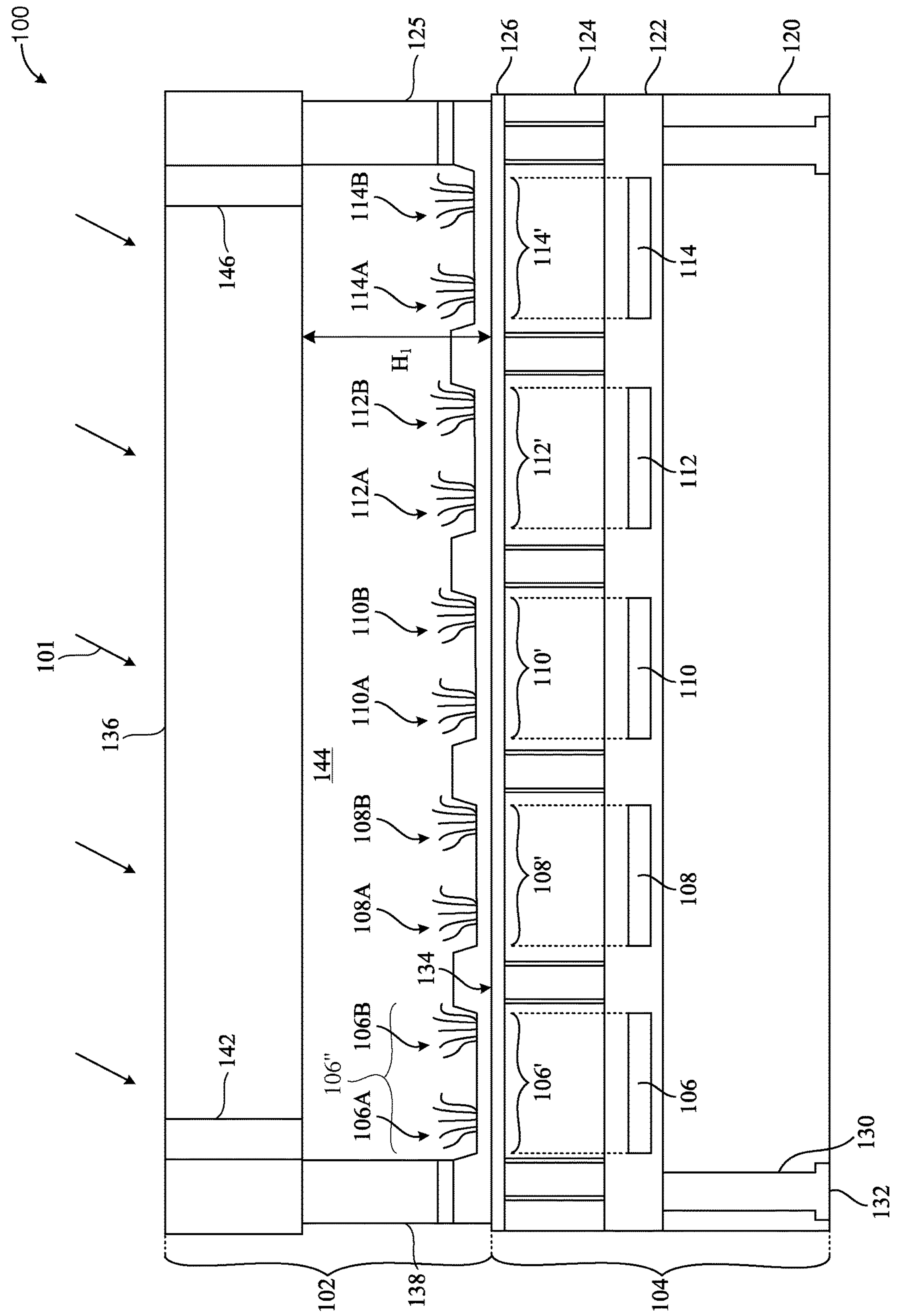
FIG. 1 illustrates a cross-section of a biosensor that can be used in various embodiments.

Embodiments described herein may be used in various biological or chemical processes and systems for academic or commercial analysis. More specifically, embodiments described herein may be used in various processes and systems where it is desired to detect an event, property, quality, or characteristic that is indicative of a desired reaction. For example, embodiments described herein include cartridges, biosensors, and their components as well as bioassay systems that operate with cartridges and biosensors. In particular embodiments, the cartridges and biosensors include a flow cell and one or more sensors, pixels, light detectors, or photodiodes that are coupled together in a substantially unitary structure.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be standalone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" or "including" an element or a plurality of elements having a particular property may include additional elements whether or not they have that property.

As used herein, a "desired reaction" includes a change in at least one of a chemical, electrical, physical, or optical property (or quality) of an analyte-of-interest. In particular embodiments, the desired reaction is a positive binding event (e.g., incorporation of a fluorescently labeled biomolecule with the analyte-of-interest). More generally, the desired reaction may be a chemical transformation, chemical change, or chemical interaction. The desired reaction may also be a change in electrical properties. For example, the desired reaction may be a change in ion concentration within a solution. Exemplary reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The desired reaction can also be an addition or elimination of a proton, for example, detectable as a change in pH of a surrounding solution or environment. An additional desired reaction can be detecting the flow of ions across a membrane (e.g., natural or synthetic bilayer membrane), for example as ions flow through a membrane the current is disrupted and the disruption can be detected.

In particular embodiments, the desired reaction includes the incorporation of a fluorescently-labeled molecule to an analyte. The analyte may be an oligonucleotide and the fluorescently-labeled molecule may be a nucleotide. The desired reaction may be detected when an excitation light is directed toward the oligonucleotide having the labeled nucleotide, and the fluorophore emits a detectable fluorescent signal. In alternative embodiments, the detected fluorescence is a result of chemiluminescence or bioluminescence. A desired reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" or "reactant" includes any substance that may be used to obtain a desired reaction. For example, reaction components include reagents, enzymes, samples, other biomolecules, and buffer solutions. The reaction components are typically delivered to a reaction site in a solution and/or immobilized at a reaction site. The reaction components may interact directly or indirectly with another substance, such as the analyte-of-interest.

As used herein, the term "reaction site" is a localized region where a desired reaction may occur. A reaction site may include support surfaces of a substrate where a substance may be immobilized thereon. For example, a reaction site may include a substantially planar surface in a channel of a flow cell that has a colony of nucleic acids thereon. Typically, but not always, the nucleic acids in the colony have the same sequence, being for example, clonal copies of a single stranded or double stranded template. However, in some embodiments a reaction site may contain only a single nucleic acid molecule, for example, in a single stranded or double stranded form. Furthermore, a plurality of reaction sites may be unevenly distributed along the support surface or arranged in a predetermined manner (e.g., side-by-side in a matrix, such as in microarrays). A reaction site can also include a reaction chamber (or well) that at least partially defines a spatial region or volume configured to compartmentalize the desired reaction.

This application uses the terms "reaction chamber" and "well" interchangeably. As used herein, the term "reaction chamber" or "well" includes a spatial region that is in fluid communication with a flow channel. The reaction chamber may be at least partially separated from the surrounding environment or other spatial regions. For example, a plurality of reaction chambers may be separated from each other by shared walls. As a more specific example, the reaction chamber may include a cavity defined by interior surfaces of a well and have an opening or aperture so that the cavity may be in fluid communication with a flow channel. Biosensors including such reaction chambers are described in greater detail in international application no. PCT/US2011/057111, filed on Oct. 20, 2011, which is incorporated herein by reference in its entirety.

In some embodiments, the reaction chambers are sized and shaped relative to solids (including semi-solids) so that the solids may be inserted, fully or partially, therein. For example, the reaction chamber may be sized and shaped to accommodate only one capture bead. The capture bead may have clonally amplified DNA or other substances thereon. Alternatively, the reaction chamber may be sized and shaped to receive an approximate number of beads or solid substrates. As another example, the reaction chambers may also be filled with a porous gel or substance that is configured to control diffusion or filter fluids that may flow into the reaction chamber.

In some embodiments, sensors (e.g., light detectors, photodiodes) are associated with corresponding pixel areas of a sample surface of a biosensor. As such, a pixel area is a geometrical construct that represents an area on the biosensor's sample surface for one sensor (or pixel). A sensor that is associated with a pixel area detects light emissions gathered from the associated pixel area when a desired reaction has occurred at a reaction site or a reaction chamber overlying the associated pixel area. In a flat surface embodiment, the pixel areas can overlap. In some cases, a plurality of sensors may be associated with a single reaction site or a single reaction chamber. In other cases, a single sensor may be associated with a group of reaction sites or a group of reaction chambers.

As used herein, a "biosensor" includes a structure having a plurality of reaction sites and/or reaction chambers (or wells). A biosensor may include a solid-state imaging device (e.g., CCD or CMOS imager) and, optionally, a flow cell mounted thereto. The flow cell may include at least one flow channel that is in fluid communication with the reaction sites and/or the reaction chambers. As one specific example, the biosensor is configured to fluidically and electrically couple to a bioassay system. The bioassay system may deliver reactants to the reaction sites and/or the reaction chambers according to a predetermined protocol (e.g., sequencing-by-synthesis) and perform a plurality of imaging events. For example, the bioassay system may direct solutions to flow along the reaction sites and/or the reaction chambers. At least one of the solutions may include four types of nucleotides having the same or different fluorescent labels. The nucleotides may bind to corresponding oligonucleotides located at the reaction sites and/or the reaction chambers. The bioassay system may then illuminate the reaction sites and/or the reaction chambers using an excitation light source (e.g., solid-state light sources, such as light-emitting diodes or LEDs). The excitation light may have a predetermined wavelength or wavelengths, including a range of wavelengths. The excited fluorescent labels provide emission signals that may be captured by the sensors.

In alternative embodiments, the biosensor may include electrodes or other types of sensors configured to detect other identifiable properties. For example, the sensors may be configured to detect a change in ion concentration. In another example, the sensors may be configured to detect the ion current flow across a membrane.

As used herein, a "cluster" is a colony of similar or identical molecules or nucleotide sequences or DNA strands. For example, a cluster can be an amplified oligonucleotide or any other group of a polynucleotide or polypeptide with a same or similar sequence. In other embodiments, a cluster can be any element or group of elements that occupy a physical area on a sample surface. In embodiments, clusters are immobilized to a reaction site and/or a reaction chamber during a base calling cycle.

As used herein, the term "immobilized," when used with respect to a biomolecule or biological or chemical substance, includes substantially attaching the biomolecule or biological or chemical substance at a molecular level to a surface. For example, a biomolecule or biological or chemical substance may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to a surface of a substrate material may be based upon the properties of the substrate surface, the liquid medium carrying the biomolecule or biological or chemical substance, and the properties of the biomolecules or biological or chemical substances themselves. In some cases, a substrate surface may be functionalized (e.g., chemically or physically modified) to facilitate immobilizing the biomolecules (or biological or chemical substances) to the substrate surface. The substrate surface may be first modified to have functional groups bound to the surface. The functional groups may then bind to biomolecules or biological or chemical substances to immobilize them thereon. A substance can be immobilized to a surface via a gel, for example, as described in US Patent Publ. No. US 2011/0059865 A1, which is incorporated herein by reference.

In some embodiments, nucleic acids can be attached to a surface and amplified using bridge amplification. Useful bridge amplification methods are described, for example, in U.S. Pat. No. 5,641,658; WO 2007/010251, U.S. Pat. No. 6,090,592; U.S. Patent Publ. No. 2002/0055100 A1; U.S. Pat. No. 7,115,400; U.S. Patent Publ. No. 2004/0096853 A1; U.S. Patent Publ. No. 2004/0002090 A1; U.S. Patent Publ. No. 2007/0128624 A1; and U.S. Patent Publ. No. 2008/0009420 A1, each of which is incorporated herein in its entirety. Another useful method for amplifying nucleic acids on a surface is Rolling Circle Amplification (RCA), for example, using methods set forth in further detail below. In some embodiments, the nucleic acids can be attached to a surface and amplified using one or more primer pairs. For example, one of the primers can be in solution and the other primer can be immobilized on the surface (e.g., 5'-attached). By way of example, a nucleic acid molecule can hybridize to one of the primers on the surface followed by extension of the immobilized primer to produce a first copy of the nucleic acid. The primer in solution then hybridizes to the first copy of the nucleic acid which can be extended using the first copy of the nucleic acid as a template. Optionally, after the first copy of the nucleic acid is produced, the original nucleic acid molecule can hybridize to a second immobilized primer on the surface and can be extended at the same time or after the primer in solution is extended. In any embodiment, repeated rounds of extension (e.g., amplification) using the immobilized primer and primer in solution provide multiple copies of the nucleic acid.

In particular embodiments, the assay protocols executed by the systems and methods described herein include the use of natural nucleotides and also enzymes that are configured to interact with the natural nucleotides. Natural nucleotides include, for example, ribonucleotides (RNA) or deoxyribonucleotides (DNA). Natural nucleotides can be in the mono-, di-, or tri-phosphate form and can have a base selected from adenine (A), thymine (T), uracil (U), guanine (G) or cytosine (C). It will be understood however that non-natural nucleotides, modified nucleotides or analogs of the aforementioned nucleotides can be used. Some examples of useful non-natural nucleotides are set forth below in regard to reversible terminator-based sequencing by synthesis methods.

In embodiments that include reaction chambers, items or solid substances (including semi-solid substances) may be disposed within the reaction chambers. When disposed, the item or solid may be physically held or immobilized within the reaction chamber through an interference fit, adhesion, or entrapment. Exemplary items or solids that may be disposed within the reaction chambers include polymer beads, pellets, agarose gel, powders, quantum dots, or other solids that may be compressed and/or held within the reaction chamber. In particular embodiments, a nucleic acid superstructure, such as a DNA ball, can be disposed in or at a reaction chamber, for example, by attachment to an interior surface of the reaction chamber or by residence in a liquid within the reaction chamber. A DNA ball or other nucleic acid superstructure can be preformed and then disposed in or at the reaction chamber. Alternatively, a DNA ball can be synthesized in situ at the reaction chamber. A DNA ball can be synthesized by rolling circle amplification to produce a concatemer of a particular nucleic acid sequence and the concatemer can be treated with conditions that form a relatively compact ball. DNA balls and methods for their synthesis are described, for example in, U.S. Patent Publication Nos. 2008/0242560 A1 or 2008/0234136 A1, each of which is incorporated herein in its entirety. A substance that is held or disposed in a reaction chamber can be in a solid, liquid, or gaseous state.

As used herein, "base calling" identifies a nucleotide base in a nucleic acid sequence. Base calling refers to the process of determining a base call (A, C, G, T) for every cluster at a specific cycle. As an example, base calling can be performed utilizing four-channel, two-channel or one-channel methods and systems described in the incorporated materials of U.S. Patent Application Publication No. 2013/0079232. In particular embodiments, a base calling cycle is referred to as a "sampling event." In one dye and two-channel sequencing protocol, a sampling event comprises two illumination stages in time sequence, such that a pixel signal is generated at each stage. The first illumination stage induces illumination from a given cluster indicating nucleotide bases A and T in a AT pixel signal, and the second illumination stage induces illumination from a given cluster indicating nucleotide bases C and T in a CT pixel signal.

Biosensor

FIG. 1 illustrates a cross-section of a biosensor 100 that can be used in various embodiments. Biosensor 100 has pixel areas 106', 108', 110', 112', and 114' that can each hold more than one cluster during a base calling cycle (e.g., 2 clusters per pixel area). As shown, the biosensor 100 may include a flow cell 102 that is mounted onto a sampling device 104. In the illustrated embodiment, the flow cell 102 is affixed directly to the sampling device 104. However, in alternative embodiments, the flow cell 102 may be removably coupled to the sampling device 104. The sampling device 104 has a sample surface 134 that may be functionalized (e.g., chemically or physically modified in a suitable manner for conducting the desired reactions). For example, the sample surface 134 may be functionalized and may include a plurality of pixel areas 106', 108', 110', 112', and 114' that can each hold more than one cluster during a base calling cycle (e.g., each having a corresponding cluster pair 106A, 106B; 108A, 108B; 110A, 110B; 112A, 112B; and 114A, 114B immobilized thereto). Each pixel area is associated with a corresponding sensor (or pixel or photodiode) 106, 108, 110, 112, and 114, such that light received by the pixel area is captured by the corresponding sensor. A pixel area 106' can be also associated with a corresponding reaction site 106" on the sample surface 134 that holds a cluster pair, such that light emitted from the reaction site 106" is received by the pixel area 106' and captured by the corresponding sensor 106. As a result of this sensing structure, in the case in which two or more clusters are present in a pixel area of a particular sensor during a base calling cycle (e.g., each having a corresponding cluster pair), the pixel signal in that base calling cycle carries information based on all of the two or more clusters. As a result, signal processing as described herein is used to distinguish each cluster, where there are more clusters than pixel signals in a given sampling event of a particular base calling cycle.

In the illustrated embodiment, the flow cell 102 includes sidewalls 138, 125, and a flow cover 136 that is supported by the sidewalls 138, 125. The sidewalls 138, 125 are coupled to the sample surface 134 and extend between the flow cover 136 and the sidewalls 138, 125. In some embodiments, the sidewalls 138, 125 are formed from a curable adhesive layer that bonds the flow cover 136 to the sampling device 104.

The sidewalls 138, 125 are sized and shaped so that a flow channel 144 exists between the flow cover 136 and the sampling device 104. The flow cover 136 may include a material that is transparent to excitation light 101 propagating from an exterior of the biosensor 100 into the flow channel 144. In an example, the excitation light 101 approaches the flow cover 136 at a non-orthogonal angle.

Also shown, the flow cover 136 may include inlet and outlet ports 142, 146 that are configured to fluidically engage other ports (not shown). For example, the other ports may be from the cartridge or the workstation. The flow channel 144 is sized and shaped to direct a fluid along the sample surface 134. A height H1 and other dimensions of the flow channel 144 may be configured to maintain a substantially even flow of a fluid along the sample surface 134. The dimensions of the flow channel 144 may also be configured to control bubble formation.

By way of example, the flow cover 136 (or the flow cell 102) may comprise a transparent material, such as glass or plastic. The flow cover 136 may constitute a substantially rectangular block having a planar exterior surface and a planar inner surface that defines the flow channel 144. The block may be mounted onto the sidewalls 138, 125. Alternatively, the flow cell 102 may be etched to define the flow cover 136 and the sidewalls 138, 125. For example, a recess may be etched into the transparent material. When the etched material is mounted to the sampling device 104, the recess may become the flow channel 144.

The sampling device 104 may be similar to, for example, an integrated circuit comprising a plurality of stacked substrate layers 120-126. The substrate layers 120-126 may include a base substrate 120, a solid-state imager 122 (e.g., CMOS image sensor), a filter or light-management layer 124, and a passivation layer 126. It should be noted that the above is only illustrative and that other embodiments may include fewer or additional layers. Moreover, each of the substrate layers 120-126 may include a plurality of sublayers. The sampling device 104 may be manufactured using processes that are similar to those used in manufacturing integrated circuits, such as CMOS image sensors and CCDs. For example, the substrate layers 120-126 or portions thereof may be grown, deposited, etched, and the like to form the sampling device 104.

The passivation layer 126 is configured to shield the filter layer 124 from the fluidic environment of the flow channel 144. In some cases, the passivation layer 126 is also configured to provide a solid surface (i.e., the sample surface 134) that permits biomolecules or other analytes-of-interest to be immobilized thereon. For example, each of the reaction sites may include a cluster of biomolecules that are immobilized to the sample surface 134. Thus, the passivation layer 126 may be formed from a material that permits the reaction sites to be immobilized thereto. The passivation layer 126 may also comprise a material that is at least transparent to a desired fluorescent light. By way of example, the passivation layer 126 may include silicon nitride (Si2N4) and/or silica (SiO2). However, other suitable material(s) may be used. In the illustrated embodiment, the passivation layer 126 may be substantially planar. However, in alternative embodiments, the passivation layer 126 may include recesses, such as pits, wells, grooves, and the like. In the illustrated embodiment, the passivation layer 126 has a thickness that is about 150-200 nm and, more particularly, about 170 nm.

The filter layer 124 may include various features that affect the transmission of light. In some embodiments, the filter layer 124 can perform multiple functions. For instance, the filter layer 124 may be configured to (a) filter unwanted light signals, such as light signals from an excitation light source; (b) direct emission signals from the reaction sites toward corresponding sensors 106, 108, 110, 112, and 114 that are configured to detect the emission signals from the reaction sites; or (c) block or prevent detection of unwanted emission signals from adjacent reaction sites. As such, the filter layer 124 may also be referred to as a light-management layer. In the illustrated embodiment, the filter layer 124 has a thickness that is about 1-5 μm and, more particularly, about 2-4 μm. In alternative embodiments, the filter layer 124 may include an array of microlenses or other optical components. Each of the microlenses may be configured to direct emission signals from an associated reaction site to a sensor.

In some embodiments, the solid-state imager 122 and the base substrate 120 may be provided together as a previously constructed solid-state imaging device (e.g., CMOS chip). For example, the base substrate 120 may be a wafer of silicon and the solid-state imager 122 may be mounted thereon. The solid-state imager 122 includes a layer of semiconductor material (e.g., silicon) and the sensors 106, 108, 110, 112, and 114. In the illustrated embodiment, the sensors are photodiodes configured to detect light. In other embodiments, the sensors comprise light detectors. The solid-state imager 122 may be manufactured as a single chip through a CMOS-based fabrication processes.

The solid-state imager 122 may include a dense array of sensors 106, 108, 110, 112, and 114 that are configured to detect activity indicative of a desired reaction from within or along the flow channel 144. In some embodiments, each sensor has a pixel area (or detection area) that is about 1-2 square micrometer ($\mu m^2$). The array can include 500,000 sensors, 5 million sensors, 10 million sensors, or even 120 million sensors. The sensors 106, 108, 110, 112, and 114 can be configured to detect a predetermined wavelength of light that is indicative of the desired reactions.

In some embodiments, the sampling device 104 includes a microcircuit arrangement, such as the microcircuit arrangement described in U.S. Pat. No. 7,595,882, which is incorporated herein by reference in the entirety. More specifically, the sampling device 104 may comprise an integrated circuit having a planar array of the sensors 106, 108, 110, 112, and 114. Circuitry formed within the sampling device 104 may be configured for at least one of signal amplification, digitization, storage, and processing. The circuitry may collect and analyze the detected fluorescent light and generate pixel signals (or detection signals) for communicating detection data to a signal processor. The circuitry may also perform additional analog and/or digital signal processing in the sampling device 104. Sampling device 104 may include conductive vias 130 that perform signal routing (e.g., transmit the pixel signals to the signal processor). The pixel signals may also be transmitted through electrical contacts 132 of the sampling device 104.

The sampling device 104 is discussed in further details with respect to U.S. Nonprovisional patent application Ser. No. 16/874,599, titled "Systems and Devices for Characterization and Performance Analysis of Pixel-Based Sequencing," filed May 14, 2020, which is incorporated by reference as if fully set forth herein. The sampling device 104 is not limited to the above constructions or uses as described above. In alternative embodiments, the sampling device 104 may take other forms. For example, the sampling device 104 may comprise a CCD device, such as a CCD camera, that is coupled to a flow cell or is moved to interface with a flow cell having reaction sites therein.

Figure 2:
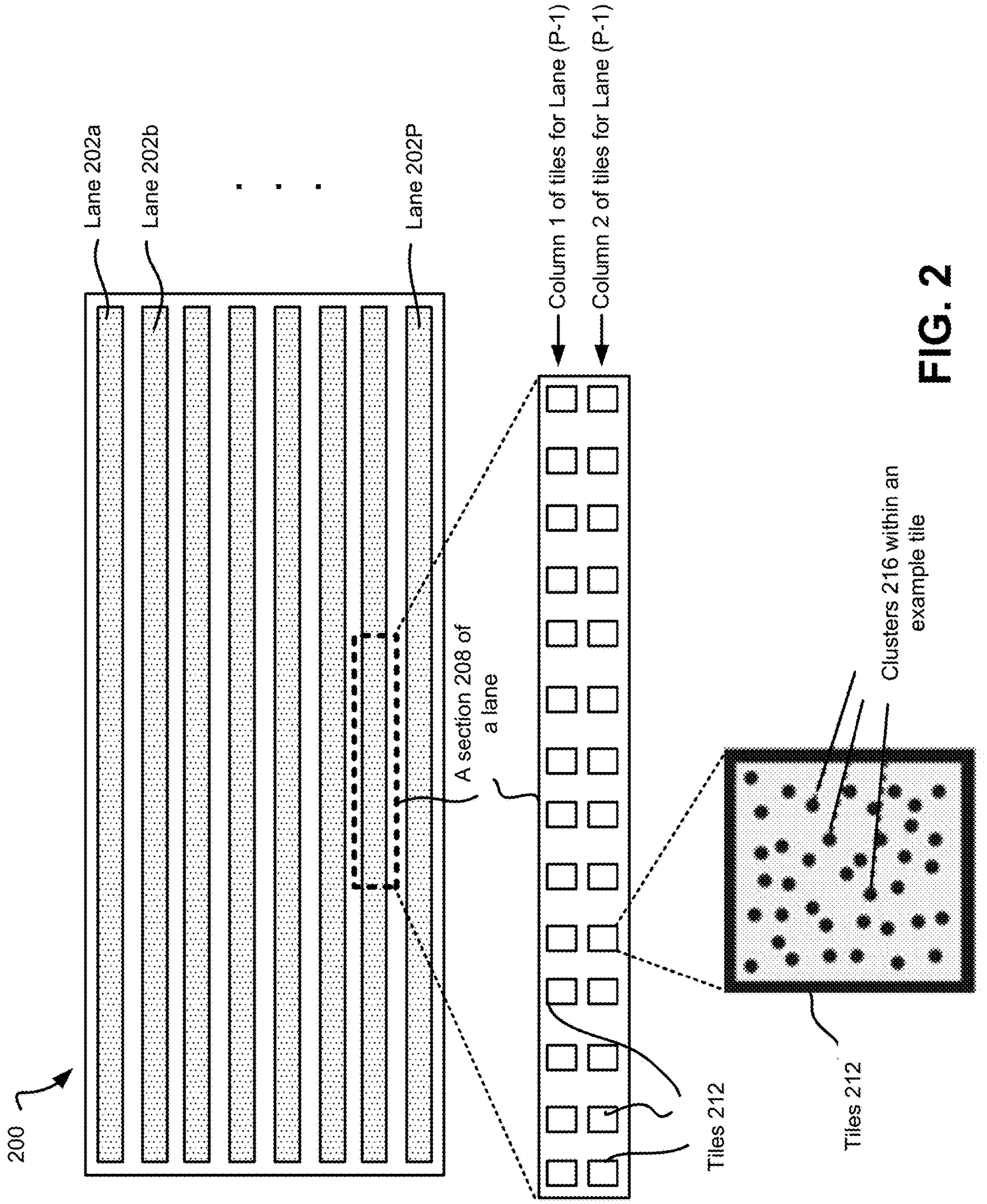
FIG. 2 depicts one implementation of a flow cell that contains clusters in its tiles.

FIG. 2 depicts one implementation of a flow cell 200 that contains clusters in its tiles. The flow cell 200 corresponds to the flow cell 102 of FIG. 1, e.g., without the flow cover 136. Furthermore, the depiction of the flow cell 200 is symbolic in nature, and the flow cell 200 symbolically depicts various lanes and tiles therewithin, without illustrating various other components therewithin. FIG. 2 illustrates a top view of the flow cell 200.

In an embodiment, the flow cell 200 is divided or partitioned in a plurality of lanes, such as lanes 202*a*, 202*b*, . . . , 202P, i.e., P number of lanes. In the example of FIG. 2, the flow cell 200 is illustrated to include 8 lanes, i.e., P=8 in this example, although the number of lanes within a flow cell is implementation specific.

In an embodiment, individual lanes 202 are further partitioned into non-overlapping regions called "tiles" 212. For example, FIG. 2 illustrates a magnified view of a section 208 of an example lane. The section 208 is illustrated to comprise a plurality of tiles 212.

In an example, each lane 202 comprises one or more columns of tiles. For example, in FIG. 2, each lane 202 comprises two corresponding columns of tiles 212, as illustrated within the magnified section 208. A number of tiles within each column of tiles within each lane is implementation specific, and in one example, there can be 50 tiles, 60 tiles, 100 tiles, or another appropriate number of tiles in each column of tiles within each lane.

Each tile comprises a corresponding plurality of clusters. During the sequencing procedure, the clusters and their surrounding background on the tiles are imaged. For example, FIG. 2 illustrates example clusters 216 within an example tile.

Figure 3:
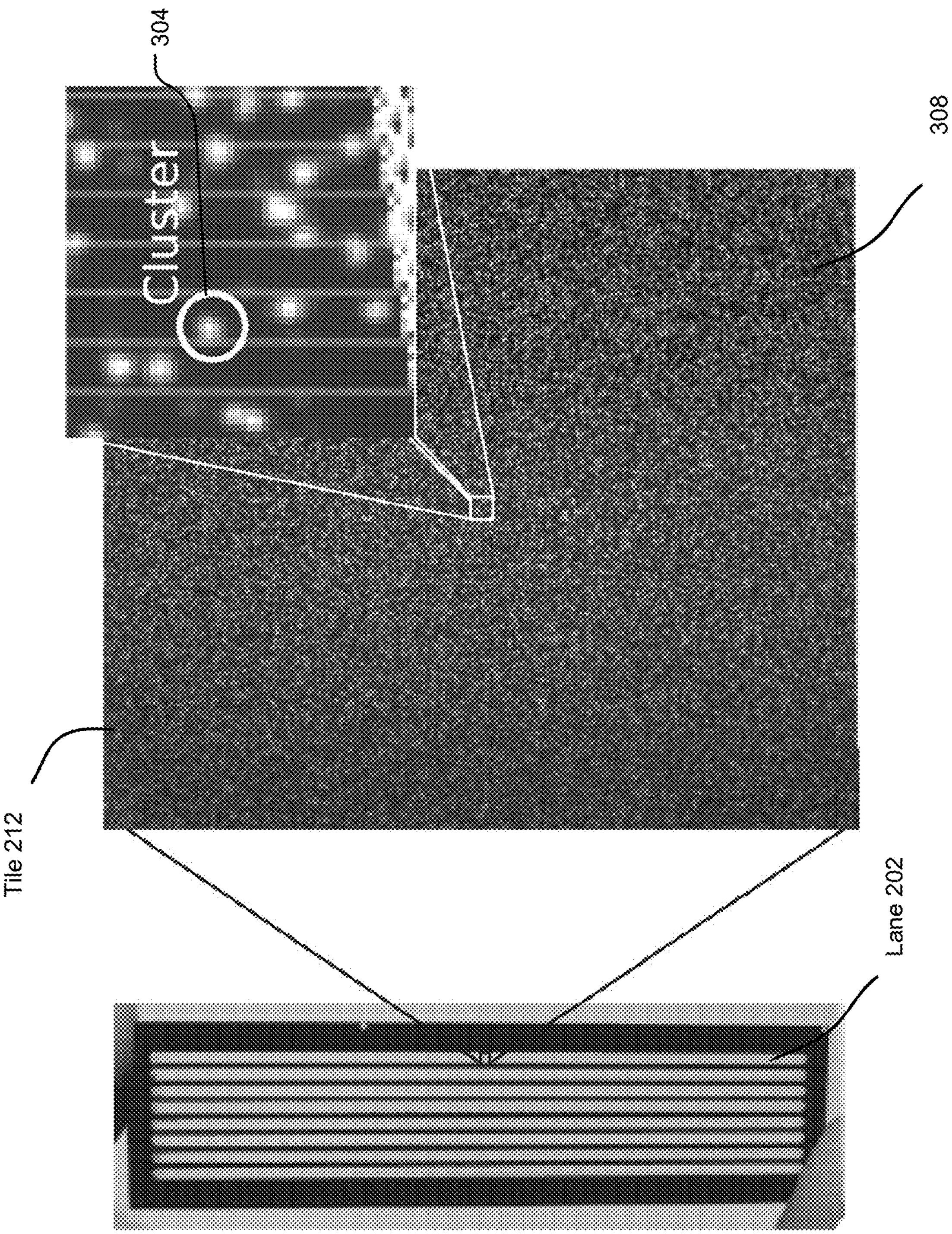
FIG. 3 illustrates an example flow cell with eight lanes, and also illustrates a zoom-in on one tile and its clusters and their surrounding background.

FIG. 3 illustrates an example Illumina GA-IIx™ flow cell with eight lanes, and also illustrates a zoom-in on one tile and its clusters and their surrounding background. For example, there are a hundred tiles per lane in Illumina Genome Analyzer II and sixty-eight tiles per lane in Illumina HiSeq2000. A tile 212 holds hundreds of thousands to millions of clusters. In FIG. 3, an image generated from a tile with clusters shown as bright spots is shown at 308 (e.g., 308 is a magnified image view of a tile), with an example cluster 304 labelled. A cluster 304 comprises approximately one thousand identical copies of a template molecule, though clusters vary in size and shape. The clusters are grown from the template molecule, prior to the sequencing run, by bridge amplification of the input library. The purpose of the amplification and cluster growth is to increase the intensity of the emitted signal since the imaging device cannot reliably sense a single fluorophore. However, the physical distance of the DNA fragments within a cluster 304 is small, so the imaging device perceives the cluster of fragments as a single spot.

Figure 4:
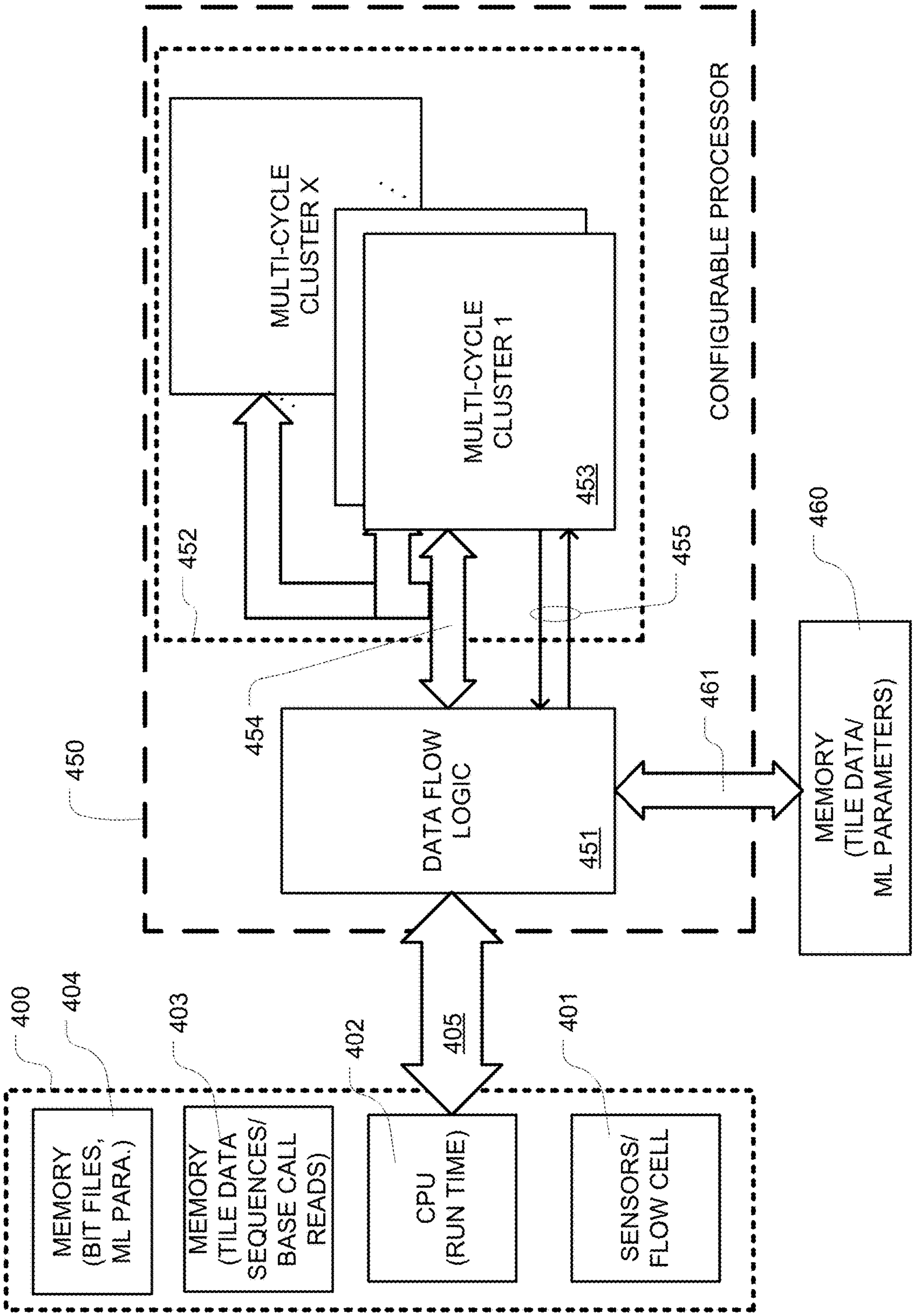
FIG. 4 is a simplified block diagram of the system for analysis of sensor data from a sequencing system, such as base call sensor outputs.

The clusters and the tiles are discussed in further details with respect to U.S. Nonprovisional patent application Ser. No. 16/825,987, titled "TRAINING DATA GENERATION FOR ARTIFICIAL INTELLIGENCE-BASED SEQUENCING," filed 20 Mar. 2020;

FIG. 4 is a simplified block diagram of the system for analysis of sensor data from a sequencing system, such as base call sensor outputs (e.g., see FIG. 1). In the example of FIG. 4, the system includes a sequencing machine 400 and a configurable processor 450. The configurable processor 450 can execute a neural network-based base caller in coordination with a runtime program executed by a host processor, such as a central processing unit (CPU) 402. The sequencing machine 400 comprises base call sensors and flow cell 401 (e.g., discussed with respect to FIGS. 1-3). The flow cell can comprise one or more tiles in which clusters of genetic material are exposed to a sequence of analyte flows used to cause reactions in the clusters to identify the bases in the genetic material, as discussed with respect to FIGS. 1-3. The sensors sense the reactions for each cycle of the sequence in each tile of the flow cell to provide tile data. Examples of this technology are described in more detail below. Genetic sequencing is a data intensive operation, which translates base call sensor data into sequences of base calls for each cluster of genetic material sensed in during a base call operation.

The system in this example includes the CPU 402 which executes a runtime program to coordinate the base call operations, memory 403 to store sequences of arrays of tile data, base call reads produced by the base calling operation, and other information used in the base call operations. Also, in this illustration the system includes memory 404 to store a configuration file (or files), such as FPGA bit files, and model parameters for the neural network used to configure and reconfigure the configurable processor 450 and execute the neural network. The sequencing machine 400 can include a program for configuring a configurable processor and in some embodiments a reconfigurable processor to execute the neural network.

The sequencing machine 400 is coupled by a bus 405 to the configurable processor 450. The bus 405 can be implemented using a high throughput technology, such as in one example bus technology compatible with the PCIe standards (Peripheral Component Interconnect Express) currently maintained and developed by the PCI-SIG (PCI Special Interest Group). Also, in this example, a memory 460 is coupled to the configurable processor 450 by bus 461. The memory 460 can be on-board memory, disposed on a circuit board with the configurable processor 450. The memory 460 is used for high-speed access by the configurable processor 450 of working data used in the base call operation. The bus 461 can also be implemented using a high throughput technology, such as bus technology compatible with the PCIe standards.

Configurable processors, including Field Programmable Gate Arrays (FPGAs), Coarse Grained Reconfigurable Arrays (CGRAs), and other configurable and reconfigurable devices, can be configured to implement a variety of functions more efficiently or faster than might be achieved using a general-purpose processor executing a computer program. Configuration of configurable processors involves compiling a functional description to produce a configuration file, referred to sometimes as a bitstream or bit file, and distributing the configuration file to the configurable elements on the processor.

The configuration file defines the logic functions to be executed by the configurable processor, by configuring the circuit to set data flow patterns, use of distributed memory and other on-chip memory resources, lookup table contents, operations of configurable logic blocks and configurable execution units like multiply-and-accumulate units, configurable interconnects and other elements of the configurable array. A configurable processor is reconfigurable if the configuration file may be changed in the field, by changing the loaded configuration file. For example, the configuration file may be stored in volatile SRAM elements, in non-volatile read-write memory elements, and in combinations of the same, distributed among the array of configurable elements on the configurable or reconfigurable processor. A variety of commercially available configurable processors are suitable for use in a base calling operation as described herein. Examples include commercially available products such as Xilinx Alveo™ U200, Xilinx Alveo™ U250, Xilinx Alveo™ U280, Intel/Altera Stratix™ GX2800, Intel/Altera Stratix™ GX2800, and Intel Stratix™ GX10M. In some examples, a host CPU can be implemented on the same integrated circuit as the configurable processor.

Embodiments described herein implement the multi-cycle neural network using a configurable processor 450. The configuration file for a configurable processor can be implemented by specifying the logic functions to be executed using a high-level description language (HDL) or a register transfer level (RTL) language specification. The specification can be compiled using the resources designed for the selected configurable processor to generate the configuration file. The same or similar specification can be compiled for the purposes of generating a design for an application-specific integrated circuit which may not be a configurable processor.

Alternatives for the configurable processor, in all embodiments described herein, therefore include a configured processor comprising an application specific ASIC or special purpose integrated circuit or set of integrated circuits, or a system-on-a-chip SOC device, configured to execute a neural network based base call operation as described herein.

In general, configurable processors and configured processors described herein, as configured to execute runs of a neural network, are referred to herein as neural network processors.

The configurable processor 450 is configured in this example by a configuration file loaded using a program executed by the CPU 402, or by other sources, which configures the array of configurable elements on the configurable processor 450 to execute the base call function. In this example, the configuration includes data flow logic 451 which is coupled to the buses 405 and 461 and executes functions for distributing data and control parameters among the elements used in the base call operation.

Also, the configurable processor 450 is configured with base call execution logic 452 to execute a multi-cycle neural network. The logic 452 comprises a plurality of multi-cycle execution clusters (e.g., 453) which, in this example, includes multi-cycle cluster 1 through multi-cycle cluster X. The number of multi-cycle clusters can be selected according to a trade-off involving the desired throughput of the operation, and the available resources on the configurable processor.

The multi-cycle clusters are coupled to the data flow logic 451 by data flow paths 454 implemented using configurable interconnect and memory resources on the configurable processor. Also, the multi-cycle clusters are coupled to the data flow logic 451 by control paths 455 implemented using configurable interconnect and memory resources for example on the configurable processor, which provide control signals indicating available clusters, readiness to provide input units for execution of a run of the neural network to the available clusters, readiness to provide trained parameters for the neural network, readiness to provide output patches of base call classification data, and other control data used for execution of the neural network.

The configurable processor is configured to execute runs of a multi-cycle neural network using trained parameters to produce classification data for sensing cycles of the base flow operation. A run of the neural network is executed to produce classification data for a subject sensing cycle of the base call operation. A run of the neural network operates on a sequence including a number N of arrays of tile data from respective sensing cycles of N sensing cycles, where the N sensing cycles provide sensor data for different base call operations for one base position per operation in time sequence in the examples described herein. Optionally, some of the N sensing cycles can be out of sequence if the needed according to a particular neural network model being executed. The number N can be any number greater than one. In some examples described herein, sensing cycles of the N sensing cycles represent a set of sensing cycles for at least one sensing cycle preceding the subject sensing cycle and at least one sensing cycle following the subject cycle in time sequence. Examples are described herein in which the number N is an integer equal to or greater than five.

The data flow logic 451 is configured to move tile data and at least some trained parameters of the model from the memory 460 to the configurable processor for runs of the neural network, using input units for a given run including tile data for spatially aligned patches of the N arrays. The input units can be moved by direct memory access operations in one DMA operation, or in smaller units moved during available time slots in coordination with the execution of the neural network deployed.

Tile data for a sensing cycle as described herein can comprise an array of sensor data having one or more features. For example, the sensor data can comprise two images which are analyzed to identify one of four bases at a base position in a genetic sequence of DNA, RNA, or other genetic material. The tile data can also include metadata about the images and the sensors. For example, in embodiments of the base calling operation, the tile data can comprise information about alignment of the images with the clusters such as distance from center information indicating the distance of each pixel in the array of sensor data from the center of a cluster of genetic material on the tile.

During execution of the multi-cycle neural network as described below, tile data can also include data produced during execution of the multi-cycle neural network, referred to as intermediate data, which can be reused rather than recomputed during a run of the multi-cycle neural network. For example, during execution of the multi-cycle neural network, the data flow logic can write intermediate data to the memory 460 in place of the sensor data for a given patch of an array of tile data. Embodiments like this are described in more detail below.

As illustrated, a system is described for analysis of base call sensor output, comprising memory (e.g., 460) accessible by the runtime program storing tile data including sensor data for a tile from sensing cycles of a base calling operation. Also, the system includes a neural network processor, such as configurable processor 450 having access to the memory. The neural network processor is configured to execute runs of a neural network using trained parameters to produce classification data for sensing cycles. As described herein, a run of the neural network is operating on a sequence of N arrays of tile data from respective sensing cycles of N sensing cycles, including a subject cycle, to produce the classification data for the subject cycle. The data flow logic 451 is provided to move tile data and the trained parameters from the memory to the neural network processor for runs of the neural network using input units including data for spatially aligned patches of the N arrays from respective sensing cycles of N sensing cycles.

Also, a system is described in which the neural network processor has access to the memory, and includes a plurality of execution clusters, the execution logic clusters in the plurality of execution clusters configured to execute a neural network. The data flow logic has access to the memory and to execution clusters in the plurality of execution clusters, to provide input units of tile data to available execution clusters in the plurality of execution clusters, the input units including a number N of spatially aligned patches of arrays of tile data from respective sensing cycles, including a subject sensing cycle, and to cause the execution clusters to apply the N spatially aligned patches to the neural network to produce output patches of classification data for the spatially aligned patch of the subject sensing cycle, where N is greater than 1.

Figure 5:
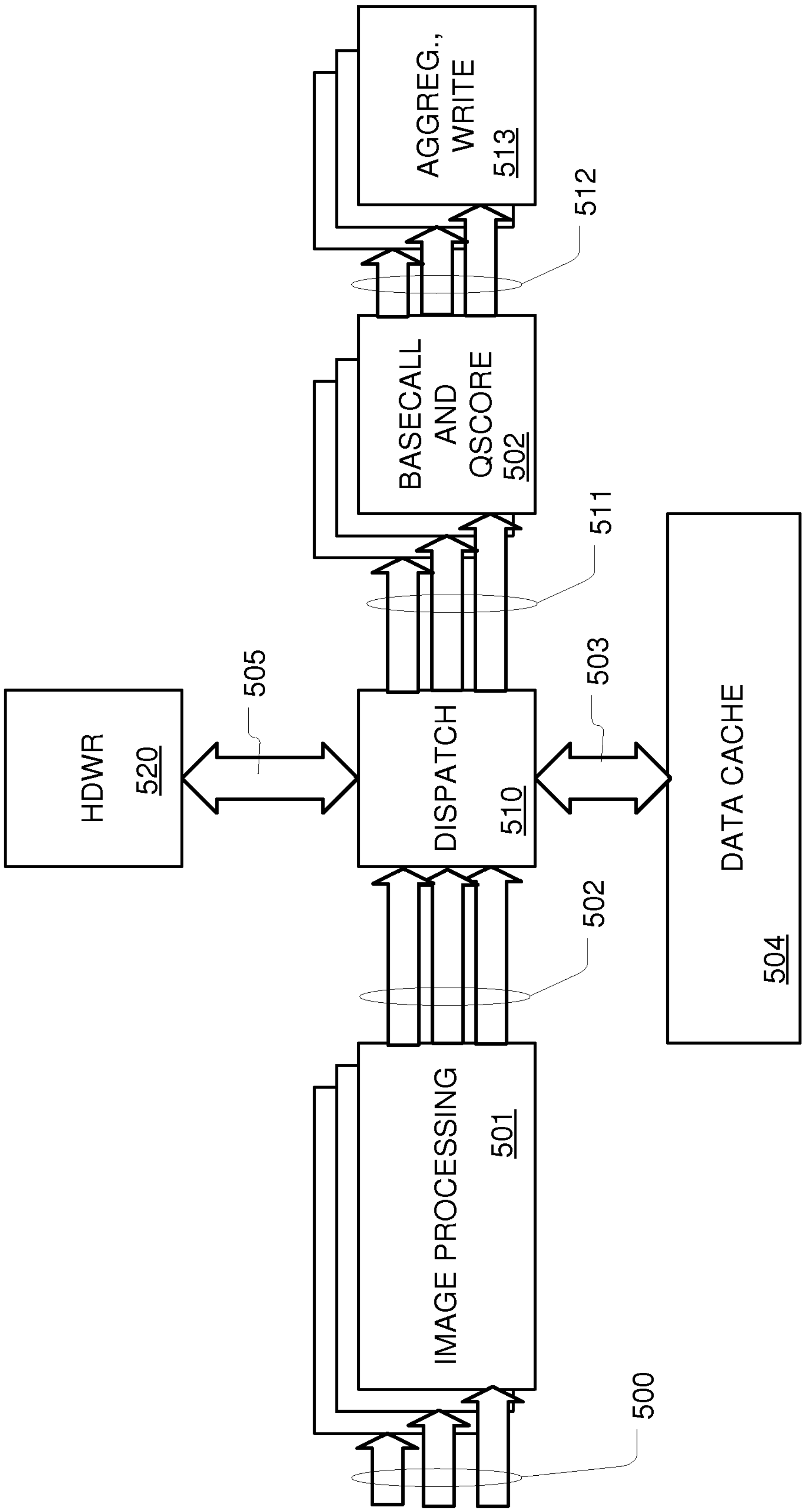
FIG. 5 is a simplified diagram showing aspects of the base calling operation, including functions of a runtime program executed by a host processor.

FIG. 5 is a simplified diagram showing aspects of the base calling operation, including functions of a runtime program executed by a host processor. In this diagram, the output of image sensors from a flow cell (such as those illustrated in FIGS. 1-2) are provided on lines 500 to image processing threads 501, which can perform processes on images such as resampling, alignment and arrangement in an array of sensor data for the individual tiles, and can be used by processes which calculate a tile cluster mask for each tile in the flow cell, which identifies pixels in the array of sensor data that correspond to clusters of genetic material on the corresponding tile of the flow cell. To compute a cluster mask, one example algorithm is based on a process to detect clusters which are unreliable in the early sequencing cycles using a metric derived from the softmax output, and then the data from those wells/clusters is discarded, and no output data is produced for those clusters. For example, a process can identify clusters with high reliability during the first N1 (e.g., 25) base-calls, and reject the others. Rejected clusters might be polyclonal or very weak intensity or obscured by fiducials. This procedure can be performed on the host CPU. In alternative implementations, this information would potentially be used to identify the necessary clusters of interest to be passed back to the CPU, thereby limiting the storage required for intermediate data.

The outputs of the image processing threads 501 are provided on threads 502 to a dispatch logic 510 in the CPU which routes the arrays of tile data to a data cache 504 on a high-speed bus 503, or on high-speed bus 505 to the multi-cluster neural network processor hardware 520, such as the configurable processor of FIG. 4, according to the state of the base calling operation. The hardware 520 returns classification data output by the neural network to the dispatch logic 510, which passes the information to the data cache 504, or on lines 511 to threads 502 that perform base call and quality score computations using the classification data, and can arrange the data in standard formats for base call reads. The outputs of the threads 502 that perform base calling and quality score computations are provided on lines 512 to threads 513 that aggregate the base call reads, perform other operations such as data compression, and write the resulting base call outputs to specified destinations for utilization by the customers.

In some embodiments, the host can include threads (not shown) that perform final processing of the output of the hardware 520 in support of the neural network. For example, the hardware 520 can provide outputs of classification data from a final layer of the multi-cluster neural network. The host processor can execute an output activation function, such as a softmax function, over the classification data to configure the data for use by the base call and quality score threads 502. Also, the host processor can execute input operations (not shown), such as resampling, batch normalization or other adjustments of the tile data prior to input to the hardware 520.

Figure 6:
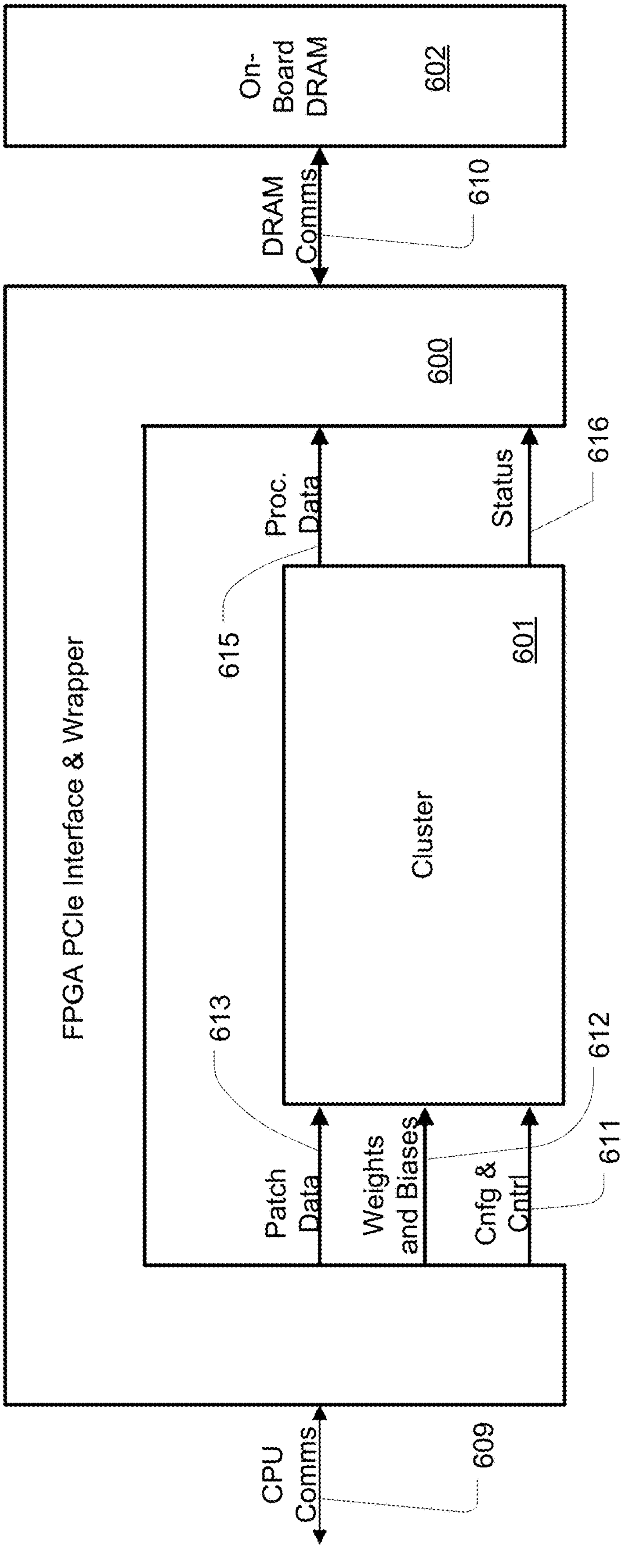
FIG. 6 is a simplified diagram of a configuration of a configurable processor such as that of FIG. 4.

FIG. 6 is a simplified diagram of a configuration of a configurable processor such as that of FIG. 4. In FIG. 6, the configurable processor comprises in FPGA with a plurality of high speed PCIe interfaces. The FPGA is configured with a wrapper 600 which comprises the data flow logic described with reference to FIG. 1. The wrapper 600 manages the interface and coordination with a runtime program in the CPU across the CPU communication link 609 and manages communication with the on-board DRAM 602 (e.g., memory 460) via DRAM communication link 610. The data flow logic in the wrapper 600 provides patch data retrieved by traversing the arrays of tile data on the on-board DRAM 602 for the number N cycles to a cluster 601 and retrieves process data 615 from the cluster 601 for delivery back to the on-board DRAM 602. The wrapper 600 also manages transfer of data between the on-board DRAM 602 and host memory, for both the input arrays of tile data, and for the output patches of classification data. The wrapper transfers patch data on line 613 to the allocated cluster 601. The wrapper provides trained parameters, such as weights and biases on line 612 to the cluster 601 retrieved from the on-board DRAM 602. The wrapper provides configuration and control data on line 611 to the cluster 601 provided from, or generated in response to, the runtime program on the host via the CPU communication link 609. The cluster can also provide status signals on line 616 to the wrapper 600, which are used in cooperation with control signals from the host to manage traversal of the arrays of tile data to provide spatially aligned patch data, and to execute the multi-cycle neural network over the patch data using the resources of the cluster 601.

As mentioned above, there can be multiple clusters on a single configurable processor managed by the wrapper 600 configured for executing on corresponding ones of multiple patches of the tile data. Each cluster can be configured to provide classification data for base calls in a subject sensing cycle using the tile data of multiple sensing cycles described herein.

In examples of the system, model data, including kernel data like filter weights and biases can be sent from the host CPU to the configurable processor, so that the model can be updated as a function of cycle number. A base calling operation can comprise, for a representative example, on the order of hundreds of sensing cycles. Base calling operation can include paired end reads in some embodiments. For example, the model trained parameters may be updated once every 20 cycles (or other number of cycles), or according to update patterns implemented for particular systems and neural network models. In some embodiments including paired end reads in which a sequence for a given string in a genetic cluster on a tile includes a first part extending from a first end down (or up) the string, and a second part extending from a second end up (or down) the string, the trained parameters can be updated on the transition from the first part to the second part.

In some examples, image data for multiple cycles of sensing data for a tile can be sent from the CPU to the wrapper 600. The wrapper 600 can optionally do some pre-processing and transformation of the sensing data and write the information to the on-board DRAM 602. The input tile data for each sensing cycle can include arrays of sensor data including on the order of 4000×3000 pixels per sensing cycle per tile or more, with two features representing colors of two images of the tile, and one or two bytes per feature per pixel. For an embodiment in which the number N is three sensing cycles to be used in each run of the multi-cycle neural network, the array of tile data for each run of the multi-cycle neural network can consume on the order of hundreds of megabytes per tile. In some embodiments of the system, the tile data also includes an array of DFC data, stored once per tile, or other type of metadata about the sensor data and the tiles.

In operation, when a multi-cycle cluster is available, the wrapper allocates a patch to the cluster. The wrapper fetches a next patch of tile data in the traversal of the tile and sends it to the allocated cluster along with appropriate control and configuration information. The cluster can be configured with enough memory on the configurable processor to hold a patch of data including patches from multiple cycles in some systems, that is being worked on in place, and a patch of data that is to be worked on when the current patch of processing is finished using a ping-pong buffer technique or raster scanning technique in various embodiments.

When an allocated cluster completes its run of the neural network for the current patch and produces an output patch, it will signal the wrapper. The wrapper will read the output patch from the allocated cluster, or alternatively the allocated cluster will push the data out to the wrapper. Then the wrapper will assemble output patches for the processed tile in the DRAM 602. When the processing of the entire tile has been completed, and the output patches of data transferred to the DRAM, the wrapper sends the processed output array for the tile back to the host/CPU in a specified format. In some embodiments, the on-board DRAM 602 is managed by memory management logic in the wrapper 600. The runtime program can control the sequencing operations to complete analysis of all the arrays of tile data for all the cycles in the run in a continuous flow to provide real time analysis.

Figure 7:
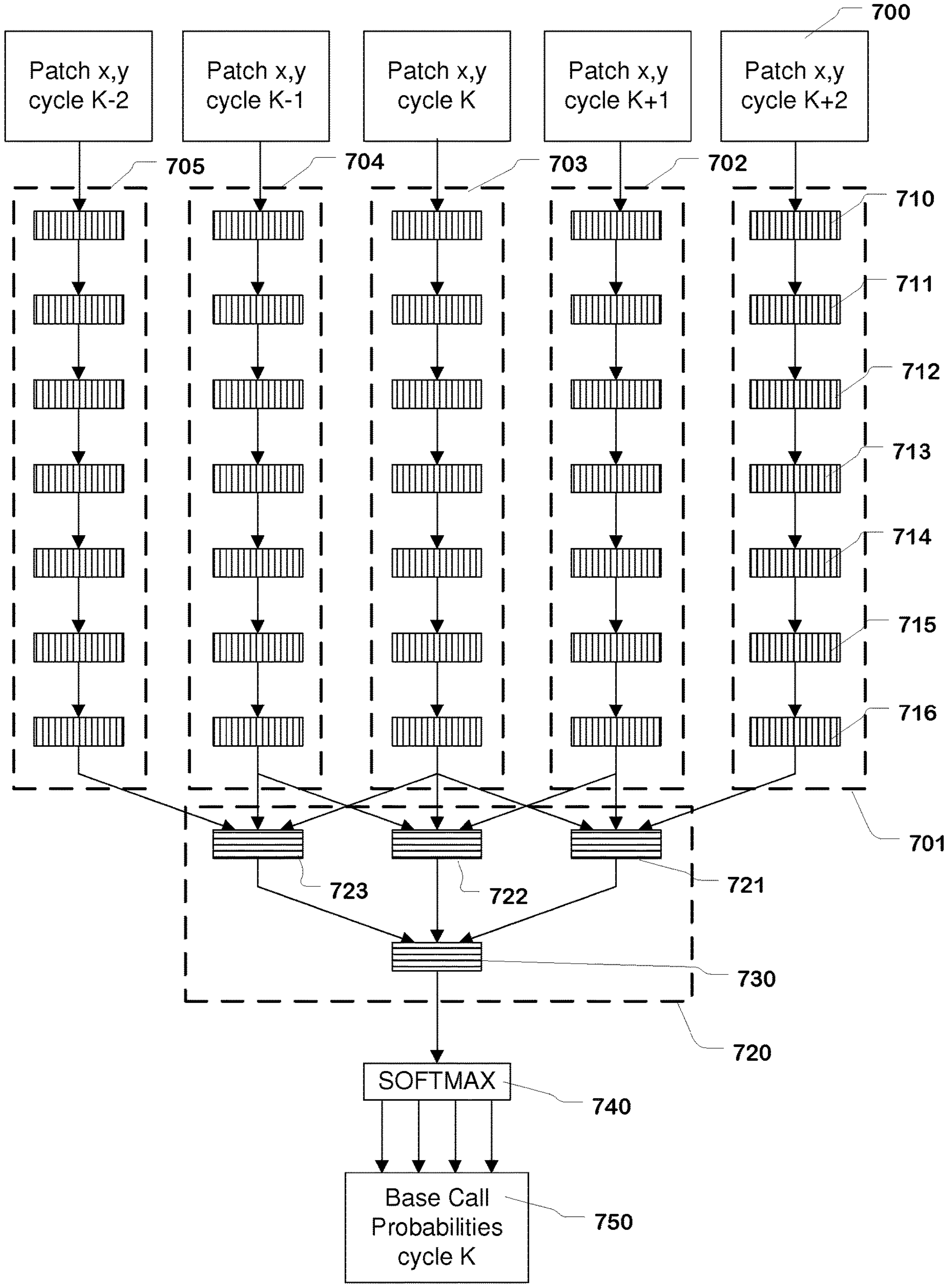
FIG. 7 is a diagram of a neural network architecture which can be executed using a configurable or a reconfigurable array configured as described herein.

FIG. 7 is a diagram of a multi-cycle neural network model which can be executed using the system described herein. The example shown in FIG. 7 can be referred to as a five-cycle input, one-cycle output neural network. The inputs to the multi-cycle neural network model include five spatially aligned patches (e.g., 700) from the tile data arrays of five sensing cycles of a given tile. Spatially aligned patches have the same aligned row and column dimensions (x,y) as other patches in the set, so that the information relates to the same clusters of genetic material on the tile in sequence cycles. In this example, a subject patch is a patch from the array of tile data for cycle K. The set of five spatially aligned patches includes a patch from cycle K−2 preceding the subject patch by two cycles, a patch from cycle K−1 preceding the subject patch by one cycle, a patch from cycle K+1 following the patch from the subject cycle by one cycle, and a patch from cycle K+2 following the patch from the subject cycle by two cycles.

The model includes a segregated stack 701 of layers of the neural network for each of the input patches. Thus, stack 701 receives as input, tile data for the patch from cycle K+2, and is segregated from the stacks 702, 703, 704, and 705 so they do not share input data or intermediate data. In some embodiments, all of the stacks 710-705 can have identical models, and identical trained parameters. In other embodiments, the models and trained parameters may be different in the different stacks. Stack 702 receives as input, tile data for the patch from cycle K+1. Stack 703 receives as input, tile data for the patch from cycle K. Stack 704 receives as input, tile data for the patch from cycle K−1. Stack 705 receives as input, tile data for the patch from cycle K−2. The layers of the segregated stacks each execute a convolution operation of a kernel including a plurality of filters over the input data for the layer. As in the example above, the patch 700 may include three features. The output of the layer 710 may include many more features, such as 10 to 20 features. Likewise, the outputs of each of layers 711 to 716 can include any number of features suitable for a particular implementation. The parameters of the filters are trained parameters for the neural network, such as weights and biases. The output feature set (intermediate data) from each of the stacks 701-705 is provided as input to an inverse hierarchy 720 of temporal combinatorial layers, in which the intermediate data from the multiple cycles is combined. In the example illustrated, the inverse hierarchy 720 includes a first layer including three combinatorial layers 721, 722, 723, each receiving intermediate data from three of the segregated stacks, and a final layer including one combinatorial layer 730 receiving intermediate data from the three temporal layers 721, 722, 723.

The output of the final combinatorial layer 730 is an output patch of classification data for clusters located in the corresponding patch of the tile from cycle K. The output patches can be assembled into an output array classification data for the tile for cycle K. In some embodiments, the output patch may have sizes and dimensions different from the input patches. In some embodiments, the output patch may include pixel-by-pixel data that can be filtered by the host to select cluster data.

The output classification data can then be applied to a softmax function 740 (or other output activation function) optionally executed by the host, or on the configurable processor, depending on the particular implementation. An output function different from softmax could be used (e.g., making a base call output parameter according to largest output, then use a learned nonlinear mapping using context/network outputs to give base quality).

Finally, the output of the softmax function 740 can be provided as base call probabilities for cycle K (750) and stored in host memory to be used in subsequent processing. Other systems may use another function for output probability calculation, e.g., another nonlinear model.

The neural network can be implemented using a configurable processor with a plurality of execution clusters so as complete evaluation of one tile cycle within the duration of the time interval, or close to the duration of the time interval, of one sensing cycle, effectively providing the output data in real time. Data flow logic can be configured to distribute input units of tile data and trained parameters to the execution clusters, and to distribute output patches for aggregation in memory.

Input units of data for a five-cycle input, one-cycle output neural network like that of FIG. 7 are described with reference to FIGS. 8A and 8B for a base call operation using two-channel sensor data. For example, for a given base in a genetic sequence, the base call operation can execute two flows of analyte and two reactions that generate two channels of signals, such as images, which can be processed to identify which one of four bases is located at a current position in the genetic sequence for each cluster of genetic material. In other systems, a different number of channels of sensing data may be utilized. For example, base calling can be performed utilizing one-channel methods and systems. Incorporated materials of U.S. Patent Application Publication No. 2013/0079232 discuss base calling using various number of channels, such as one-channel, two-channels, or four-channels.

Figure 8A:
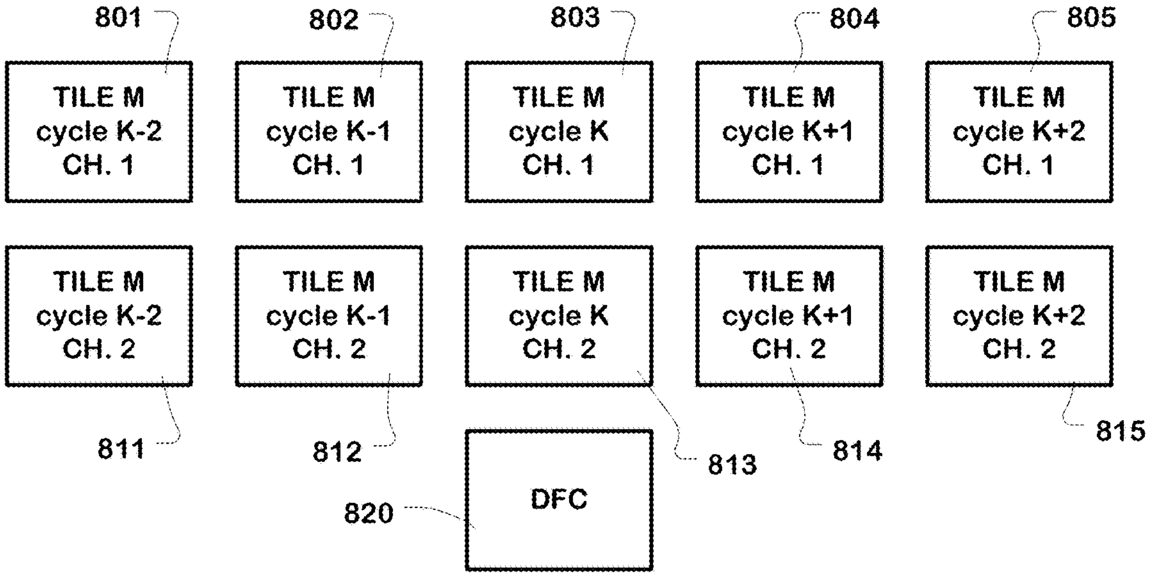
FIG. 8A is a simplified illustration of an organization of tiles of sensor data used by a neural network architecture like that of FIG. 7.

FIG. 8A shows arrays of tile data for five cycles for a given tile, tile M, used for the purposes of executing a five-cycle input, one-cycle output neural network. The five-cycle input tile data in this example can be written to the on-board DRAM, or other memory in the system which can be accessed by the data flow logic and, for cycle K−2, includes an array 801 for channel 1 and an array 811 for channel 2, for cycle K−1, an array 802 for channel 1 and an array 812 for channel 2, for cycle K, an array 803 for channel 1 and an array 813 for channel 2, for cycle K+1, an array 804 for channel 1 and an array 814 for channel 2, for cycle K+2, an array 805 for channel 1 and an array 815 for channel 2. Also an array 820 of metadata for the tile can be written once in the memory, in this case a DFC file, included for use as input to the neural network along with each cycle.

Although FIG. 8A discusses two-channel base calling operations, using two channels is merely an example, and base calling can be performed using any other appropriate number of channels. For example, incorporated materials of U.S. Patent Application Publication No. 2013/0079232 discuss base calling using various number of channels, such as one-channel, two-channels, or four-channels, or another appropriate number of channels.

Figure 8B:
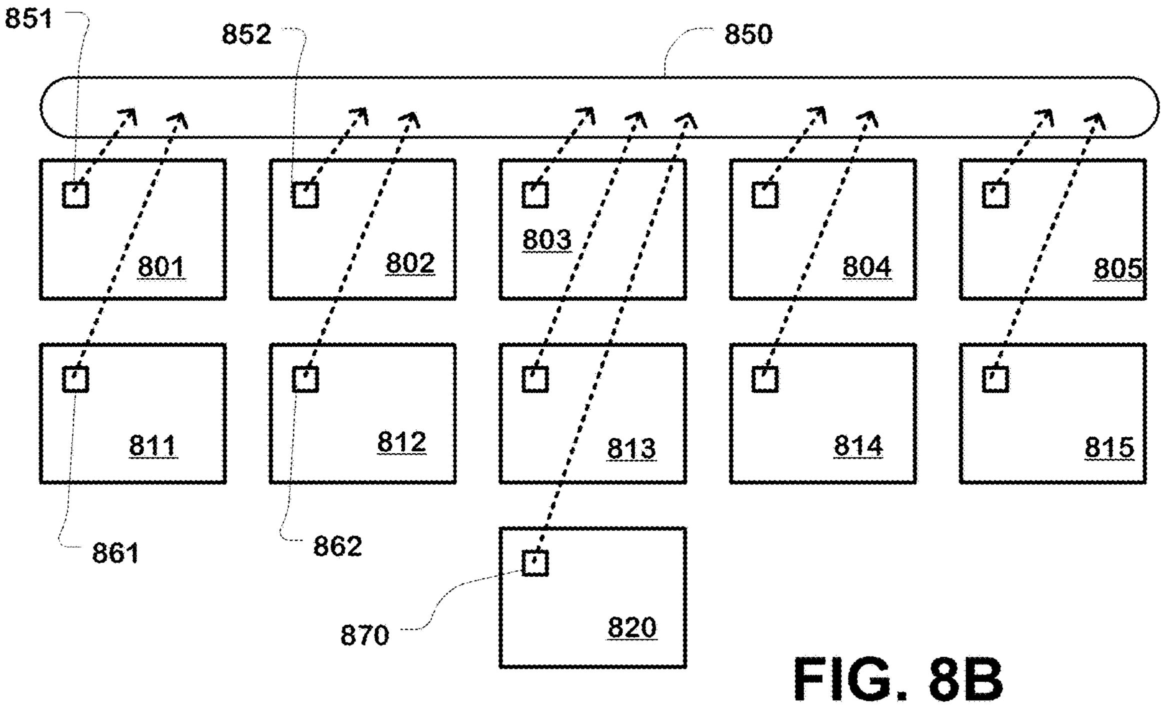
FIG. 8B is a simplified illustration of patches of tiles of sensor data used by a neural network architecture like that of FIG. 7.

The data flow logic composes input units, which can be understood with reference to FIG. 8B, of tile data that includes spatially aligned patches of the arrays of tile data for each execution cluster configured to execute a run of the neural network over an input patch. An input unit for an allocated execution cluster is composed by the data flow logic by reading spatially aligned patches (e.g., 851, 852, 861, 862, 870) from each of the arrays 801-805, 811, 815, 820 of tile data for the five input cycles, and delivering them via data paths (schematically 850) to memory on the configurable processor configured for use by the allocated execution cluster. The allocated execution cluster executes a run of the five-cycle input/one-cycle output neural network, and delivers an output patch for the subject cycle K of classification data for the same patch of the tile in the subject cycle K.

Figure 9:
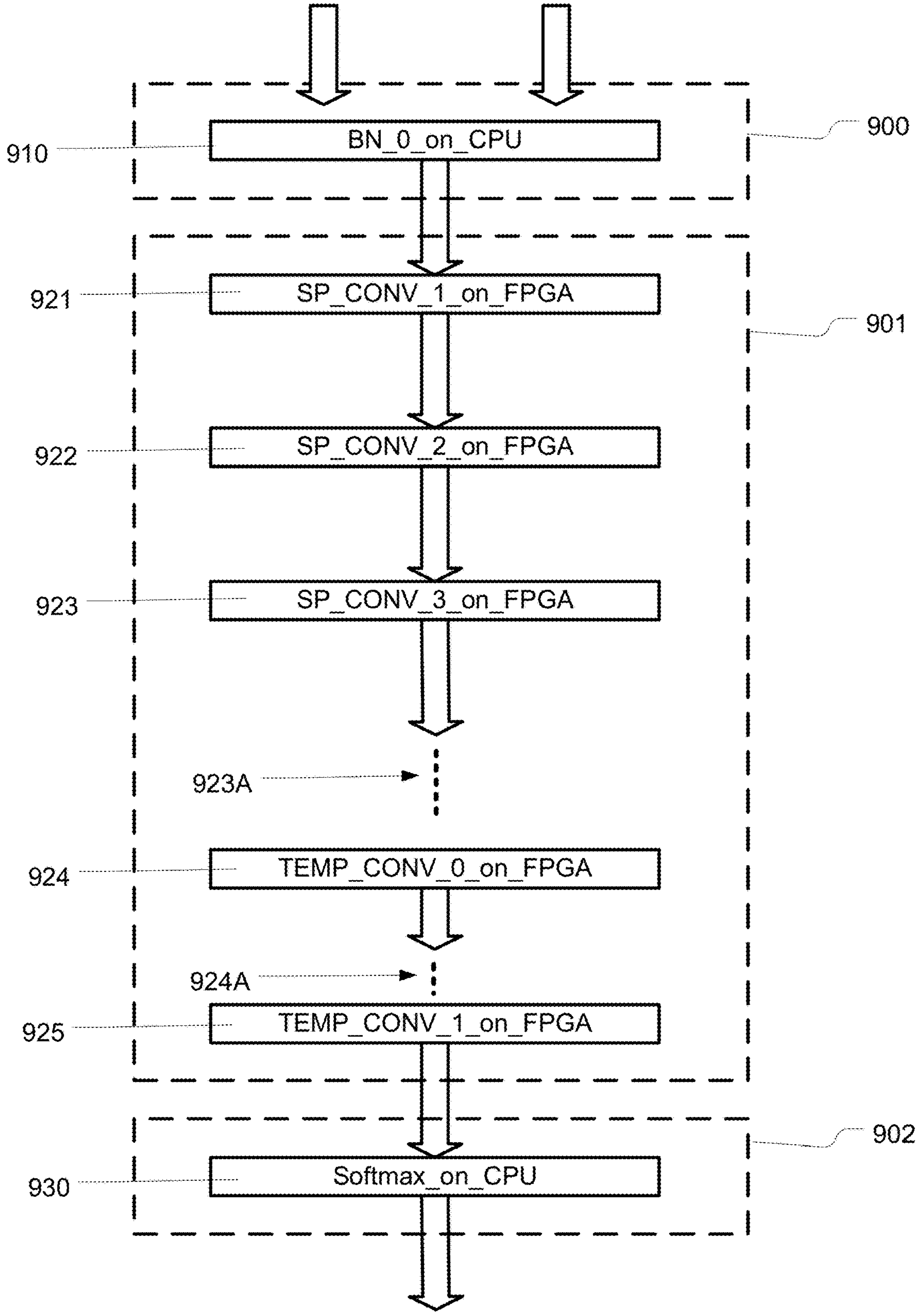
FIG. 9 illustrates part of a configuration for a neural network like that of FIG. 7 on a configurable or a reconfigurable array, such as a Field Programmable Gate Array (FPGA).

FIG. 9 is a simplified representation of a stack of a neural network usable in a system like that of FIG. 7 (e.g., 701 and 720). In this example, some functions of the neural network (e.g., 900, 902) are executed on the host, and other portions of the neural network (e.g., 901) are executed on the configurable processor.

In an example, a first function can be batch normalization (layer 910) formed on the CPU. However, in another example, batch normalization as a function may be fused into one or more layers, and no separate batch normalization layer may be present.

A number of spatial, segregated convolution layers are executed as a first set of convolution layers of the neural network, as discussed above on the configurable processor. In this example, the first set of convolution layers applies 2D convolutions spatially.

As shown in FIG. 9, a first spatial convolution 921 is executed, followed by a second spatial convolution 922, followed by a third spatial convolution 923, and so on for a number L/2 of spatially segregated neural network layers in each stack (L is described with reference to FIG. 7). As indicated at 923A, the number of spatial layers can be any practical number, which for context may range from a few to more than 20 in different embodiments.

For SP_CONV_0, kernel weights are stored for example in a (1,6,6,3,L) structure since there are 3 input channels to this layer. In this example, the "6" in this structure is due to storing coefficients in the transformed Winograd domain (the kernel size is 3×3 in the spatial domain but expands in the transform domain).

For other SP_CONV layers, kernel weights are stored for this example in a (1,6,6 L) structure since there are K(=L) inputs and outputs for each of these layers.

The outputs of the stack of spatial layers are provided to temporal layers, including convolution layers 924, 925 executed on the FPGA. Layers 924 and 925 can be convolution layers applying 1D convolutions across cycles. As indicated at 924A, the number of temporal layers can be any practical number, which for context may range from a few to more than 20 in different embodiments.

The first temporal layer, TEMP_CONV_0 layer 824, reduces the number of cycle channels from 5 to 3, as illustrated in FIG. 7. The second temporal layer, layer 925, reduces the number of cycle channels from 3 to 1 as illustrated in FIG. 7, and reduces the number of feature maps to four outputs for each pixel, representing confidence in each base call.

The output of the temporal layers is accumulated in output patches and delivered to the host CPU to apply for example, a softmax function 930, or other function to normalize the base call probabilities.

Figure 10:
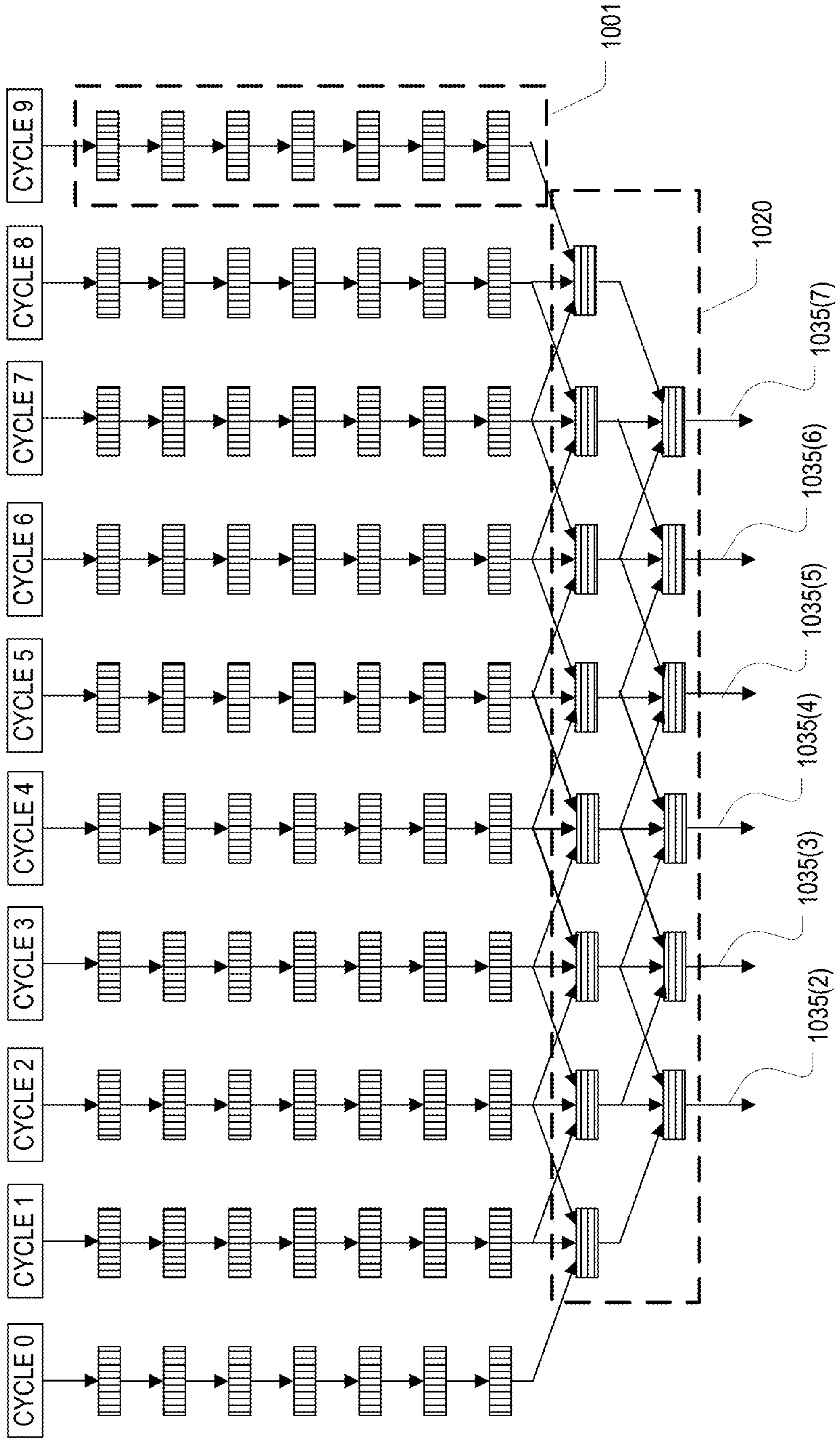
FIG. 10 is a diagram of another alternative neural network architecture which can be executed using a configurable or a reconfigurable array configured as described herein.

FIG. 10 illustrates an alternative implementation showing a 10-input, six-output neural network which can be executed for a base calling operation. In this example, tile data for spatially aligned input patches from cycles 0 to 9 are applied to segregated stacks of spatial layers, such as stack 1001 for cycle 9. The outputs of the segregated stacks are applied to an inverse hierarchical arrangement of temporal stacks 1020, having outputs 1035(2) through 1035(7) providing base call classification data for subject cycles 2 through 7.

Figure 11:
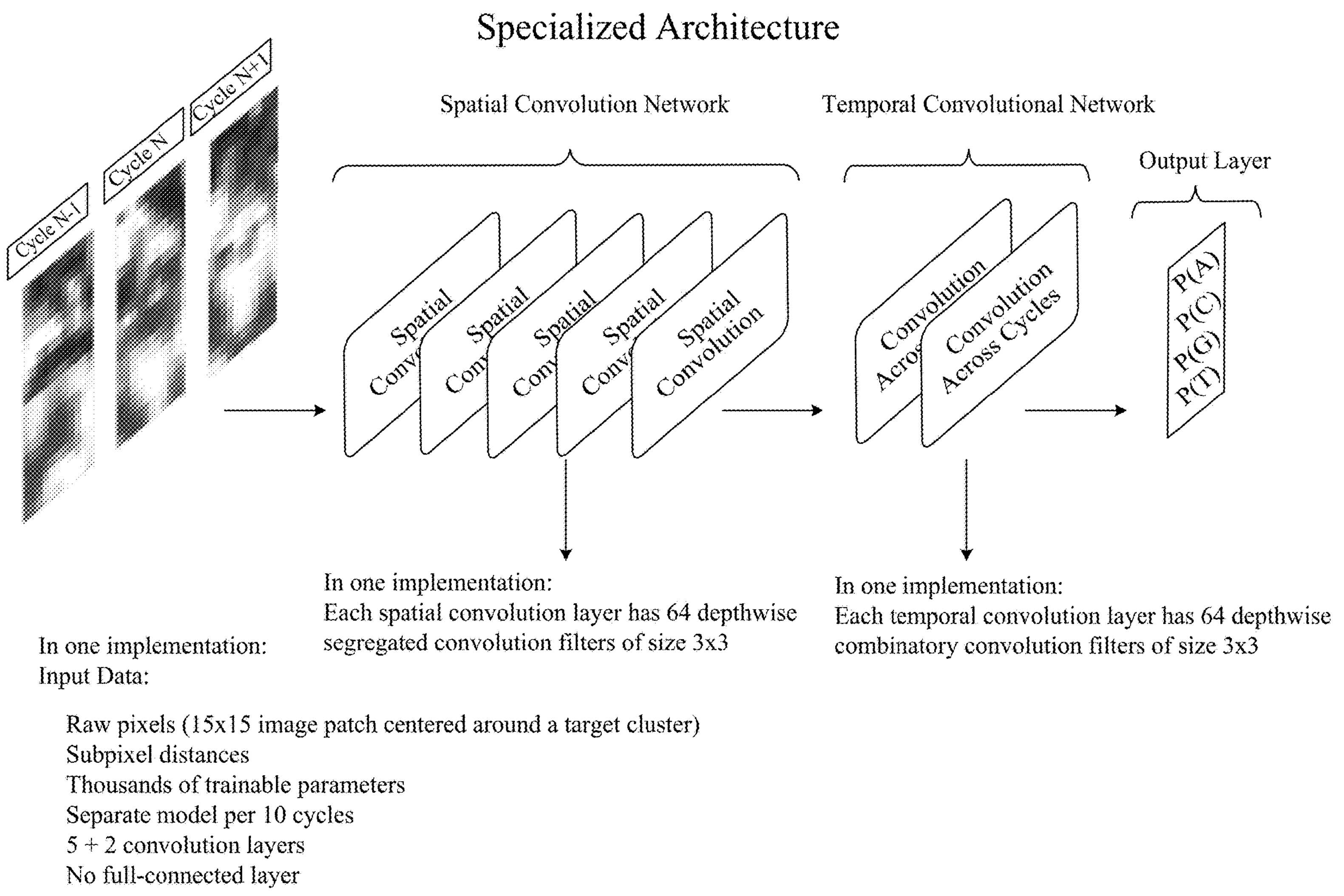
FIG. 11 illustrates one implementation of a specialized architecture of the neural network-based base caller that is used to segregate processing of data for different sequencing cycles.

FIG. 11 illustrates one implementation of the specialized architecture of the neural network-based base caller (e.g., FIG. 7) that is used to segregate processing of data for different sequencing cycles. The motivation for using the specialized architecture is described first.

The neural network-based base caller processes data for a current sequencing cycle, one or more preceding sequencing cycles, and one or more successive sequencing cycles. Data for additional sequencing cycles provides sequence-specific context. The neural network-based base caller learns the sequence-specific context during training and base call them. Furthermore, data for pre and post sequencing cycles provides second order contribution of pre-phasing and phasing signals to the current sequencing cycle.

Images captured at different sequencing cycles and in different image channels are misaligned and have residual registration error with respect to each other. To account for this misalignment, the specialized architecture comprises spatial convolution layers that do not mix information between sequencing cycles and only mix information within a sequencing cycle.

Spatial convolution layers use so-called "segregated convolutions" that operationalize the segregation by independently processing data for each of a plurality of sequencing cycles through a "dedicated, non-shared" sequence of convolutions. The segregated convolutions convolve over data and resulting feature maps of only a given sequencing cycle, i.e., intra-cycle, without convolving over data and resulting feature maps of any other sequencing cycle.

Consider, for example, that the input data comprises (i) current data for a current (time t) sequencing cycle to be base called, (ii) previous data for a previous (time t−1) sequencing cycle, and (iii) next data for a next (time t+1) sequencing cycle. The specialized architecture then initiates three separate data processing pipelines (or convolution pipelines), namely, a current data processing pipeline, a previous data processing pipeline, and a next data processing pipeline. The current data processing pipeline receives as input the current data for the current (time t) sequencing cycle and independently processes it through a plurality of spatial convolution layers to produce a so-called "current spatially convolved representation" as the output of a final spatial convolution layer. The previous data processing pipeline receives as input the previous data for the previous (time t−1) sequencing cycle and independently processes it through the plurality of spatial convolution layers to produce a so-called "previous spatially convolved representation" as the output of the final spatial convolution layer. The next data processing pipeline receives as input the next data for the next (time t+1) sequencing cycle and independently processes it through the plurality of spatial convolution layers to produce a so-called "next spatially convolved representation" as the output of the final spatial convolution layer.

In some implementations, the current pipeline, one or more previous pipeline(s), and one or more next processing pipeline(s) are executed in parallel.

In some implementations, the spatial convolution layers are part of a spatial convolutional network (or subnetwork) within the specialized architecture.

The neural network-based base caller further comprises temporal convolution layers that mix information between sequencing cycles, i.e., inter-cycles. The temporal convolution layers receive their inputs from the spatial convolutional network and operate on the spatially convolved representations produced by the final spatial convolution layer for the respective data processing pipelines.

The inter-cycle operability freedom of the temporal convolution layers emanates from the fact that the misalignment property, which exists in the image data fed as input to the spatial convolutional network, is purged out from the spatially convolved representations by the stack, or cascade, of segregated convolutions performed by the sequence of spatial convolution layers.

Temporal convolution layers use so-called "combinatory convolutions" that groupwise convolve over input channels in successive inputs on a sliding window basis. In one implementation, the successive inputs are successive outputs produced by a previous spatial convolution layer or a previous temporal convolution layer.

In some implementations, the temporal convolution layers are part of a temporal convolutional network (or subnetwork) within the specialized architecture. The temporal convolutional network receives its inputs from the spatial convolutional network. In one implementation, a first temporal convolution layer of the temporal convolutional network groupwise combines the spatially convolved representations between the sequencing cycles. In another implementation, subsequent temporal convolution layers of the temporal convolutional network combine successive outputs of previous temporal convolution layers.

The output of the final temporal convolution layer is fed to an output layer that produces an output. The output is used to base call one or more clusters at one or more sequencing cycles.

During a forward propagation, the specialized architecture processes information from a plurality of inputs in two stages. In the first stage, segregated convolutions are used to prevent mixing of information between the inputs. In the second stage, combinatory convolutions are used to mix information between the inputs. The results from the second stage are used to make a single inference for the plurality of inputs.

This is different from the batch mode technique where a convolution layer processes multiple inputs in a batch at the same time and makes a corresponding inference for each input in the batch. In contrast, the specialized architecture maps the plurality of inputs to the single inference. The single inference can comprise more than one prediction, such as a classification score for each of the four bases (A, C, T, and G).

In one implementation, the inputs have temporal ordering such that each input is generated at a different time step and has a plurality of input channels. For example, the plurality of inputs can include the following three inputs: a current input generated by a current sequencing cycle at time step (t), a previous input generated by a previous sequencing cycle at time step (t−1), and a next input generated by a next sequencing cycle at time step (t+1). In another implementation, each input is respectively derived from the current, previous, and next inputs by one or more previous convolution layers and includes k feature maps.

In one implementation, each input can include the following five input channels: a red image channel (in red), a red distance channel (in yellow), a green image channel (in green), a green distance channel (in purple), and a scaling channel (in blue). In another implementation, each input can include k feature maps produced by a previous convolution layer and each feature map is treated as an input channel. In yet another example, each input can have merely one channel, two channels, or another different number of channels. Incorporated materials of U.S. Patent Application Publication No. 2013/0079232 discuss base calling using various number of channels, such as one-channel, two-channels, or four-channels.

Figure 12:
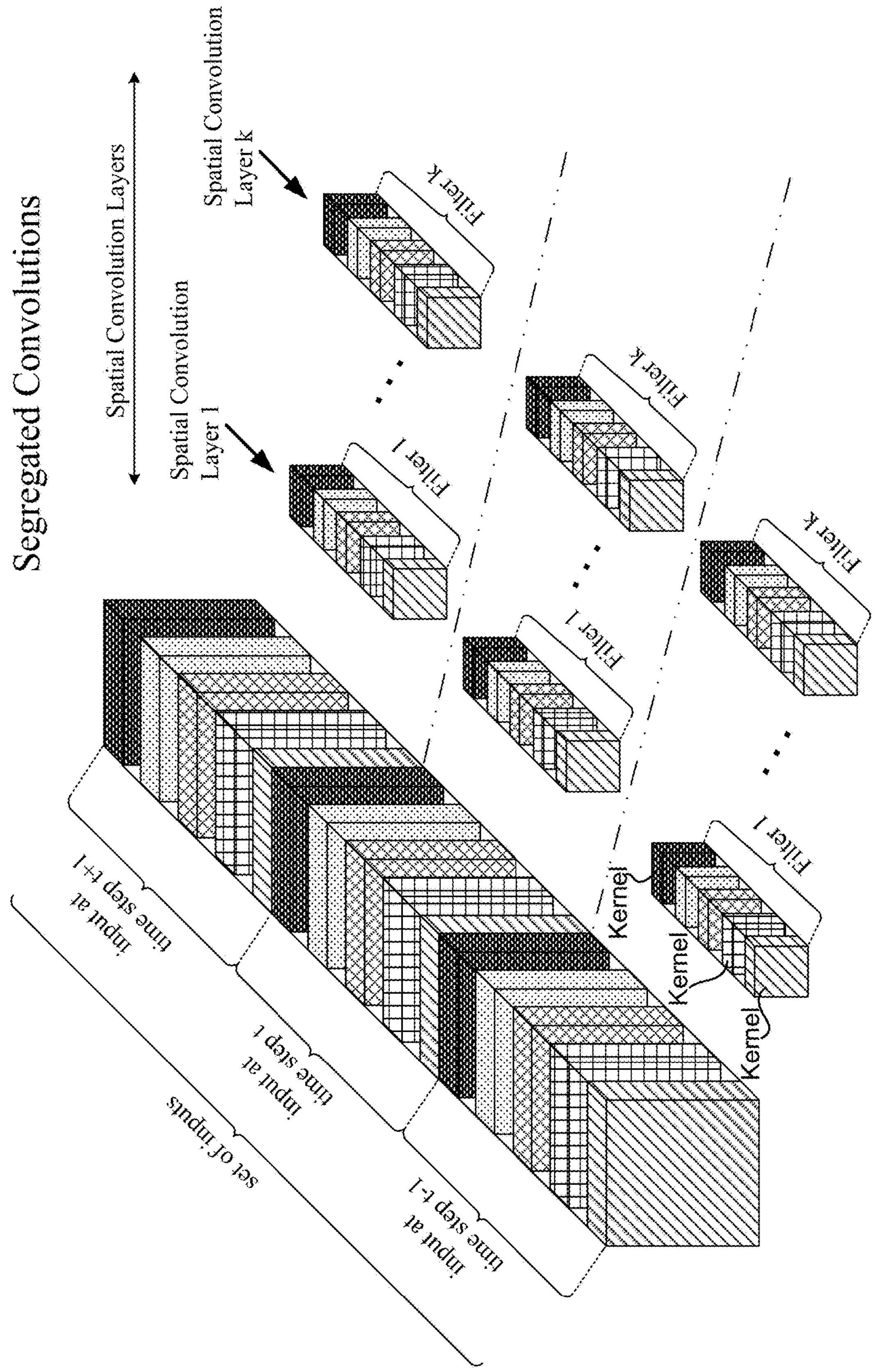
FIG. 12 depicts one implementation of segregated layers, each of which can include convolutions.

FIG. 12 depicts one implementation of segregated layers, each of which can include convolutions. Segregated convolutions process the plurality of inputs at once by applying a convolution filter to each input in parallel. With the segregated convolutions, the convolution filter combines input channels in a same input and does not combine input channels in different inputs. In one implementation, a same convolution filter is applied to each input in parallel. In another implementation, a different convolution filter is applied to each input in parallel. In some implementations, each spatial convolution layer comprises a bank of k convolution filters, each of which applies to each input in parallel.

Figure 13A:
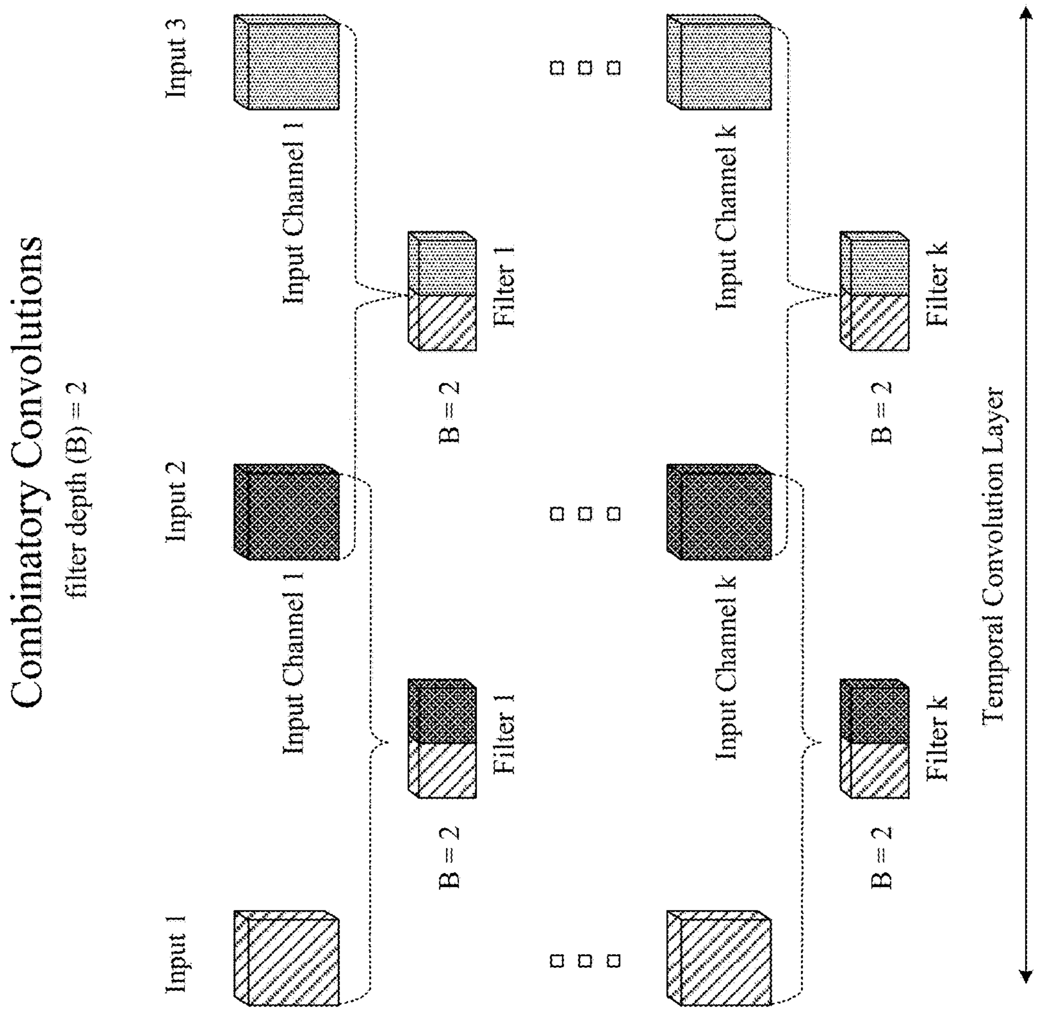
FIG. 13A depicts one implementation of combinatory layers, each of which can include convolutions.
Figure 13B:
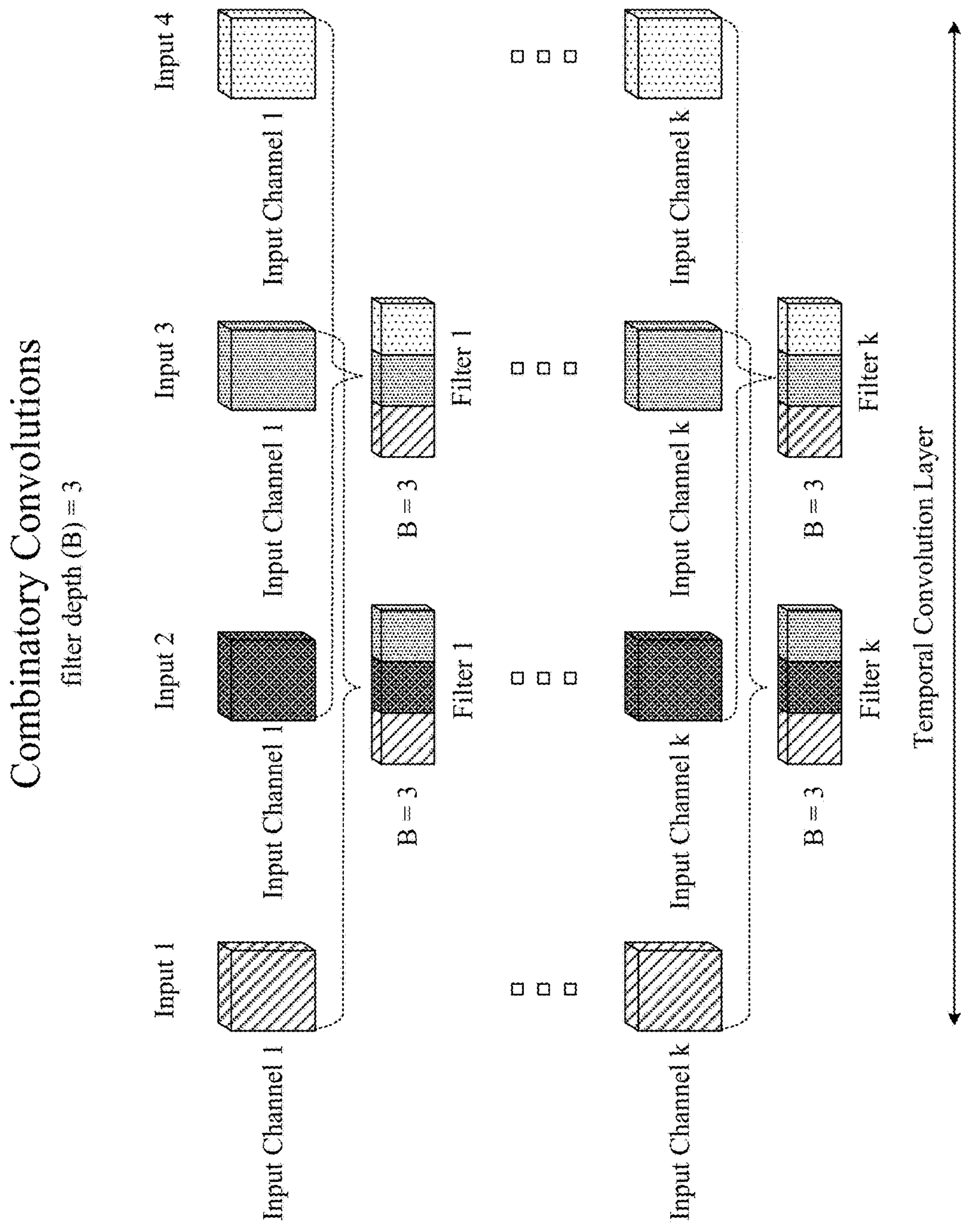
FIG. 13B depicts another implementation of the combinatory layers, each of which can include convolutions.

FIG. 13A depicts one implementation of combinatory layers, each of which can include convolutions. FIG. 13B depicts another implementation of the combinatory layers, each of which can include convolutions. Combinatory convolutions mix information between different inputs by grouping corresponding input channels of the different inputs and applying a convolution filter to each group. The grouping of the corresponding input channels and application of the convolution filter occurs on a sliding window basis. In this context, a window spans two or more successive input channels representing, for instance, outputs for two successive sequencing cycles. Since the window is a sliding window, most input channels are used in two or more windows.

In some implementations, the different inputs originate from an output sequence produced by a preceding spatial or temporal convolution layer. In the output sequence, the different inputs are arranged as successive outputs and therefore viewed by a next temporal convolution layer as successive inputs. Then, in the next temporal convolution layer, the combinatory convolutions apply the convolution filter to groups of corresponding input channels in the successive inputs.

In one implementation, the successive inputs have temporal ordering such that a current input is generated by a current sequencing cycle at time step (t), a previous input is generated by a previous sequencing cycle at time step (t−1), and a next input is generated by a next sequencing cycle at time step (t+1). In another implementation, each successive input is respectively derived from the current, previous, and next inputs by one or more previous convolution layers and includes k feature maps.

In one implementation, each input can include the following five input channels: a red image channel (in red), a red distance channel (in yellow), a green image channel (in green), a green distance channel (in purple), and a scaling channel (in blue). In another implementation, each input can include k feature maps produced by a previous convolution layer and each feature map is treated as an input channel.

The depth B of the convolution filter is dependent upon the number of successive inputs whose corresponding input channels are groupwise convolved by the convolution filter on a sliding window basis. In other words, the depth B is equal to the number of successive inputs in each sliding window and the group size.

In FIG. 13A, corresponding input channels from two successive inputs are combined in each sliding window, and therefore B=2. In FIG. 13B, corresponding input channels from three successive inputs are combined in each sliding window, and therefore B=3.

In one implementation, the sliding windows share a same convolution filter. In another implementation, a different convolution filter is used for each sliding window. In some implementations, each temporal convolution layer comprises a bank of k convolution filters, each of which applies to the successive inputs on a sliding window basis.

Further detail of FIGS. 4-10, and variations thereof, can be found in co-pending U.S. Nonprovisional patent application Ser. No. 17/176,147, titled "HARDWARE EXECUTION AND ACCELERATION OF ARTIFICIAL INTELLIGENCE-BASED BASE CALLER," filed Feb. 15, 2021, which is incorporated by reference as if fully set forth herein.

Figure 14:
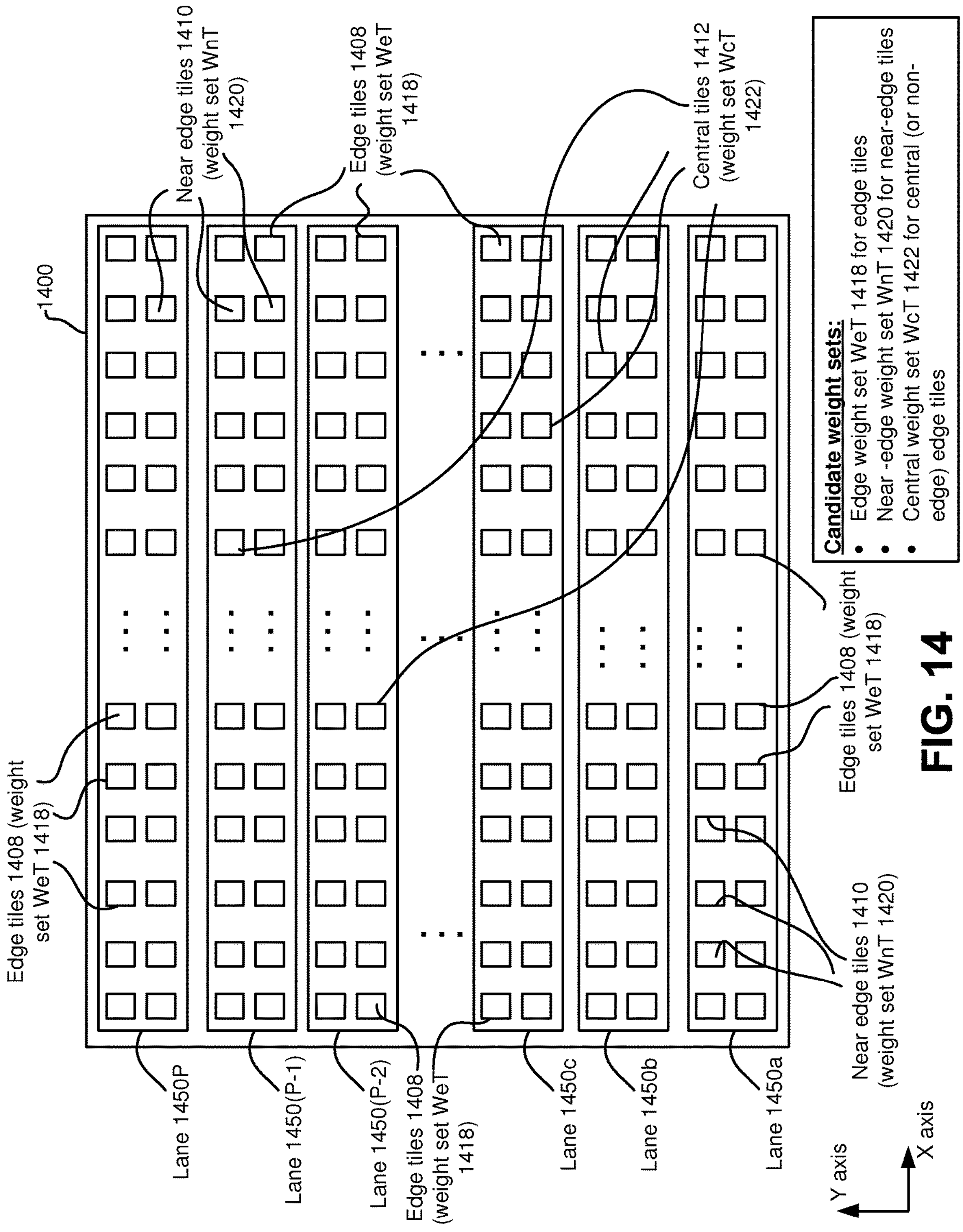
FIGS. 14, 15, and 16 illustrate various example tile-location based weight selection schemes used for base calling.

FIG. 14 illustrates an example tile-location based weight selection scheme used for base calling. For example, illustrated in FIG. 14 is an example flow cell 1400 that comprise a plurality of lanes 1450, each lane comprising a corresponding plurality of tiles (e.g., as also discussed with respect to FIGS. 1 and 2). The depiction of the flow cell 1400 is symbolic in nature, and the flow cell 1400 symbolically depicts various lanes and tiles therewithin, without illustrating various other components of the flow cell 1400. FIG. 14 illustrates a top view of the flow cell 1400 (e.g., without illustrating the flow cover 136 of FIG. 1).

In an embodiment and as also discussed with respect to FIG. 2, the flow cell 1400 is divided or partitioned in a plurality of lanes, such as lanes 1450*a*, 1450*b*, 1450*c*, . . . , 1450(P−2), 1450(P−1), and 1450P, i.e., P number of lanes, where P is a positive integer. As also discussed with respect to FIG. 2, in an embodiment, individual lane 1450 is further partitioned into non-overlapping regions called tiles. In an example, each lane 1450 comprises one or more columns of tiles. For example, in FIG. 14, each lane 1450 comprises two corresponding columns of tiles, where individual tile in FIG. 14 is illustrated by a corresponding rectangular box. A number of tiles within each column of tiles within each lane is implementation specific. Each tile comprises a corresponding plurality of clusters. During the sequencing procedure, the clusters and their surrounding background on the tiles are imaged. For example, FIGS. 2 and 3 illustrate examples of clusters within a tile.

In an embodiment, the tiles of the flow cell 1400 are categorized into various types, e.g., based on locations of the tiles. In the example implementation of FIG. 14, individual ones of the tiles of the flow cell 1400 are categorized as edge tiles 1408, near-edge tiles 1410, or non-edge (or central) tiles 1412.

For example, tiles that are on a vertical (e.g., along Y axis) and/or horizontal (e.g., along X-axis) edges of the flow cell 1400 are categorized as edge tiles 1408, as illustrated in FIG. 14. Thus, an edge tile 1408 is immediate adjacent to a corresponding edge of the flow cell 1400.

Tiles that are near (e.g., immediate adjacent) the edge tiles are categorized as near-edge tiles 1410. For example, near-edge tiles 1410 are one tile apart from an edge of the flow cell 1400. Thus, an edge tile 1408 separates a corresponding near-edge tile 1410 from a corresponding edge of the flow cell 1400.

Tiles that are not edge or near-edge tiles are non-edge tiles 1412, which are also referred to as central tiles 1412. Thus, central tiles 1412 are relatively near a center of the flow cell 1400, e.g., as compared to the edge tiles 1408 or near-edge tiles 1410. For example, central tiles 1412 are separated from the edges of the flow cell 1400 by edge tiles 1408 and near-edge tiles 1410.

Although the tiles of the flow cell 1400 are classified into three categories in FIG. 14 (such as edge, near-edge, and central or non-edge), such categorization is merely an example, and a different tile-location based categorization can also be used. For example, in another implementation, the tiles can be categorized as (i) edge or near edge tiles, and (ii) central tiles (e.g., the edge tile and the near-edge tile categories can be merged into a single category), thereby resulting into two categorizations of the tiles.

As discussed earlier, FIGS. 7 and 10 are example multi-cycle neural network models that can be used for base calling, and FIG. 9 is a simplified representation of a stack of a neural network usable in a system like that of FIGS. 7 and 9. Various functions within the neural network models used for base calling use biases and weights. For example, during a convolution operation, a filer comprising one or more kernels (e.g., as illustrated in FIG. 12) has corresponding plurality of weights, that are trained during a training phase of the neural network models. For example, the weights are tuned using training data generated from one or more tiles, and are used for base calling in the flow cell of FIG. 14, for example.

Base calling cycles are performed for clusters in individual tiles of the flow cell 1400. In an example, parameters relevant for base calling operations for a tile can be based on a relative location of the tile. For example, the excitation light 101 discussed with respect to FIG. 1 are directed towards the tiles of the flow cell, and different tiles can receive different amount of the excitation light 101, e.g., based on a location of individual tile and/or a location of one or more light sources emitting the excitation light 101. For example, if the light source(s) emitting the excitation light 101 are vertically above the flow cell 1400, central tiles 1412 may receive a different amount of light than the edge tiles 1408 and/or the near-edge tiles 1410.

In another example, peripheral or external light (e.g., ambient light from outside the biosensor 100) around the flow cell 1400 can influence the amount and/or characteristics of the excitation light 101 received by individual tiles of the flow cell 1400. Merely as an example, the edge tiles 1408 may receive the excitation light 101, along with some amount of peripheral light from outside the flow cell 1400, whereas the central tiles 1412 may mainly receive the excitation light 101.

In yet another example, individual sensors (or pixel or photodiode) included in the flow cell 1400 (e.g., sensors 106, 108, 110, 112, and 114 illustrated in FIG. 1) can sense light based on a location of the corresponding sensors, which are based on a location of the corresponding tiles. For example, sensing operations performed by one or more sensors associated with the edge tiles 1408 can be influenced by peripheral light (along with the excitation light 101) relatively more than an effect of the peripheral light on sensing operations of one or more other sensors associated with the central tiles 1412.

In another example, the flow of the reactant (e.g., which includes any substance that may be used to obtain a desired reaction during the base calling, such as reagents, enzymes, samples, other biomolecules, and buffer solutions) flowing to various tiles can also be influenced by a tile location. For example, tiles near a source of the reactants can receive higher amount of reactants than tiles that are further from the source.

Thus, put differently, parameters associated with base calling may be slightly different for different category of tiles. Accordingly, in an embodiment, different weight sets are used for different category of tiles, to compensate for the above discussed example tile-location dependency of the base calling process.

For example, in the implementation of FIG. 14, three candidate weight sets are used: (i) edge weight set WeT 1418 for edge tiles, (ii) near-edge weight set WnT 1420 for near-edge tiles, and (iii) central weight set WeT 1422 for central (or non-edge) edge tiles.

In an example, while training a neural network model used for base calling (such as those discussed with respect to FIGS. 7, 9, and 10), the neural network model is initially trained on image data generated solely by the edge tiles 1408 (e.g., training data generated from the near-edge or the central tiles are not used). The resulting weights included in the edge weight set WeT 1418.

Subsequently, the neural network model is trained on image data generated solely by near-edge tiles 1410 (e.g., training data generated from the edge or the central tiles are not used), and the resulting weights are included in the near-edge weight set WnT 1420. Finally, the neural network model is trained on image data generated solely by central tiles 1412 (e.g., training data generated from the edge or near-edge tiles are not used), and the resulting weights are included in the central weight set WeT 1422.

Thus, each weight set includes a corresponding plurality of weights for configuring the neural network model, where the configured neural network is to process sensor data from the corresponding category of tiles. For example, as discussed with respect to FIGS. 7, 9, 10, and 11, the topology of the neural network model includes (i) one or more spatial layers that do not combine sensor data and resulting feature maps between the successive sensing cycles, and (ii) temporal layers that combine resulting feature maps between the successive sensing cycles. Thus, each weight set includes corresponding spatial weights for the spatial layers and corresponding temporal weights for the temporal layers. For example, the edge weight set WeT 1418 for the edge tiles includes corresponding first one or more spatial weights for the spatial layers and corresponding first one or more temporal weights for the temporal layers. Similarly, the central weight set WeT 1422 for the central tiles includes corresponding second one or more spatial weights for the spatial layers and corresponding second one or more temporal weights for the temporal layers.

During the inference phase when the base calling cycles are performed, when bases within clusters of the edge tiles are to be called, the neural network model is configured with the edge weight set WeT 1418, and sensor data from the edge tiles are used for base calling operation. Similarly, when bases within clusters of the near-edge tiles are to be called, the neural network model is configured with the near-edge weight set WnT 1420, and sensor data from the near-edge tiles are used for the base calling operation. Finally, when bases within clusters of the central tiles are to be called, the neural network model is configured with the central weight set WeT 1422, and sensor data from the central tiles are used for the base calling operation.

Figure 15:
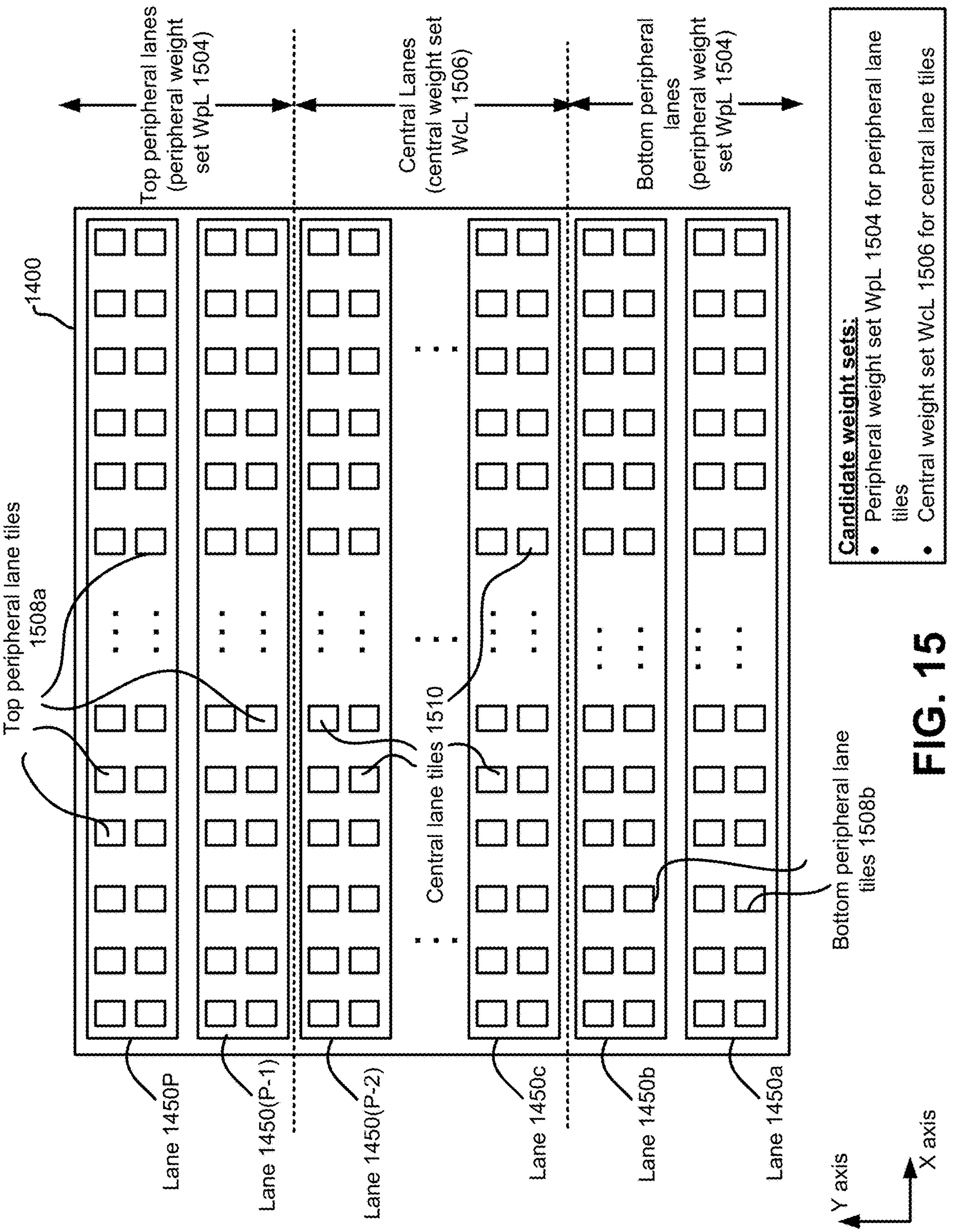

FIG. 15 illustrates another example tile-location based weight selection scheme used for base calling. For example, illustrated in FIG. 15 is the flow cell 1400 that comprise the plurality of lanes 1450*a*, 1450*b*, 1450*c*, . . . , 1450(P−2), 1450(P−1), and 1450P, where each lane includes a corresponding plurality of tiles.

In the example of FIG. 15, each tile of the flow cell 1400 is categorized based on a location of a corresponding lane in which the tile belongs. For example, top one or more lanes of the flow cell 1400 (such as lanes 1450P and 1450(P−1)) are categorized as top peripheral lanes, bottom one or more lanes of the flow cell 1400 (such as lanes 1450*a* and 1450*b*) are categorized as bottom peripheral lanes, and central one or more lanes of the flow cell 1400 (such as lanes 1450*c* and 1450(P−2)) are categorized as central lanes. Note that a number of lanes belonging to each category is merely an example, and variations may be possible. For example, instead of two lanes, each peripheral lane category can include one corresponding lane, or three corresponding lane, or the like.

Tiles within the top peripheral lanes are categorized as top peripheral lane tiles 1508*a*, tiles within the bottom peripheral lanes are categorized as bottom peripheral lane tiles 1508*b*, and tiles within the central lanes are categorized as central lane tiles 1510.

For reasons discussed with respect to FIG. 14, in an embodiment, tiles within various categories of lanes in the flow cell of FIG. 15 can be assigned different weight sets. For example, in the implementation of FIG. 15, two candidate weight sets are used: (i) peripheral weight set WpL 1504 for peripheral lane tiles 1508*a*, 1508*b* (e.g., tiles belonging to the top and the bottom peripheral lanes), and (ii) central weight set WcL 1506 for central lane tiles 1510.

For example, while training a neural network model used for base calling (such as those discussed with respect to FIGS. 7, 9, and 10), the neural network model is initially trained on image data generated solely by peripheral lane tiles 1508*a*, 1508*b* (e.g., training data generated from the central lane tiles 1510 are not used). The resulting weights are included in the peripheral weight set WpL 1504.

Subsequently, the neural network model is trained on image data generated solely by central lane tiles 1510 (e.g., training data generated from the peripheral lane tiles 1508*a*, 1508*b* are not used), and the resulting weights are included in the central weight set WcL 1506.

During the inference phase when the base calling cycles are performed, when bases within clusters of the peripheral lane tiles 1508 are to be called, the neural network model is configured with weights from the peripheral weight set WpL 1504, and sensor data from the peripheral lane tiles 1508 are used for the base calling operation. Similarly, when bases within clusters of the central lane tiles 1510 are to be called, the neural network model is configured with the weights from the central weight set WcL 1506, and sensor data from the central lane tiles 1510 are used for the base calling operation.

Figure 16:
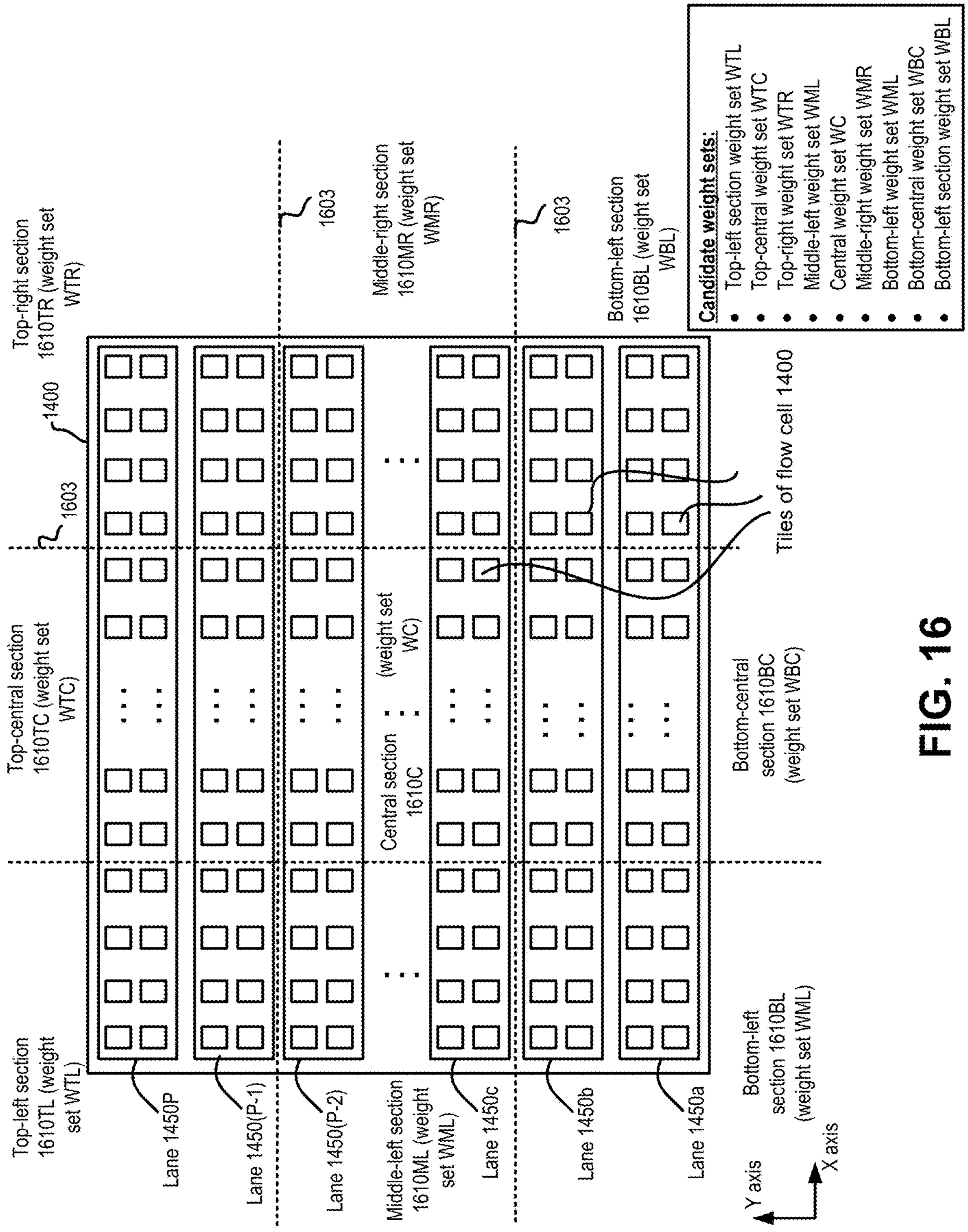

FIG. 16 illustrates yet another example tile-location based weight selection scheme used for base calling. For example, illustrated in FIG. 16 is the flow cell 1400 that comprise the plurality of lanes 1450*a*, 1450*b*, 1450*c*, . . . , 1450(P−2), 1450(P−1), and 1450P, where each lane includes a corresponding plurality of tiles.

In the example of FIG. 16, the flow cell 1400 is divided into a plurality of segments or sections, based on the imaginary dotted lines 1603 (i.e., the dotted lines 1603 are for categorization, and are not actually present in the flow cell). For example, the flow cell 1400 is divided in a top-left section 1610TL (weight set WTL), a top-central section 1610TC (weight set WTC), a top-right section 1610TR (weight set WTR), a middle-left section 1610ML (weight set WML), a central section 1610C (weight set WC), a middle-right section 1610MR (weight set WMR), a bottom-left section 1610BL (weight set WML), a bottom-central section 1610BC (weight set WBC), and a bottom-left section 1610BL (weight set WBL). Each tile of the flow cell 1400 is categorized based on a section in which the tile belongs.

For reasons similar to those discussed with respect to FIG. 14, in an embodiment, tiles within various sections of FIG. 16 are assigned corresponding weight sets. For example, in the implementation of FIG. 16, tiles in the top-left section 1610TL are assigned top-left weight set WTL, tiles in the top-central section 1610TC are assigned top-central weight set WTC, tiles in the top-right section 1610TR are assigned top-right weight set WTR, tiles in the middle-left section 1610ML are assigned middle-left weight set WML, tiles in the central section 1610C are assigned central weight set WC, tiles in the middle-right section 1610MR are assigned middle-right weight set WMR, tiles in the bottom-left section 1610BL are assigned bottom-left weight set WML, tiles in the bottom-central section 1610BC are assigned bottom-central weight set WBC, and tiles in the bottom-left section 1610BL are assigned bottom-left weight set WBL.

For example, while training a neural network model used for base calling (such as those discussed with respect to FIGS. 7, 9, and 10), the neural network model is initially trained on sensor data generated solely by the tiles on the top-left section 1610TL (e.g., sensor data from other categories of tiles are not used), and the resulting weights are included in the top-left weight set WTL. This process is repeated for tiles of various other sections, to generate the various candidate weight sets, such as the top-central weight set WTC, the top-right weight set WTR, the middle-left weight set WML, the central weight set WC, the middle-right weight set WMR, the bottom-left weight set WML, the bottom-central weight set WBC, and the bottom-left section weight set WBL.

During the inference phase when the base calling cycles are performed, when bases within clusters of the tiles within the top-left section 1610TL are to be called, the neural network model is configured with weights within the corresponding top-left weight set WTL, and sensor data from the tiles of the top-left section 1610TL are used for the base calling operation. This process is similarly repeated for tiles of various other sections.

In FIG. 16, the flow cell 1400 is sectioned in 9 different sections. However, the flow cell 1400 can be partitioned in a different number of sections, such as four sections that include a top-left quadrant, top-right quadrant, bottom-left quadrant, and a bottom-right quadrant, for example.

Figure 17A:
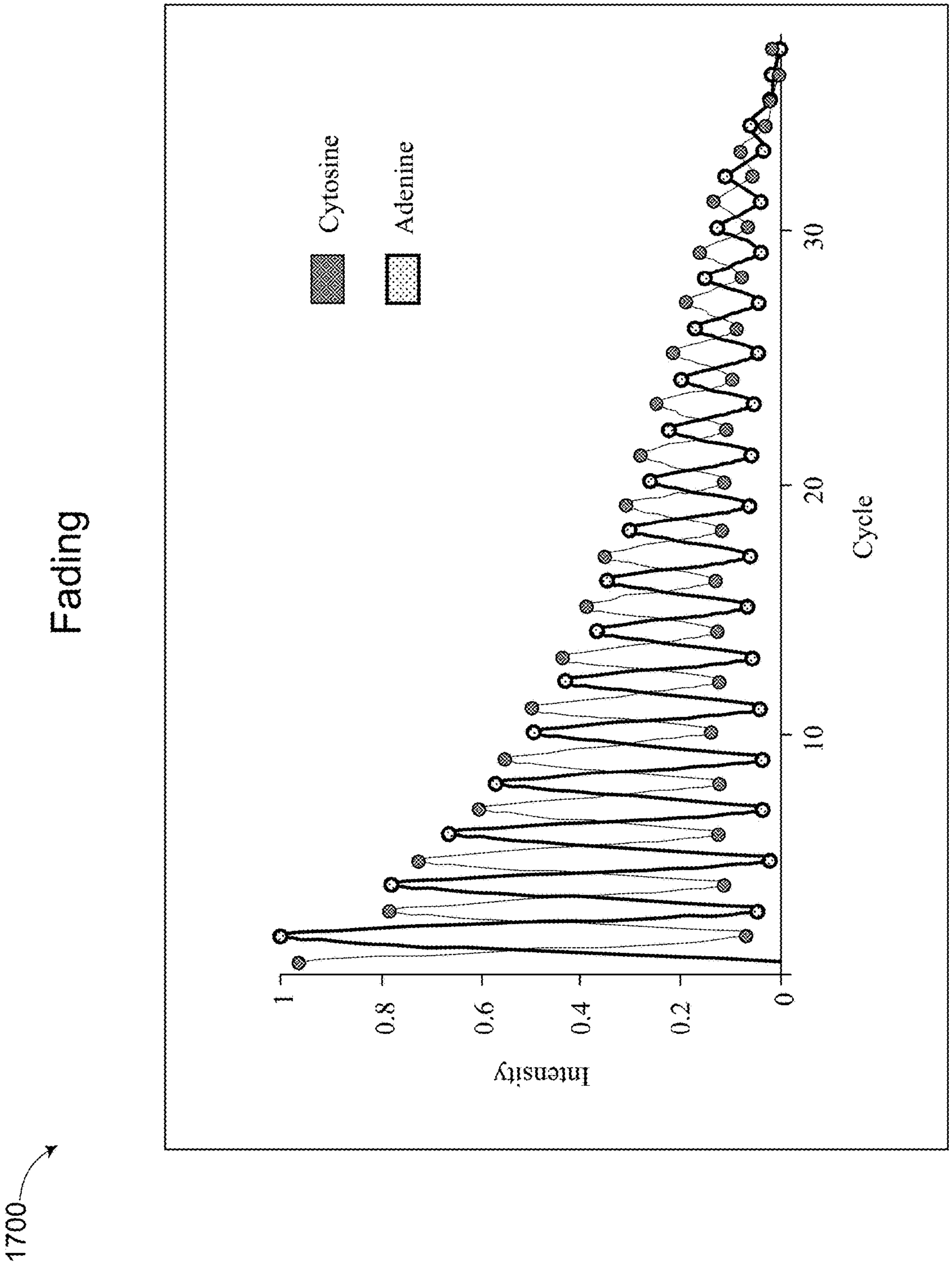
FIG. 17A illustrates an example of fading, in which signal intensity is decreased as a function of cycle number is a sequencing run of a base calling operation.

FIG. 17A illustrates an example of fading, in which signal intensity is decreased as a function of cycle number is a sequencing run of a base calling operation. Fading is an exponential decay in fluorescent signal intensity as a function of cycle number. As the sequencing run progress, the analyte strands are washed excessively, exposed to laser emissions that create reactive species, and subject to harsh environmental conditions. All of these lead to a gradual loss of fragments in each analyte, decreasing its fluorescent signal intensity. Fading is also called dimming or signal decay. FIG. 17A illustrates one example of fading 1700. In FIG. 17A, the intensity values of analyte fragments with AC microsatellites show exponential decay.

Figure 17B:
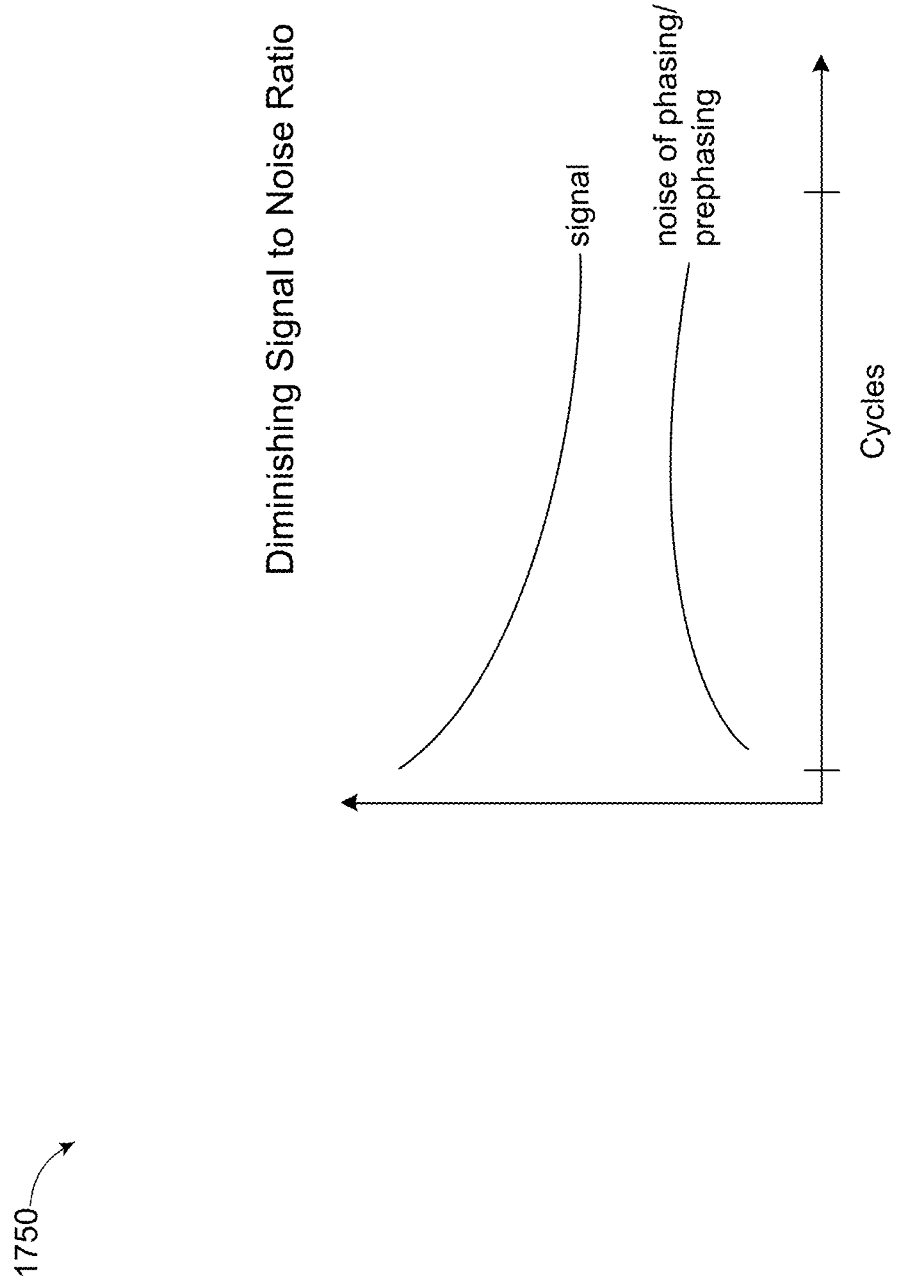
FIG. 17B conceptually illustrates a decreasing signal-to-noise ratio as cycles of sequencing progress.

FIG. 17B conceptually illustrates a decreasing signal-to-noise ratio as cycles of sequencing progress. For example, as sequencing proceeds, accurate base calling becomes increasingly difficult, because signal strength decreases and noise increases, resulting in a substantially decreased signal-to-noise ratio. Physically, it was observed that later synthesis steps attach tags in a different position relative to the sensor than earlier synthesis steps. When the sensor is below a sequence that is being synthesized, signal decay results from attaching tags to strands further away from the sensor in later sequencing steps than in earlier steps. This causes signal decay with progression of sequencing cycles. In some designs, where the sensor is above the substrate that holds cluster, signal could increase, instead of decay, as sequencing proceeds.

In the flow cell design investigated, while the signal decays, noise grows. Physically, phasing and pre-phasing increase noise as sequencing proceeds. Phasing refers to steps in sequencing in which tags fail to advance along the sequence. Pre-phasing refers to sequencing steps in which tags jump two positions forward instead of one, during a sequencing cycle. Phasing and pre-phasing are both relatively infrequent, on the order of once in 500 to 1000 cycles. Phasing is slightly more frequent than pre-phasing. Phasing and pre-phasing impact individual strands in a cluster that is producing intensity data, so the intensity noise distribution from a cluster accumulates in a binomial, trinomial, quadrinomial, etc. expansion as sequencing proceeds.

Further detail of fading, signal decay, and decrease in signal-to-noise ratio, and FIGS. 17A and 17B can be found in U.S. Nonprovisional patent application Ser. No. 16/874,599, titled "Systems and Devices for Characterization and Performance Analysis of Pixel-Based Sequencing," filed May 14, 2020, which is incorporated by reference as if fully set forth herein.

Figure 18:
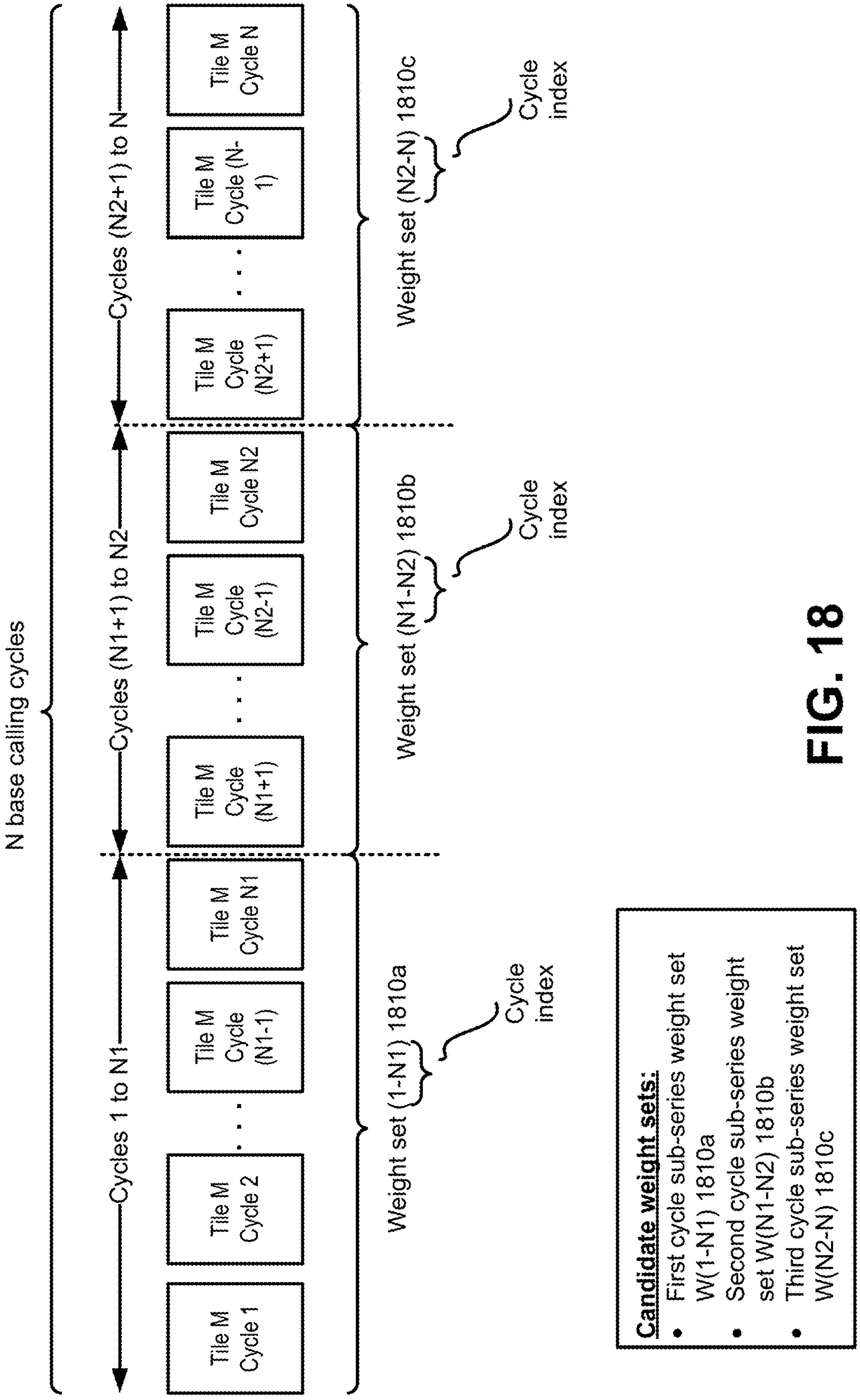
FIG. 18 illustrates an example base calling cycle-number based weight selection scheme used for base calling.

Thus, during base calling, a reliability or quality of the balling calling (e.g., a probability of the called base being correct) can be based on a base calling cycle number for which the current base is being called. Thus, in addition to, or instead of, being dependent on location of tiles (e.g., as discussed with respect to FIGS. 14, 15, 16), weight sets can also be based on a current cycle number for which a base calling operation is being performed. FIG. 18 illustrates an example base calling cycle-number based weight selection scheme used for base calling.

For example, FIG. 18 is directed towards base calling run for an example tile M. Assume that there are N number of base calling cycles, during which strands in various clusters in the example tile M are to be identified. As discussed, due to the factors discussed with respect to FIGS. 17A and 17B and/or various other factors, signal intensity detected by the biosensors (e.g., sensors 106, 108, 110, 112, and 114 of FIG. 1) changes (e.g., decays) as a function of base calling cycle number. For example, assume that the N base calling sensing cycles are divided into three subseries of cycles, such as (a) initial sensing cycles 1 to N1, (b) intermediate sensing cycles (N1+1) to N2, and (c) final sensing cycles (N2+1) to N, as illustrated in FIG. 18, where N>N2>N1, and N, N1, N2 are positive integers. Thus, the N number of sensing cycles are divided in the three subseries of cycles, although the N number of sensing cycles can be divided into a different number (such as 2, 4, or higher) number of three subseries of cycles as well.

Note that a number of sensing cycles in each of the above discussed three subseries of cycles may, or may not, be equal, and is implementation specific. Merely as an example and without limiting the scope of this disclosure, if N is 100, then the 100 cycles can be divided into subseries comprising 30 initial cycles, 30 intermediate cycles, and 40 final cycles. That is, in this simple example, N1=30 and N2=60.

As discussed with respect to FIGS. 17*a* and 17B, an average level of the signal intensity received by the base caller from the biosensors in cycle number N1, for example, can be different from an average level of the signal intensity received by the base caller from the biosensors in cycle number N. Thus, a neural network model trained for cycle number N1, for example, may not provide satisfactory results for cycle number N.

Accordingly, the neural network model used for base calling (such as those discussed with respect to FIGS. 7, 9, and 10) can be trained for specific subseries of cycles. For example, the neural network model is initially trained on sensor data generated solely during sensing cycles 1 to N1, and the resulting weights are included in the first cycle subseries weight set W(1–N1) 1810*a*. Subsequently, the neural network model is trained on sensor data generated solely during sensing cycles (N1+1) to N2, and the resulting weights are included in the second cycle subseries weight set W(N1–N2) 1810*b*. Finally, the neural network model is trained on sensor data generated solely during sensing cycles (N2+1) to N, and the resulting weights are included in third cycle subseries weight set W(N2–N) 1810*c*. Note that, for example, in the first cycle subseries weight set W(1–N1) 1810*a*, the phrase (1–N1) is a cycle index, which implies that this weight set is relevant to sensing cycles 1 to N1. It may be noted that in the example of FIG. 18, the base calling operation is performed using sensor data from one or more channels (such as one channel, two channels, three channels, four channels, or a higher number of channels), and for a given cycle, the weights may be applicable for sensor data from all such channel(s).

During the inference phase, when bases are to be called for cycles 1 to N1, the neural network model is configured with the first cycle subseries weight set W(1–N1) 1810*a*. Similarly, when bases are to be called for cycles (N1+1) to N2, the neural network model is configured with the second cycle subseries weight set W(N1–N2) 1810*b*. Finally, when bases are to be called for cycles N2 to N3, the neural network model is configured with the third cycle subseries weight set W(N2–N3) 1810*c*.

Figure 19:
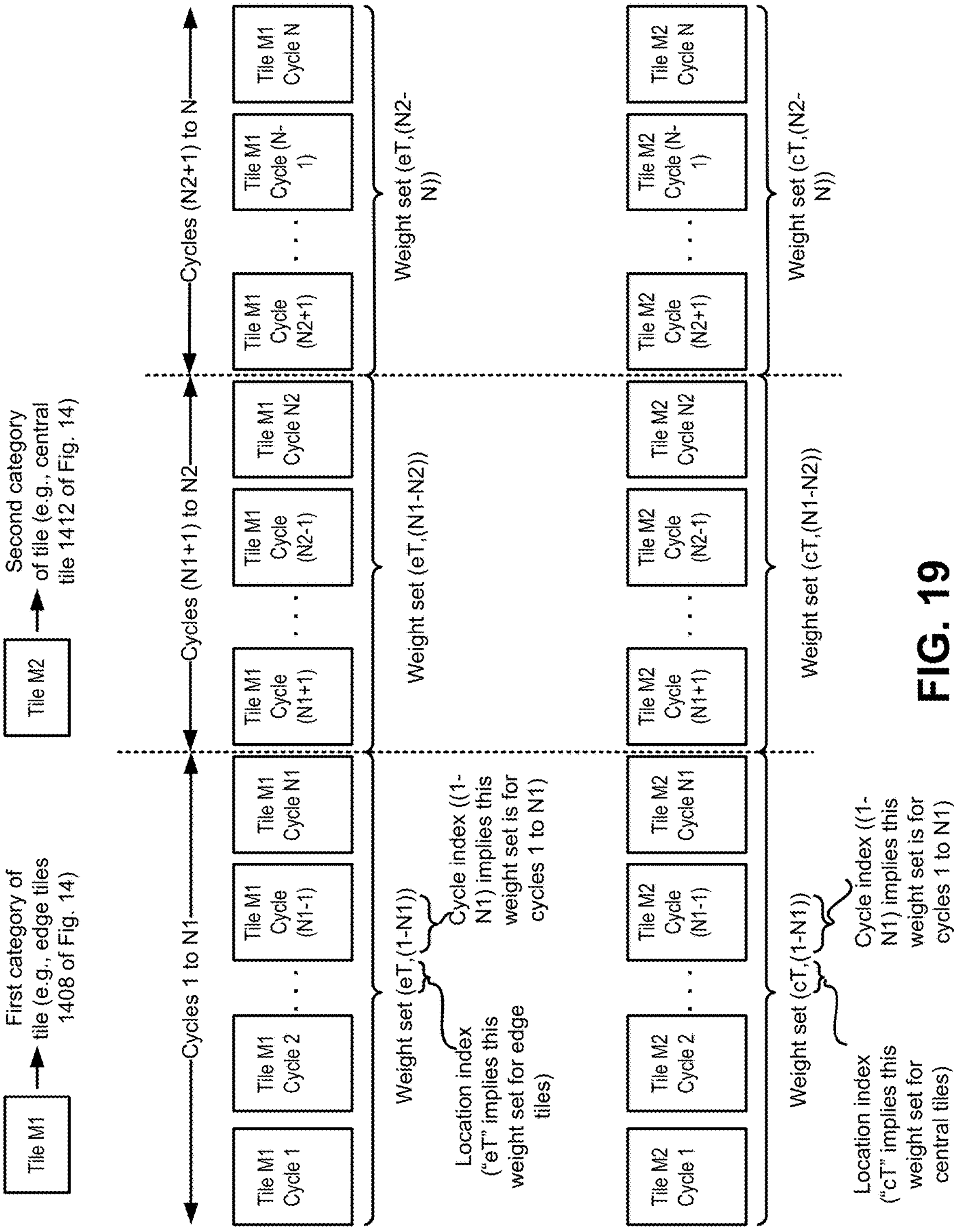

FIGS. 14, 15, 16 illustrate various examples of weight set selection based on location of the tiles. Thus, these figures illustrate various examples of weight set selection based on spatial progression of the base calling operation through locations of the tiles on the biosensor. On the other hand, FIG. 18 illustrate an example of weight set selection based on temporal progression of the base calling operation through subseries of sensing cycles in a series of sensing cycles 1 to N. FIG. 19 combines concept of weight set selection based on spatial tile locations (e.g., as discussed with respect to FIGS. 14-16) with the concept of weight set selection based on temporal progression of the base calling cycles (e.g., as discussed with respect to FIG. 18). Thus, FIG. 19 illustrates an example weight selection scheme based on (i) temporal progression of the base calling cycle numbers and (ii) spatial locations of the tiles.

For example, FIG. 19 illustrates a first tile M1 and a second tile M2. Assume that tile M1 is a first category of tile, and tile M2 is a second category of tile. Merely as an example, tile M1 can be an edge tile 1408 of FIG. 14, and tile M2 can be a central tile 1412 of FIG. 14. Thus, weight set(s) used for base calling strands within clusters in the tile M1 would be different from weight set(s) used for base calling strands within clusters in the tile M2, e.g., as discussed with respect to FIGS. 14, 15, and 16.

Similar to FIG. 18, in FIG. 19 assume that there are N number of base calling cycles, during which strands in various clusters in the tiles M1 and M2 are to be identified. Furthermore, similar to FIG. 18, in FIG. 19 assume that the N base calling sensing cycles are divided into three subseries of cycles, such as (a) initial sensing cycles 1 to N1, (b) intermediate sensing cycles (N1+1) to N2, and (c) final sensing cycles (N2+1) to N, where N>N2>N1, and N, N1, N2 are positive integers, although the N number of sensing cycles can be divided into a different number (such as 2, 4, or higher) number of subseries of cycles as well in other examples.

In an example, the neural network model used for base calling (such as those discussed with respect to FIGS. 7, 9, and 10) can be trained for specific subseries of cycles and for specific tiles. For example, the neural network model is initially trained on sensor data generated solely during sensing cycles 1 to N1 and solely for edge tiles 1408, and the resulting weight set is labelled as "Weight set (eT, (1−N1))." Note that the phrase "eT" in this weight set is a tile category or tile location index, which implies that this weight set is specifically for edge tiles 1408. Also, the phrase "(1−N1)" in this weight set is a cycle index, which implies that this weight set is specifically for sensing cycles 1 to N1.

Similarly, the neural network model is then trained on sensor data generated solely during sensing cycles (N1+1) to N2 and solely for edge tiles 1408, and the resulting weight set is labelled as "Weight set (eT, (N1−N2))." Here too the phrase "eT" is the tile location or tile category index, which implies that this weight set is specifically for edge tiles 1408. Similarly, the phrase "(N1−N2)" in this weight set is the cycle index, which implies that this weight set is specifically for sensing cycles (N1+1) to N2.

Similarly, the neural network model is then trained on sensor data generated solely during sensing cycles (N2+1) to N and solely for edge tiles 1408, and the resulting weight set is labelled as "Weight set (eT, (N2−N))." Here too the phrase "eT" is the tile location index, which implies that this weight set is specifically for edge tiles 1408. Similarly, the phrase "(N2−N)" in this weight set is the cycle index, which implies that this weight set is specifically for sensing cycles (N2+1) to N.

Furthermore, the neural network model is trained on sensor data generated solely during sensing cycles 1 to N1 and solely for central tiles 1412, and the resulting weight set is labelled as "Weight set (eT, (1−N1))." Note that the phrase "eT" in this weight set is the tile location index, which implies that this weight set is specifically for central tiles 1412. Also, the phrase "(1−N1)" in this weight set is a cycle index, which implies that this weight set is specifically for sensing cycles 1 to N1.

Similarly, the neural network model is then trained on sensor data generated solely during sensing cycles (N1+1) to N2 and solely for central tiles 1412, and the resulting weight set is labelled as "Weight set (eT, (N1−N2))." Here too the phrase "eT" is the tile location index, which implies that this weight set is specifically for central tiles 1412. Similarly, the phrase "(N1−N2)" in this weight set is the cycle index, which implies that this weight set is specifically for sensing cycles (N1+1) to N2.

Similarly, the neural network model is then trained on sensor data generated solely during sensing cycles (N2+1) to N and solely for central tiles 1412, and the resulting weight set is labelled as "Weight set (eT, (N2−N))." Here too the phrase "eT" is the tile location index, which implies that this weight set is specifically for central tiles 1412. Similarly, the phrase "(N2−N)" in this weight set is the cycle index, which implies that this weight set is specifically for sensing cycles (N2+1) to N.

During the inference phase, when bases are to be called for cycles 1 to N1 and for tile M1 (e.g., which is an edge tile 1408 in the example of FIG. 19), the neural network model is configured with the weight set (eT, (1−N1)). Similarly, when bases are to be called for cycles (N1+1) to N2 and for tile M1, the neural network model is configured with the weight set (eT, (N1−N2)). Also, when bases are to be called for cycles (N2+1) to N and for tile M1, the neural network model is configured with the weight set (eT, (N2−N)).

Similarly, when bases are to be called for cycles 1 to N1 and for tile M2 (e.g., which is a central tile 1412 in the example of FIG. 19), the neural network model is configured with the weight set (eT, (1−N1)). Similarly, when bases are to be called for cycles (N1+1) to N2 and for tile M2, the neural network model is configured with the weight set (eT, (N1−N2)). Also, when bases are to be called for cycles (N2+1) to N and for tile M2, the neural network model is configured with the weight set (eT, (N2−N)).

Figure 20:
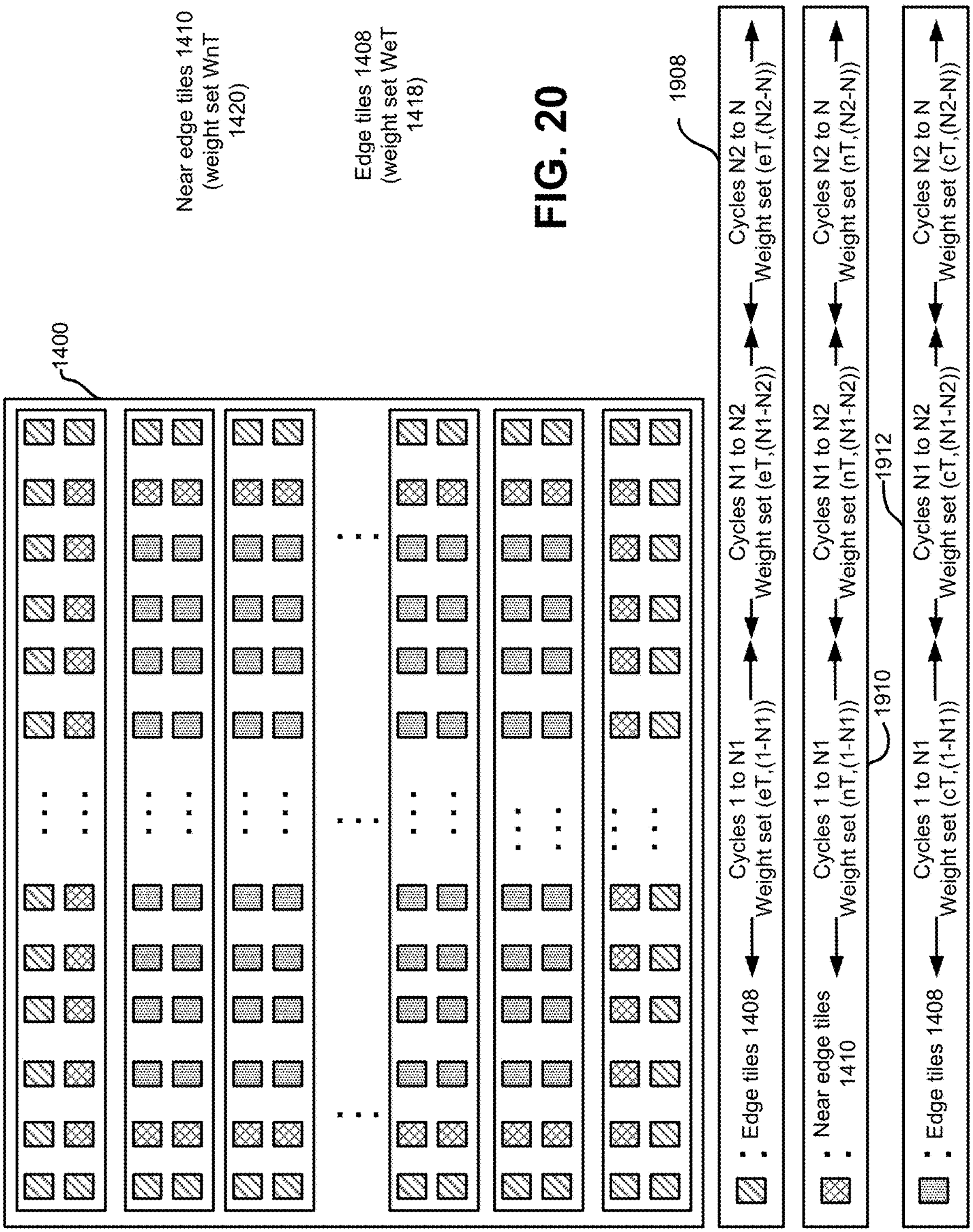

FIG. 20 illustrates another example weight selection scheme based on (i) temporal progression of the base calling cycle numbers and (ii) spatial locations of the tiles. The tile categorization illustrated in FIG. 20 is similar to that illustrated in FIG. 14. For example, referring to FIGS. 14 and 20, the edge tiles 1408 are illustrated with diagonal lines therewithin, the near-edge tiles 1410 are illustrated with cross-hatching therewithin, and the central tiles 1412 are illustrated with dots or grey shaded therewithin.

Three boxes 1908, 1910, and 1912 are also illustrated in FIG. 20. Referring to the box 1908, illustrated are weight sets that are specific for edge tiles 1408 and for various subseries of sensing cycles. For example, weight set (eT, (1−N1)) is specifically for edge tiles 1408 and sensing cycles 1 to N1. Weight set (eT, (N1−N2)) is specifically for edge tiles 1408 and sensing cycles (N1+1) to N2. Weight set (eT, (N2−N)) is specifically for edge tiles 1408 and sensing cycles (N2+1) to N.

Similarly, referring to the box 1910, illustrated are weight sets that are specific for near edge tiles 1410 and for various subseries of sensing cycles. For example, weight set (nT, (1−N1)) is specifically for near edge tiles 1410 and sensing cycles 1 to N1. Weight set (nT, (N1−N2)) is specifically for near edge tiles 1410 and sensing cycles (N1+1) to N2. Weight set (nT, (N2−N)) is specifically for near edge tiles 1410 and sensing cycles (N2+1) to N.

Similarly, referring to box 1912, illustrated are weight sets that are specific for central tiles 1412 and for various subseries of sensing cycles. For example, weight set (eT, (1−N1)) is specifically for central tiles 1412 and sensing cycles 1 to N1. Weight set (eT, (N1−N2)) is specifically for central tiles 1412 and sensing cycles (N1+1) to N2. Weight set (eT, (N2−N)) is specifically for central tiles 1412 and sensing cycles (N2+1) to N.

Figure 21A:
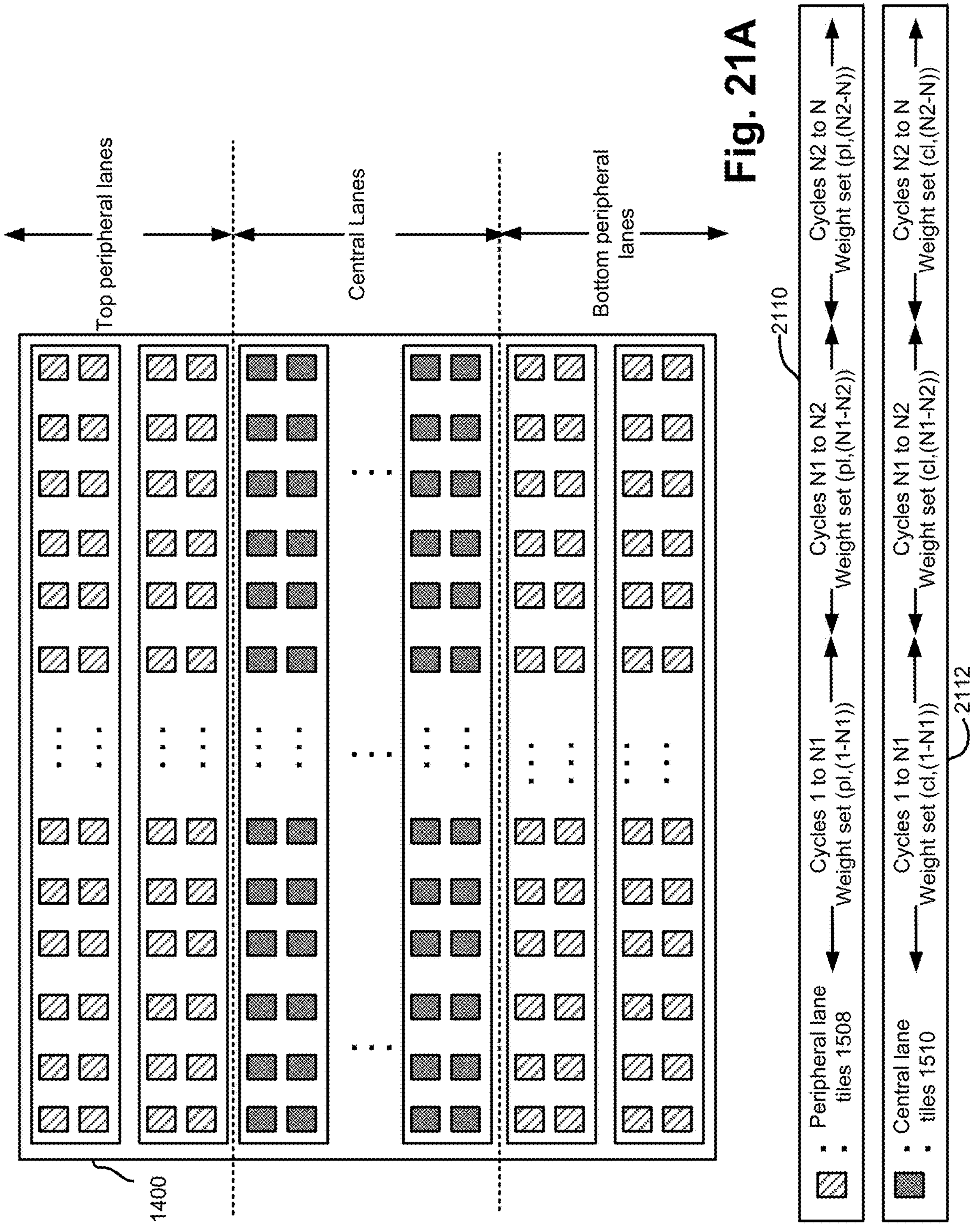

FIG. 21A illustrates another example weight selection scheme based on (i) temporal progression of the base calling cycle numbers and (ii) spatial locations of the tiles. The tile categorization illustrated in FIG. 21A is similar to that illustrated in FIG. 15. For example, referring to FIGS. 15 and 21, the peripheral lane tiles 1508 (which are a combination of top peripheral lane tiles 1508*a* and bottom peripheral lane tiles 1508*b* of FIG. 15) are illustrated with diagonal lines therewithin, and the central lane tiles 1510 are illustrated with dotted or grey shaded boxes.

Two boxes 2110 and 2112 are also illustrated in FIG. 21A. Referring to box 2110, illustrated are weight sets that are specific for peripheral lane tiles 1508 and for various subseries of sensing cycles. For example, weight set (pl, (1-N1)) is specifically for peripheral lane tiles 1508 and sensing cycles 1 to N1. Weight set (pl, (N1-N2)) is specifically for peripheral lane tiles 1508 and sensing cycles (N1+1) to N2. Weight set (pl, (N2-N)) is specifically for peripheral lane tiles 1508 and sensing cycles (N2+1) to N.

Similarly, referring to box 2112, illustrated are weight sets that are specific for central lane tiles 1510 and for various subseries of sensing cycles. For example, weight set (cl, (1-N1)) is specifically for central lane tiles 1510 and sensing cycles 1 to N1. Weight set (cl, (N1-N2)) is specifically for central lane tiles 1510 and sensing cycles (N1+1) to N2. Weight set (cl, (N2-N)) is specifically for central lane tiles 1510 and sensing cycles (N2+1) to N.

In an embodiment and as discussed above, each of the weight set (pl, (1-N1)), weight set (pl, (N1-N2)), weight set (pl, (N2-N)), weight set (cl, (1-N1)), weight set (cl, (N1-N2)), weight set (cl, (N2-N)) comprises corresponding weights. For example, the weight set (pl, (1-N1)) comprises a first plurality of weights for configuring a corresponding plurality of spatial and temporal layers (e.g., see FIGS. 7 and 9 for examples of such layers), the weight set (pl, (N1-N2)) comprises a second plurality of weights for configuring the corresponding plurality of spatial and temporal layers, the weight set (pl, (N2-N)) comprises a third plurality of weights for configuring the corresponding plurality of spatial and temporal layers, the weight set (cl, (1-N1)) comprises a fourth plurality of weights for configuring the corresponding plurality of spatial and temporal layers, the weight set (cl, (N1-N2)) comprises a fifth plurality of weights for configuring the corresponding plurality of spatial and temporal layers, and the weight set (cl, (N2-N)) comprises a sixth plurality of weights for configuring the corresponding plurality of spatial and temporal layers.

At least one weight in the first plurality of weights is different from a corresponding weight in the second plurality of weights (in some examples, two weight sets can have one or more common or same weights). At least one weight in the second plurality of weights is different from a corresponding weight in the third plurality of weights, at least one weight in the third plurality of weights is different from a corresponding weight in the fourth plurality of weights, and so on. In an embodiment, one or more weights in the various weight sets are quantized using different scaling factors.

Because various weight sets are associated with corresponding sequencing cycles, in an example, weights in various weight sets respectively correspond to various sequencing chemistries, sequencing configurations, and/or sequencing assays. For example, the weight set (pl, (1-N1)), weight set (pl, (N1-N2)), and weight set (pl, (N2-N)) respectively correspond to first, second, and third sequencing chemistries (e.g., which are respectively used during sequencing cycles 1 to N1, (N1+1) to N2, and (N2+1) to N). The weight set (pl, (1-N1)), weight set (pl, (N1-N2)), and weight set (pl, (N2-N)) respectively correspond to first, second, and third sequencing assays. The weight set (pl, (1-N1)), weight set (pl, (N1-N2)), and weight set (pl, (N2-N)) respectively correspond to first, second, and third sequencing configurations.

FIG. 21B illustrates yet another example weight selection scheme based on (i) temporal progression of the base calling cycle numbers and (ii) spatial locations of the tiles. The tile categorization illustrated in FIG. 21B is similar to that illustrated in FIG. 16. For example, referring to FIGS. 16 and 21B, the flow cell 1400 is divided in a top-left section 1610TL, a top-central section 1610TC, a top-right section 1610TR, a middle-left section 1610ML, a central section 1610C, a middle-right section 1610MR, a bottom-left section 1610BL, a bottom-central section 1610BC, and a bottom-left section 1610BL. Each tile of the flow cell 1400 is categorized based on a section in which the tile belongs.

FIG. 21B also illustrates a table 2150 that includes various weights for tiles of various sections, as well as for various subseries of sensing cycles 1 to N. For example, referring to the first row of table 2150, weight set (TL, (1-N1)) is specifically for the tiles of the top-left section 1610TL and sensing cycles 1 to N1. Weight set (TL, (N1-N2)) is specifically for the tiles of the top-left section 1610TL and sensing cycles (N1+1) to N2. Weight set (TL, (N2-N)) is specifically for the tiles of the top-left section 1610TL and sensing cycles (N2+1) to N.

Similarly, referring to the second row of table 2150, weight set (TC, (1-N1)) is specifically for the tiles of the top-central section 1610TC and sensing cycles 1 to N1. Weight set (TC, (N1-N2)) is specifically for the tiles of the top-central section 1610TC and sensing cycles (N1+1) to N2. Weight set (TC, (N2-N)) is specifically for the tiles of the top-central section 1610TC and sensing cycles (N2+1) to N. Similarly, various other rows of the table 2150 include weight sets for tiles of various other sections and for various subseries of sensing cycles, and will be apparent to those skilled in the art based on the above discussion.

Figure 22:
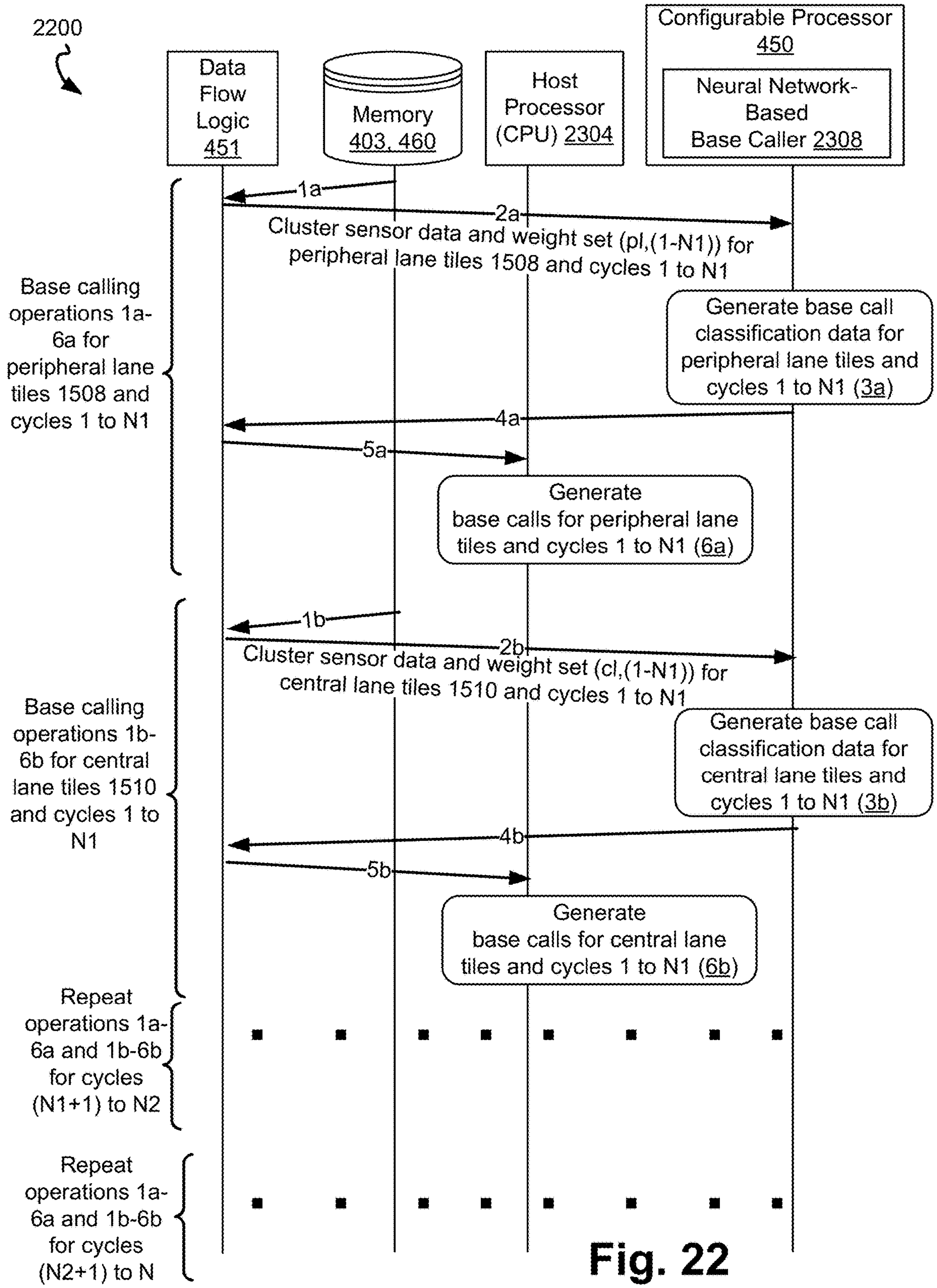
FIG. 22 illustrates one implementation of base calling operations, in which weight sets used for the base calling are selected based on spatial tile information and temporal subseries of sensing cycle information.

FIG. 22 illustrates one implementation of base calling operations 2200, in which weight sets used for the base calling are selected based on spatial tile information and temporal subseries of sensing cycle information.

For the base calling operations 2200 of FIG. 22, the tiles of the flow cell 1400 are assumed to be categorized in accordance with the examples of FIGS. 15 and 21A. Such a tile categorization is not intended to limit the scope of this disclosure, and the base calling operations 2200 can also be applied to any other type of tile categorization, such as any of those discussed with respect to FIGS. 14, 16, 20, 21B, and/or any other tile categorization envisioned by those skilled in the art based on the teachings of this disclosure.

Furthermore, for the base calling operations 2200 of FIG. 22, the N number of sensing cycles are assumed to be divided into three subseries of cycles comprising (a) cycles 1 to N1, (b) cycles (N1+1) to N2, and (c) cycles (N2+1) to N, as discussed with respect to FIGS. 18-21B. Again, such a division of the sensing cycles is not intended to limit the scope of this disclosure, and the base calling operations 2200 can also be applied to any other type of subdivision of sensing cycles that can be envisioned by those skilled in the art based on the teachings of this disclosure.

In FIG. 22, base calling operations 1*a*-6*a* are specifically for peripheral lane tiles and cycles 1 to N1. Similarly, base calling operations 1*b*-6*b* are specifically for central lane tiles and cycles 1 to N1. The operations of 1*a*-6*a* and for 1*b*-6*b* can be repeated for cycles (N1+1) to N2, and can be further repeated for cycles (N2+1) to N, although such repetitions are not illustrated in detail FIG. 22. Such repetitions for cycles (N1+1) to N2, and further for cycles (N2+1) to N will be appreciated by those skilled in the art, based on the discussion of the operations 1*a*-6*a* and 1*b*-6*b* for cycles 1 to N1.

At action 1*a*, the data flow logic 451 (e.g., see FIG. 4) receives cluster sensor data and weight set (pl, (1-N1)) (see FIG. 21A) for peripheral lane tiles 1508 and for cycles 1 to N1. The cluster data includes sequencing images that depict intensity emissions of clusters within the peripheral lane tiles 1508 at sequencing cycles 1 to N1 of the sequencing run, as discussed above. At action 2*a*, the data flow logic 451 forwards the cluster data and the weight set (pl, (1−N1)) for the peripheral lane tiles 1508 and for cycles 1 to N1 to a neural network based base-caller 2308 (e.g., example of which are illustrated in FIGS. 7, 9, 10) executed by the configurable processor 450 (e.g., see FIG. 4). The cluster data and the weight set (pl, (1−N1)) for the peripheral lane tiles 1508 and for cycles 1 to N1 are loaded in the neural network based base-caller 2308. Also, although not illustrated in FIG. 22, a topology of the neural network model is also loaded from the memory, via the data flow logic 451, to the configurable processor 450.

At action 3*a*, the configurable processor 450 configures the topology of the neural network running on the configurable processor 450 with the loaded weight set (pl, (1−N1)). The neural network-based base caller 2308, configured with the loaded weight set (pl, (1−N1)), generates representations (e.g., feature maps) from the cluster data based on the loaded weight set (pl, (1−N1)) (e.g., by processing the cluster data through its configured spatial and temporal convolution layers), and produces base call classification data (e.g., base call classification scores) for the plurality of clusters within the peripheral lane tiles 1508 and for the sequencing cycles 1 to N1 based on the representations. For example, the neural network-based base caller 2308 applies the loaded weight set (pl, (1−N1)) on the cluster data, to generate the base call classification data. In one implementation, the base call classification scores are unnormalized, for example, they are not subjected to exponential normalization by a softmax function.

At action 4*a*, the configurable processor 450 sends to the data flow logic 451 the base call classification data for the clusters within the peripheral lane tiles 1508 and for cycles 1 to N1. At action 5*a*, the data flow logic 451 provides, to the host processor 2304, the base call classification scores for the clusters within the peripheral lane tiles 1508 and for cycles 1 to N1.

At action 6*a*, the host processor 2304 normalizes the unnormalized base call classification scores (e.g., by applying a softmax function 740 of FIG. 7 or 930 of FIG. 9), and generates normalized base call classification scores, i.e., base calls, for strands within the clusters of the peripheral lane tiles 1508 and for cycles 1 to N1.

Thus, in operations 1*a*-6*a*, the system base calls strands within the clusters of the peripheral lane tiles 1508 and for cycles 1 to N1, using the weight set (pl, (1−N1)) that is specifically trained for the peripheral lane tiles 1508 and for cycles 1 to N1. Note that the operations 1*a*-6*a* depict a high level and simplified version of base calling operations, and may not illustrate one or more other operations that may be performed for base calling. Further detail of base calling operations may be found in U.S. Provisional Patent Application No. 63/072,032, titled "DETECTING AND FILTERING CLUSTERS BASED ON ARTIFICIAL INTELLIGENCE-PREDICTED BASE CALLS," filed 28 Aug. 2020, which is incorporated by reference as if fully set forth herein.

Operations 1*a*-6*a* are specifically for base calling for strands within clusters of the peripheral lane tiles 1508 and for cycles 1 to N1. These operations are repeated as operations 1*b*-6*b*, but for clusters within the central lane tiles 1510 and for cycles 1 to N1. For example, at action 1*b*, the data flow logic 451 receives cluster data and weight set (cl, (1−N1)) (see FIG. 21A) for the central lane tiles 1510 and for cycles 1 to N1. The cluster data includes sequencing images that depict intensity emissions of clusters within the central lane tiles 1510 at sequencing cycles 1 to N1 of the sequencing run, as discussed above. At action 2*b*, the data flow logic 451 forwards the cluster data and the weight set (cl, (1−N1)) for the central lane tiles 1508 and for cycles 1 to N1 to the neural network based base-caller 2308 executed by the configurable processor 450. The weight set (cl, (1−N1)) for the central lane tiles 1510 and for cycles 1 to N1 are used to reconfigure the neural network based base-caller 2308.

At action 3*b*, the reconfigured neural network-based base caller 2308, running on the configurable processor 450, generates initial representations (e.g., feature maps) from the cluster data (e.g., by processing the cluster data through its spatial and temporal convolution layers), and produces base call classification scores for the plurality of clusters within the central lane tiles 1510 and for the sequencing cycles 1 to N1 based on the initial intermediate representations. In one implementation, the initial base call classification scores are unnormalized, for example, they are not subjected to exponential normalization by a softmax function.

At action 4*b*, the configurable processor 450 sends to the data flow logic 451 the base call classification scores for the clusters within the central lane tiles 1510 and for cycles 1 to N1. At action 5*b*, the data flow logic 451 provides, to the host processor 2304, the base call classification scores for the clusters within the central lane tiles 1510 and for cycles 1 to N1.

At action 6*b*, the host processor 2304 normalizes the unnormalized base call classification scores (e.g., by applying the softmax function), and generates normalized base call classification scores, i.e., base calls, for strands within the clusters of the central lane tiles 1510 and for cycles 1 to N1.

Thus, base calling operations 1*a*-6*a* are specifically for the peripheral lane tiles 1508 and cycles 1 to N1. Similarly, base calling operations 1*b*-6*b* are specifically for the central lane tiles 1510 and cycles 1 to N1. The operations of 1*a*-6*a* and for 1*b*-6*b* are repeated for cycles (N1+1) to N2, and are further repeated for cycles (N2+1) to N, as symbolically illustrated in FIG. 22.

Referring back to FIG. 7, the illustrated model includes segregated stacks 701, 702, 703, 704, 705. For example, stack 701 receives as input, tile data for the patch from cycle K+2. Stack 702 receives as input, tile data for the patch from cycle K+1. Stack 703 receives as input, tile data for the patch from cycle K. Stack 704 receives as input, tile data for the patch from cycle K−1. Stack 705 receives as input, tile data for the patch from cycle K−2. The layers of the segregated stacks each execute a convolution operation of a kernel including a plurality of filters over the input data for the layer. The output feature set (intermediate data) from each of the stacks 701-705 is provided as input to an inverse hierarchy 720 of temporal combinatorial layers, in which the intermediate data from the multiple cycles are combined.

Thus, as discussed with respect to FIGS. 7, 9, and 11, the stacks 701, . . . , 705 perform segregated spatial convolutions. There is no temporal comingling or interaction between input from various cycles within the various stacks 701, . . . , 705. Finally, after data processing in the stacks 701, . . . , 705, in the inverse hierarchy 720 there is processing of data from various sequential cycles. The various layers within the stacks 701, . . . , 705 are also referred to herein as spatial layers, and weights of kernels of various filters within the stacks 701, . . . , 705 are referred to herein as spatial weights. Similarly, the various layers within the inverse hierarchy 720 are also referred to herein as temporal layers, and weights of kernels of various filters within the inverse hierarchy 720 are also referred to herein as temporal weights. For example, the weights applied during the spatial convolutions 921, 922, 923 in FIG. 9 are the spatial weights, whereas the weights applied during the temporal convolutions of layers 924, 925 in FIG. 9 are the temporal weights.

Figure 23A:
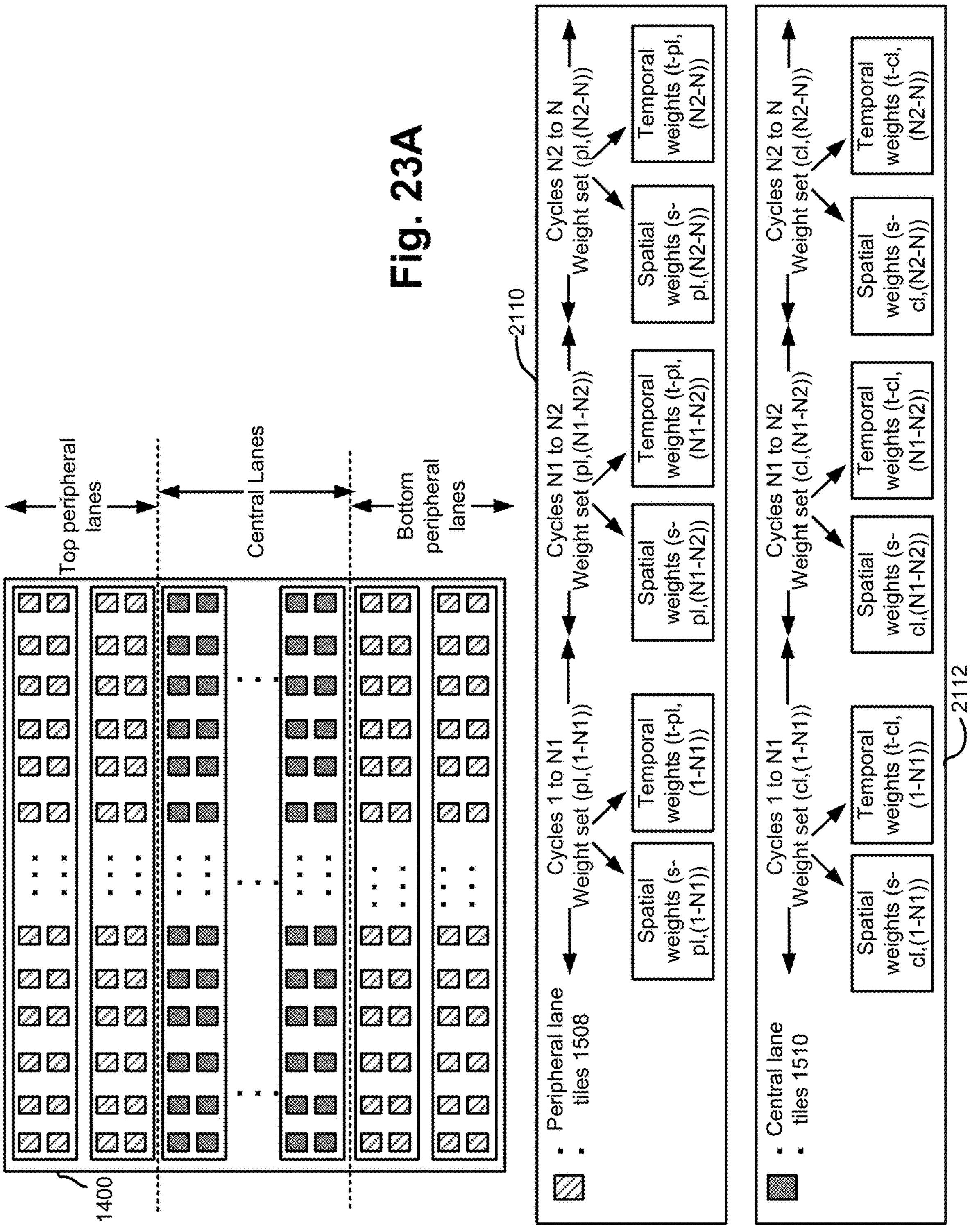
FIG. 23A illustrates various weights sets for various categories of tiles and for various sensing cycles, individual weight set comprising corresponding spatial weights and corresponding temporal weights.

FIG. 23A illustrates various weights sets for various categories of tiles and for various sensing cycles, individual weight set comprising corresponding spatial weights and corresponding temporal weights. The tile categorization illustrated in FIG. 23A is similar to that discussed with respect to FIGS. 15 and 21A. As discussed with respect to FIG. 21A, peripheral lane tiles 1508 for cycles 1 to N1 are associated with corresponding weight set (pl, 1−N1). As illustrated in FIG. 23A, the weight set (pl, 1−N1) includes corresponding spatial weights (s-pl, (1−N1)) and corresponding temporal weights (t-pl, (1−N1)). The spatial weights (s-pl, (1−N1)) are used to configure the spatial layers of the neural network model, when the neural network model is to process cluster sensor data for peripheral lane tiles 1508 for cycles 1 to N1. The temporal weights (t-pl, (1−N1)) are used to configure the temporal layers of the neural network model, when the neural network model is to process cluster sensor data for peripheral lane tiles 1508 for cycles 1 to N1.

Similarly, as also discussed with respect to FIG. 21A, peripheral lane tiles 1508 for cycles N1 to N2 are associated with corresponding weight set (pl, N1−N2). As illustrated in FIG. 23A, the weight set (pl, N1−N2) includes corresponding spatial weights (s-pl, (N1−N2)) and corresponding temporal weights (t-pl, (N1−N2)). Various other weight sets of FIG. 23A also similarly have corresponding spatial and temporal weights.

Figure 23B:
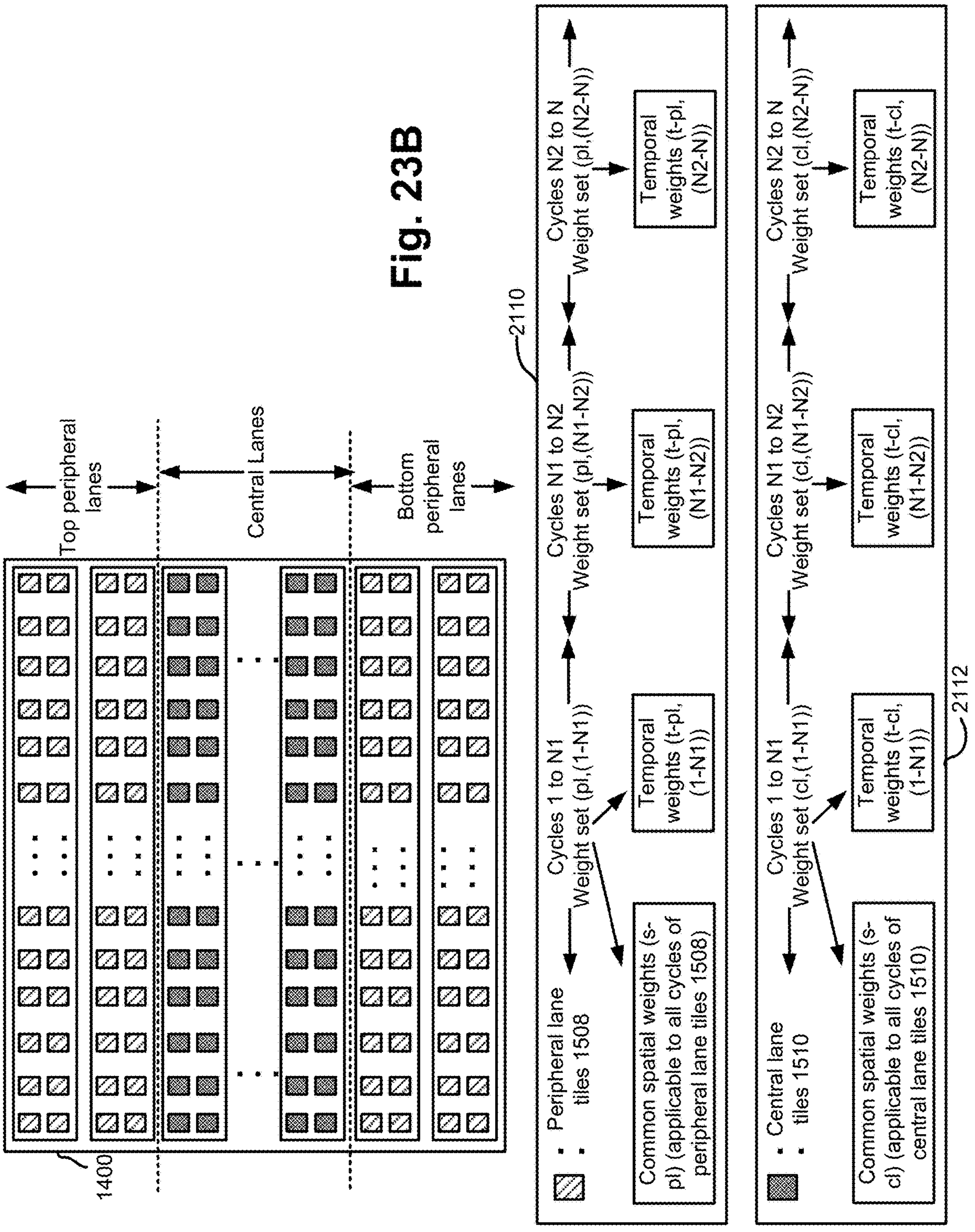
FIG. 23B illustrates various weights sets for various categories of tiles and for various cycles, wherein different weight sets of a specific category of tile includes common spatial weights and different temporal weights.

FIG. 23B illustrates various weights sets for various categories of tiles and for various cycles, wherein different weight sets of a specific category of tile includes common spatial weights and different temporal weights. The tile categorization illustrated in FIG. 23A is similar to that discussed with respect to FIGS. 15, 21A, 23A. However, unlike FIG. 23A, in FIG. 23B, the weight sets (pl, (1−N1)), (pl, (N1−N2)), and (pl, (N2−N)) for the peripheral lane tiles 1508 have common spatial weights (s-pl). Thus, the same or common spatial weights (s-pl) are used for the peripheral lane tiles 1508 and for each of the subseries of cycles 1 to N1, (N+1) to N2, and (N2+1) to N.

The weight sets (pl, (1−N1)), (pl, (N1−N2)), and (pl, (N2−N)) have different temporal weights, such as temporal weights (t-pl, (1−N1)), temporal weights (t-pl, (N1−N2)), and temporal weights (t-pl, (N2−N)), respectively.

Similarly, the weight sets (cl, (1−N1)), (cl, (N1−N2)), and (cl, (N2−N)) for the central lane tiles 1510 have common spatial weights (s-cl). Thus, the same or common spatial weights (s-cl) are used for the central lane tiles 1510 and for each of the subseries of cycles 1 to N1, (N+1) to N2, and (N2+1) to N.

The weight sets (cl, (1−N1)), (cl, (N1−N2)), and (cl, (N2−N)) have different temporal weights, such as temporal weights (t-cl, (1−N1)), temporal weights (t-cl, (N1−N2)), and temporal weights (t-cl, (N2−N)), respectively.

In an embodiment and as discussed with respect to in FIGS. 17A and 17B, fading, phasing, and/or pre-phasing cause deterioration of sensor data, as sequencing cycles progress. Such deterioration is addressed by the temporal layers (such as layers within the inverse hierarchy 720 of FIG. 7, or layers 924, 925 of FIG. 9) of the neural network model. Accordingly, in FIG. 23B, the temporal weights for various subseries of sequencing cycles are trained differently. For example, temporal weights for cycles 1 to N1 and for a given tile category are different from the temporal weights for cycles N1 to N2 for the same tile category. In contrast, as spatial layers (such as layers within stacks 701, . . . , 705 of FIG. 7, or spatial convolutions 921, 922, 923 of FIG. 9) may not significantly cure the deterioration in signal quality, all cycles share common spatial weights for a given tile category, as illustrated in FIG. 23B.

Thus, when processing sensor data of a specific tile category, say for peripheral lane tiles 1508, the common spatial weights (s-pl) and the temporal weights (t-pl, (1−N1)) of the weight set (pl, (1−N1)) for cycles 1 to N1 are initially loaded in the configurable processor, and the neural network-based base caller 2308 is configured with these spatial and temporal weights. For example, the spatial layers of the neural network-based base caller 2308 are configured with the common spatial weights (s-pl), and the temporal layers of the neural network-based base caller 2308 are configured with the temporal weights (t-pl, (1−N1)). The configured neural network-based base caller 2308 applies the configured spatial and temporal layers on the sensor data for cycles 1 to N1 of the peripheral lane tiles 1508, to produce base call classification data for the cycles 1 to N1 of the peripheral lane tiles 1508.

Subsequently, before processing sensor data for cycle (N1+1), the temporal weights (t-pl, (N1−N2)) of the weight set (pl, (N1−N2)) are loaded, without loading any corresponding spatial weights of this weight set. The temporal layers of the neural network-based base caller 2308 are configured with the temporal weights (t-pl, (N1−N2)). The neural network-based base caller 2308 then applies the previously configured spatial layers (e.g., which were configured previously with the common spatial weights (s-pl)) and the reconfigured temporal layers (e.g., which are reconfigured with the temporal weights (t-pl, (N1−N2))) on the sensor data for cycles (N1+1) to N2 of the peripheral lane tiles 1508 to produce base call classification data for the cycles (N1+1) to N2 of the peripheral lane tiles 1508.

Subsequently, before processing sensor data for cycle (N2+1), the temporal weights (t-pl, (N2−N)) of the weight set (pl, (N2−N)) are loaded, without loading any corresponding spatial weights of this weight set. The temporal layers of the neural network-based base caller 2308 are reconfigured with the temporal weights (t-pl, (N2−N)). The neural network-based base caller 2308 then applies the previously configured spatial layers (e.g., which were configured previously with the common spatial weights (s-pl)) and the reconfigured temporal layers (e.g., which are reconfigured with the temporal weights (t-pl, (N2−N))) on the sensor data for cycles (N2+1) to N of the peripheral lane tiles to produce base call classification data for the cycles (N2+1) to N of the peripheral lane tiles.

The base call classification data for other tile categories (such as the central lane tiles 1510) are produced in a corresponding similar manner, which will be appreciated by those skilled in the art based on the above discussion and the illustration of FIG. 23B.

Figure 23C:
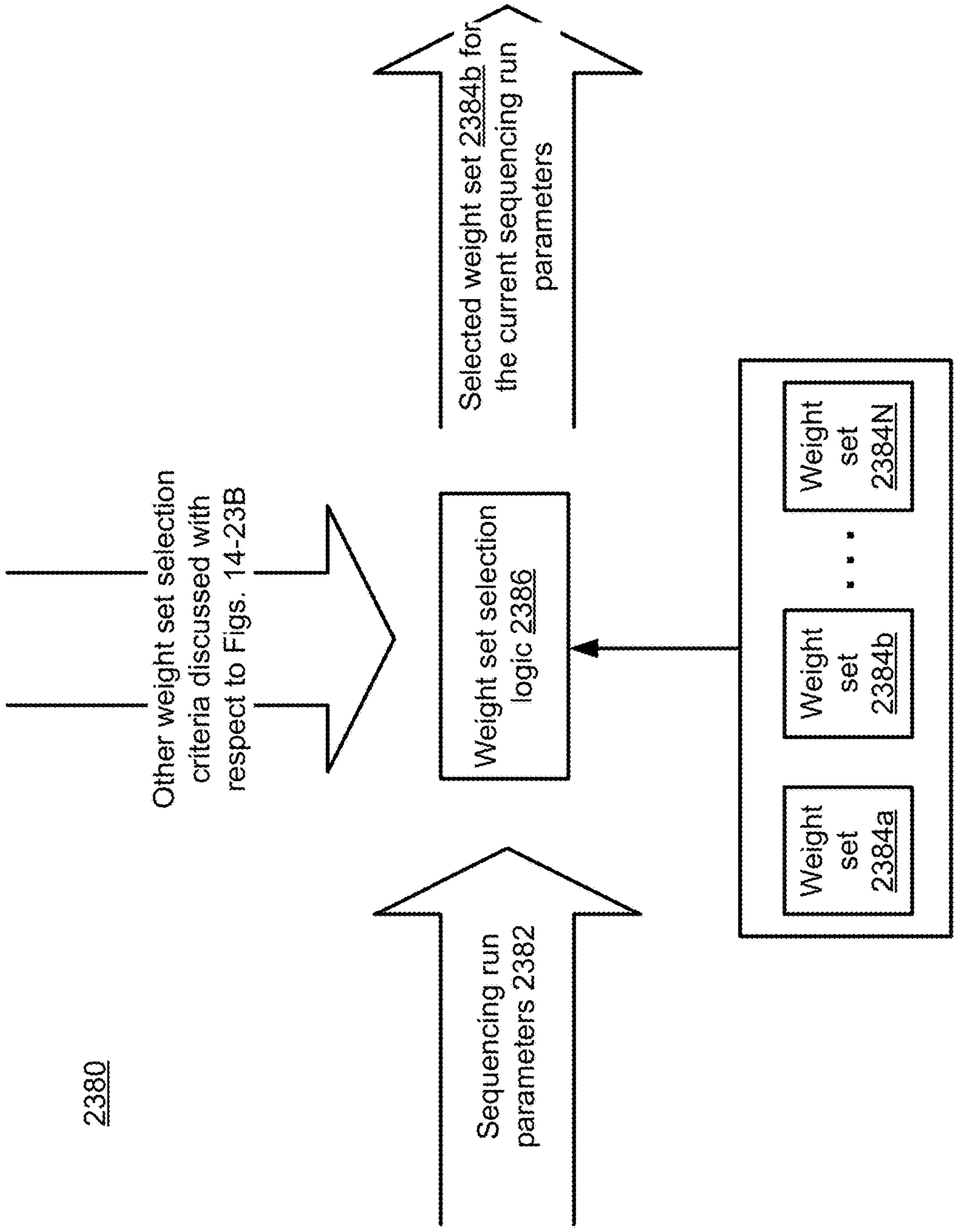
FIG. 23C illustrates a system to select weight sets based on one or more sequencing run parameters.

FIG. 23C illustrates a system 2300 to select weight sets based on one or more sequencing run parameters 2382. For example, illustrated is a weight set selection logic 2386, which may be executed on the configurable processor 450 and/or the host processor 2304. The weight set selection logic 2386 receives the one or more sequencing run parameters 2382, as well as one or more other weight set selection criteria discussed with respect to FIGS. 14-23B. The weight set selection logic 2386 selects a weight set from among a plurality of candidate weight sets 2384*a*, . . . , 2384N, based on the one or more sequencing run parameters 2382 and/or one or more other weight set selection criteria discussed with respect to FIGS. 14-23B. In the example of FIG. 23B, the weight set selection logic 2386 selects the weight set 2384*b*. The selected weight set is then loaded in the configurable processor 450, and used to configure the neural network topology for base calling, as discussed herein.

The one or more sequencing run parameters 2382 may include one or more appropriate parameters associated with the current sequencing run. For example, reaction components (such as reagents, enzymes, samples, other biomolecules, and buffer solutions) used in the sequencing run can affect the sensor data, and the weight sets can be selected based on the type, parameters, or batch of reaction components used. For example, phasing characteristics (see FIG. 17B) can be based on a reagent pack used for the sequencing run, and can vary based on a type, age, and/or batch of the reagent pack. Thus, the various candidate weight sets can be generated for various types of batches of reaction components, and the weight set selection logic 2386 can select a weight set based on the reaction components used for the current sequencing cycle.

In another example, the weight set selection logic 2386 can estimate phasing characteristics, and select a weight set based on the phasing characteristics. For example, different weight sets can be generated for different phasing characteristics. Then early in the sequencing run, a phasing parameter can be estimated and used to select a weight set. In yet another example, multiple candidate weight sets can be tried, and the weight set with the lowest error rate (or highest signal to noise ratio) can be selected for the entire sequencing run.

Figure 24:
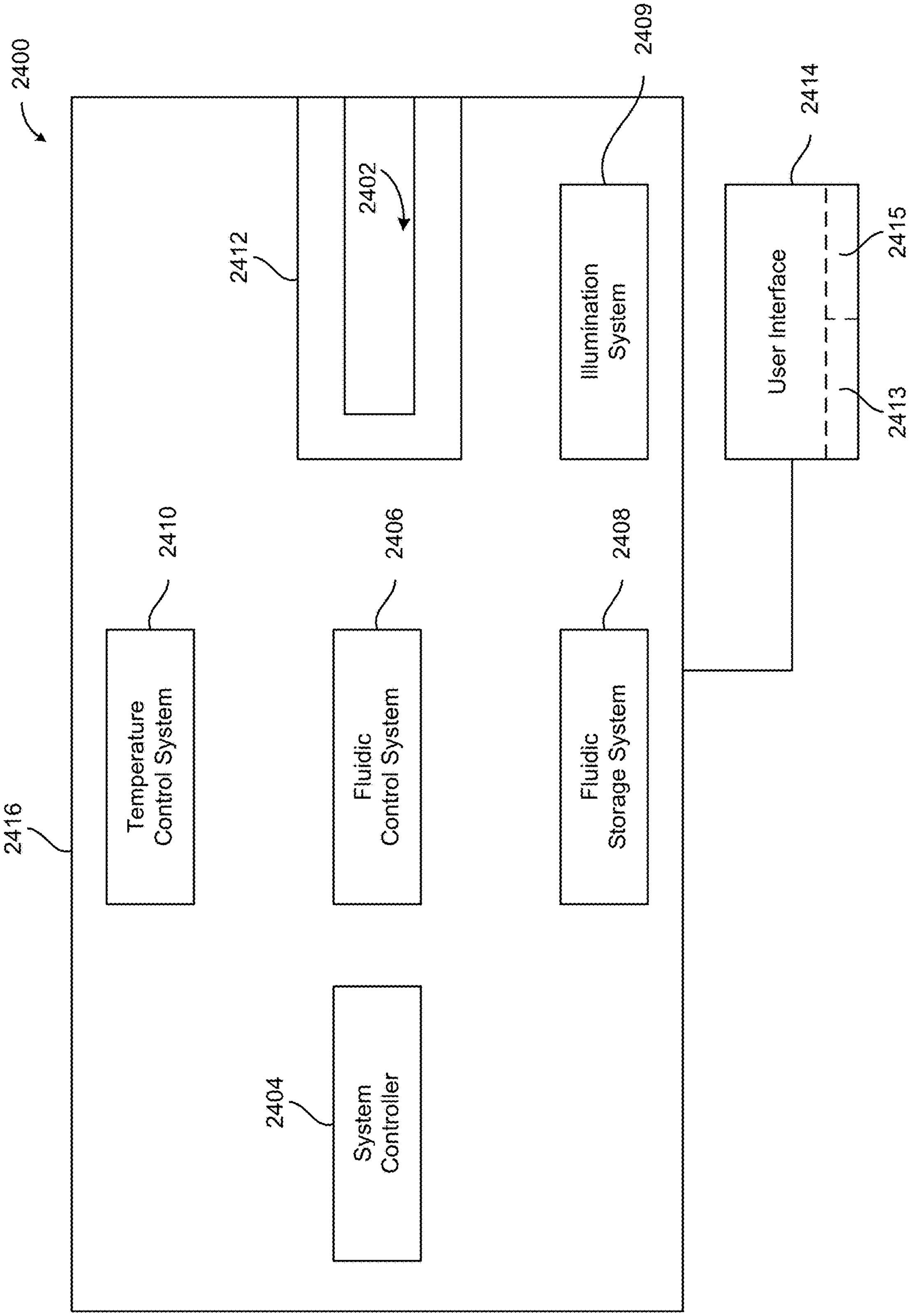
FIG. 24 is a block diagram of a base calling system in accordance with one implementation.

FIG. 24 is a block diagram of a base calling system 2400 in accordance with one implementation. The base calling system 2400 may operate to obtain any information or data that relates to at least one of a biological or chemical substance. In some implementations, the base calling system 2400 is a workstation that may be similar to a bench-top device or desktop computer. For example, a majority (or all) of the systems and components for conducting the desired reactions can be within a common housing 2416.

In particular implementations, the base calling system 2400 is a nucleic acid sequencing system (or sequencer) configured for various applications, including but not limited to de novo sequencing, resequencing of whole genomes or target genomic regions, and metagenomics. The sequencer may also be used for DNA or RNA analysis. In some implementations, the base calling system 2400 may also be configured to generate reaction sites in a biosensor. For example, the base calling system 2400 may be configured to receive a sample and generate surface attached clusters of clonally amplified nucleic acids derived from the sample. Each cluster may constitute or be part of a reaction site in the biosensor.

The exemplary base calling system 2400 may include a system receptacle or interface 2412 that is configured to interact with a biosensor 2402 to perform desired reactions within the biosensor 2402. In the following description with respect to FIG. 24, the biosensor 2402 is loaded into the system receptacle 2412. However, it is understood that a cartridge that includes the biosensor 2402 may be inserted into the system receptacle 2412 and in some states the cartridge can be removed temporarily or permanently. As described above, the cartridge may include, among other things, fluidic control and fluidic storage components.

In particular implementations, the base calling system 2400 is configured to perform a large number of parallel reactions within the biosensor 2402. The biosensor 2402 includes one or more reaction sites where desired reactions can occur. The reaction sites may be, for example, immobilized to a solid surface of the biosensor or immobilized to beads (or other movable substrates) that are located within corresponding reaction chambers of the biosensor. The reaction sites can include, for example, clusters of clonally amplified nucleic acids. The biosensor 2402 may include a solid-state imaging device (e.g., CCD or CMOS imager) and a flow cell mounted thereto. The flow cell may include one or more flow channels that receive a solution from the base calling system 2400 and direct the solution toward the reaction sites. Optionally, the biosensor 2402 can be configured to engage a thermal element for transferring thermal energy into or out of the flow channel.

The base calling system 2400 may include various components, assemblies, and systems (or sub-systems) that interact with each other to perform a predetermined method or assay protocol for biological or chemical analysis. For example, the base calling system 2400 includes a system controller 2404 that may communicate with the various components, assemblies, and sub-systems of the base calling system 2400 and also the biosensor 2402. For example, in addition to the system receptacle 2412, the base calling system 2400 may also include a fluidic control system 2406 to control the flow of fluid throughout a fluid network of the base calling system 2400 and the biosensor 2402; a fluidic storage system 2408 that is configured to hold all fluids (e.g., gas or liquids) that may be used by the bioassay system; a temperature control system 2410 that may regulate the temperature of the fluid in the fluid network, the fluidic storage system 2408, and/or the biosensor 2402; and an illumination system 2409 that is configured to illuminate the biosensor 2402. As described above, if a cartridge having the biosensor 2402 is loaded into the system receptacle 2412, the cartridge may also include fluidic control and fluidic storage components.

Also shown, the base calling system 2400 may include a user interface 2414 that interacts with the user. For example, the user interface 2414 may include a display 2413 to display or request information from a user and a user input device 2415 to receive user inputs. In some implementations, the display 2413 and the user input device 2415 are the same device. For example, the user interface 2414 may include a touch-sensitive display configured to detect the presence of an individual's touch and also identify a location of the touch on the display. However, other user input devices 2415 may be used, such as a mouse, touchpad, keyboard, keypad, handheld scanner, voice-recognition system, motion-recognition system, and the like. As will be discussed in greater detail below, the base calling system 2400 may communicate with various components, including the biosensor 2402 (e.g., in the form of a cartridge), to perform the desired reactions. The base calling system 2400 may also be configured to analyze data obtained from the biosensor to provide a user with desired information.

The system controller 2404 may include any processor-based or microprocessor-based system, including systems using microcontrollers, Reduced Instruction Set Computers (RISC), Application Specific Integrated Circuits (ASICs), Field Programmable Gate Array (FPGAs), logic circuits, and any other circuit or processor capable of executing functions described herein. The above examples are exemplary only, and are thus not intended to limit in any way the definition and/or meaning of the term system controller. In the exemplary implementation, the system controller 2404 executes a set of instructions that are stored in one or more storage elements, memories, or modules in order to at least one of obtain and analyze detection data. Detection data can include a plurality of sequences of pixel signals, such that a sequence of pixel signals from each of the millions of sensors (or pixels) can be detected over many base calling cycles. Storage elements may be in the form of information sources or physical memory elements within the base calling system 2400.

The set of instructions may include various commands that instruct the base calling system 2400 or biosensor 2402 to perform specific operations such as the methods and processes of the various implementations described herein. The set of instructions may be in the form of a software program, which may form part of a tangible, non-transitory computer readable medium or media. As used herein, the terms "software" and "firmware" are interchangeable and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the base calling system 2400, processed in response to user inputs, or processed in response to a request made by another processing machine (e.g., a remote request through a communication link). In the illustrated implementation, the system controller 2404 includes an analysis module 2538 (illustrated in FIG. 25). In other implementations, system controller 2404 does not include the analysis module 2538 and instead has access to the analysis module 2538 (e.g., the analysis module 2538 may be separately hosted on cloud).

The system controller 2404 may be connected to the biosensor 2402 and the other components of the base calling system 2400 via communication links. The system controller 2404 may also be communicatively connected to off-site systems or servers. The communication links may be hardwired, corded, or wireless. The system controller 2404 may receive user inputs or commands, from the user interface 2414 and the user input device 2415.

The fluidic control system 2406 includes a fluid network and is configured to direct and regulate the flow of one or more fluids through the fluid network. The fluid network may be in fluid communication with the biosensor 2402 and the fluidic storage system 2408. For example, select fluids may be drawn from the fluidic storage system 2408 and directed to the biosensor 2402 in a controlled manner, or the fluids may be drawn from the biosensor 2402 and directed toward, for example, a waste reservoir in the fluidic storage system 2408. Although not shown, the fluidic control system 2406 may include flow sensors that detect a flow rate or pressure of the fluids within the fluid network. The sensors may communicate with the system controller 2404.

The temperature control system 2410 is configured to regulate the temperature of fluids at different regions of the fluid network, the fluidic storage system 2408, and/or the biosensor 2402. For example, the temperature control system 2410 may include a thermocycler that interfaces with the biosensor 2402 and controls the temperature of the fluid that flows along the reaction sites in the biosensor 2402. The temperature control system 2410 may also regulate the temperature of solid elements or components of the base calling system 2400 or the biosensor 2402. Although not shown, the temperature control system 2410 may include sensors to detect the temperature of the fluid or other components. The sensors may communicate with the system controller 2404.

The fluidic storage system 2408 is in fluid communication with the biosensor 2402 and may store various reaction components or reactants that are used to conduct the desired reactions therein. The fluidic storage system 2408 may also store fluids for washing or cleaning the fluid network and biosensor 2402 and for diluting the reactants. For example, the fluid storage system 2408 may include various reservoirs to store samples, reagents, enzymes, other biomolecules, buffer solutions, aqueous, and non-polar solutions, and the like. Furthermore, the fluidic storage system 2408 may also include waste reservoirs for receiving waste products from the biosensor 2402. In implementations that include a cartridge, the cartridge may include one or more of a fluid storage system, fluidic control system or temperature control system. Accordingly, one or more of the components set forth herein as relating to those systems can be contained within a cartridge housing. For example, a cartridge can have various reservoirs to store samples, reagents, enzymes, other biomolecules, buffer solutions, aqueous, and non-polar solutions, waste, and the like. As such, one or more of a fluid storage system, fluidic control system or temperature control system can be removably engaged with a bioassay system via a cartridge or other biosensor.

The illumination system 2409 may include a light source (e.g., one or more LEDs) and a plurality of optical components to illuminate the biosensor. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In implementations that use an illumination system, the illumination system 2409 may be configured to direct an excitation light to reaction sites. As one example, fluorophores may be excited by green wavelengths of light, as such the wavelength of the excitation light may be approximately 532 nm. In one implementation, the illumination system 2409 is configured to produce illumination that is parallel to a surface normal of a surface of the biosensor 2402. In another implementation, the illumination system 2409 is configured to produce illumination that is off-angle relative to the surface normal of the surface of the biosensor 2402. In yet another implementation, the illumination system 2409 is configured to produce illumination that has plural angles, including some parallel illumination and some off-angle illumination.

The system receptacle or interface 2412 is configured to engage the biosensor 2402 in at least one of a mechanical, electrical, and fluidic manner. The system receptacle 2412 may hold the biosensor 2402 in a desired orientation to facilitate the flow of fluid through the biosensor 2402. The system receptacle 2412 may also include electrical contacts that are configured to engage the biosensor 2402 so that the base calling system 2400 may communicate with the biosensor 2402 and/or provide power to the biosensor 2402. Furthermore, the system receptacle 2412 may include fluidic ports (e.g., nozzles) that are configured to engage the biosensor 2402. In some implementations, the biosensor 2402 is removably coupled to the system receptacle 2412 in a mechanical manner, in an electrical manner, and also in a fluidic manner.

In addition, the base calling system 2400 may communicate remotely with other systems or networks or with other bioassay systems 2400. Detection data obtained by the bioassay system(s) 2400 may be stored in a remote database.

Figure 25:
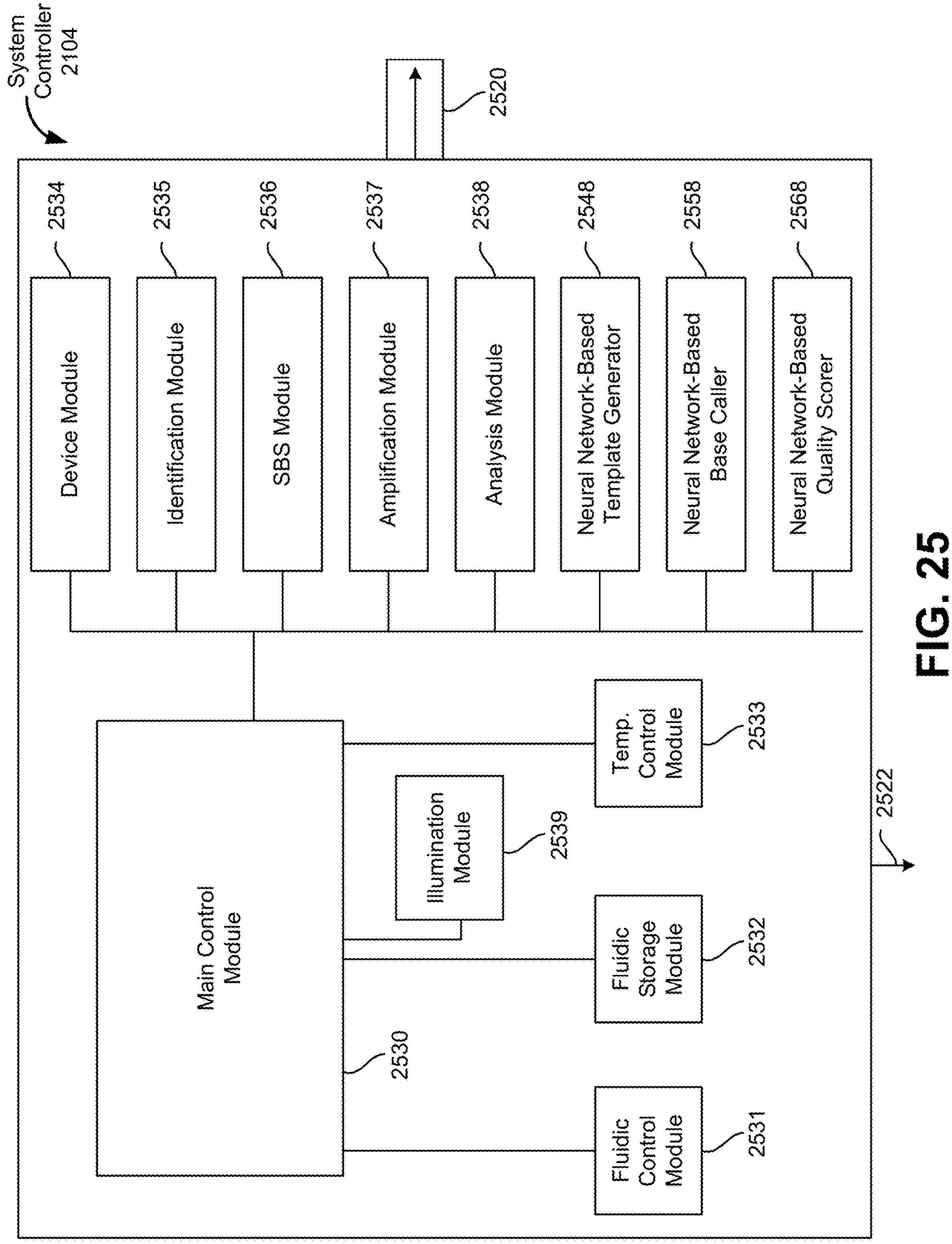
FIG. 25 is a block diagram of a system controller that can be used in the system of FIG. 24.

FIG. 25 is a block diagram of the system controller 2404 that can be used in the system of FIG. 24. In one implementation, the system controller 2404 includes one or more processors or modules that can communicate with one another. Each of the processors or modules may include an algorithm (e.g., instructions stored on a tangible and/or non-transitory computer readable storage medium) or sub-algorithms to perform particular processes. The system controller 2404 is illustrated conceptually as a collection of modules, but may be implemented utilizing any combination of dedicated hardware boards, DSPs, processors, etc. Alternatively, the system controller 2404 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication port 2520 may transmit information (e.g., commands) to or receive information (e.g., data) from the biosensor 2402 (FIG. 24) and/or the sub-systems 2406, 2408, 2410 (FIG. 24). In implementations, the communication port 2520 may output a plurality of sequences of pixel signals. A communication port 2520 may receive user input from the user interface 2414 (FIG. 24) and transmit data or information to the user interface 2414. Data from the biosensor 2402 or sub-systems 2406, 2408, 2410 may be processed by the system controller 2404 in real-time during a bioassay session. Additionally, or alternatively, data may be stored temporarily in a system memory during a bioassay session and processed in slower than real-time or off-line operation.

As shown in FIG. 25, the system controller 2404 may include a plurality of modules 2531-2539 that communicate with a main control module 2530. The main control module 2530 may communicate with the user interface 2414 (FIG. 24). Although the modules 2531-2539 are shown as communicating directly with the main control module 2530, the modules 2531-2539 may also communicate directly with each other, the user interface 2414, and the biosensor 2402. Also, the modules 2531-2539 may communicate with the main control module 2530 through the other modules.

The plurality of modules 2531-2539 include system modules 2531-2533, 2539 that communicate with the sub-systems 2406, 2408, 2410, and 2409, respectively. The fluidic control module 2531 may communicate with the fluidic control system 2406 to control the valves and flow sensors of the fluid network for controlling the flow of one or more fluids through the fluid network. The fluidic storage module 2532 may notify the user when fluids are low or when the waste reservoir is at or near capacity. The fluidic storage module 2532 may also communicate with the temperature control module 2533 so that the fluids may be stored at a desired temperature. The illumination module 2539 may communicate with the illumination system 2409 to illuminate the reaction sites at designated times during a protocol, such as after the desired reactions (e.g., binding events) have occurred. In some implementations, the illumination module 2539 may communicate with the illumination system 2409 to illuminate the reaction sites at designated angles.

The plurality of modules 2531-2539 may also include a device module 2534 that communicates with the biosensor 2402 and an identification module 2535 that determines identification information relating to the biosensor 2402. The device module 2534 may, for example, communicate with the system receptacle 2412 to confirm that the biosensor has established an electrical and fluidic connection with the base calling system 2400. The identification module 2535 may receive signals that identify the biosensor 2402. The identification module 2535 may use the identity of the biosensor 2402 to provide other information to the user. For example, the identification module 2535 may determine and then display a lot number, a date of manufacture, or a protocol that is recommended to be run with the biosensor 2402.

The plurality of modules 2531-2539 also includes an analysis module 2538 (also called signal processing module or signal processor) that receives and analyzes the signal data (e.g., image data) from the biosensor 2402. Analysis module 2538 includes memory (e.g., RAM or Flash) to store detection data. Detection data can include a plurality of sequences of pixel signals, such that a sequence of pixel signals from each of the millions of sensors (or pixels) can be detected over many base calling cycles. The signal data may be stored for subsequent analysis or may be transmitted to the user interface 2414 to display desired information to the user. In some implementations, the signal data may be processed by the solid-state imager (e.g., CMOS image sensor) before the analysis module 2538 receives the signal data.

The analysis module 2538 is configured to obtain image data from the light detectors at each of a plurality of sequencing cycles. The image data is derived from the emission signals detected by the light detectors and process the image data for each of the plurality of sequencing cycles through a neural network (e.g., a neural network-based template generator 2548, a neural network-based base caller 2558 (e.g., see FIGS. 7, 9, and 10), and/or a neural network-based quality scorer 2568) and produce a base call for at least some of the analytes at each of the plurality of sequencing cycle.

Protocol modules 2536 and 2537 communicate with the main control module 2530 to control the operation of the sub-systems 2406, 2408, and 2410 when conducting predetermined assay protocols. The protocol modules 2536 and 2537 may include sets of instructions for instructing the base calling system 2400 to perform specific operations pursuant to predetermined protocols. As shown, the protocol module may be a sequencing-by-synthesis (SBS) module 2536 that is configured to issue various commands for performing sequencing-by-synthesis processes. In SBS, extension of a nucleic acid primer along a nucleic acid template is monitored to determine the sequence of nucleotides in the template. The underlying chemical process can be polymerization (e.g., as catalyzed by a polymerase enzyme) or ligation (e.g., catalyzed by a ligase enzyme). In a particular polymerase-based SBS implementation, fluorescently labeled nucleotides are added to a primer (thereby extending the primer) in a template dependent fashion such that detection of the order and type of nucleotides added to the primer can be used to determine the sequence of the template. For example, to initiate a first SBS cycle, commands can be given to deliver one or more labeled nucleotides, DNA polymerase, etc., into/through a flow cell that houses an array of nucleic acid templates. The nucleic acid templates may be located at corresponding reaction sites. Those reaction sites where primer extension causes a labeled nucleotide to be incorporated can be detected through an imaging event. During an imaging event, the illumination system 2409 may provide an excitation light to the reaction sites. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for implementations that use reversible termination a command can be given to deliver a deblocking reagent to the flow cell (before or after detection occurs). One or more commands can be given to effect wash(es) between the various delivery steps. The cycle can then be repeated n times to extend the primer by n nucleotides, thereby detecting a sequence of length n. Exemplary sequencing techniques are described, for example, in Bentley et al., Nature 456:53-59 (2008); WO 04/018497; U.S. Pat. No. 7,057,026; WO 91/06678; WO 07/123744; U.S. Pat. Nos. 7,329,492; 7,211,414; 7,315,019; and 7,405,281, each of which is incorporated herein by reference.

For the nucleotide delivery step of an SBS cycle, either a single type of nucleotide can be delivered at a time, or multiple different nucleotide types (e.g., A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types can be distinguished based on different fluorescent labels that are attached to respective nucleotide types in the mixture. For example, four different nucleotides can be used, each having one of four different fluorophores. In one implementation, the four different fluorophores can be distinguished using excitation in four different regions of the spectrum. For example, four different excitation radiation sources can be used. Alternatively, fewer than four different excitation sources can be used, but optical filtration of the excitation radiation from a single source can be used to produce different ranges of excitation radiation at the flow cell.

In some implementations, fewer than four different colors can be detected in a mixture having four different nucleotides. For example, pairs of nucleotides can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. Exemplary apparatus and methods for distinguishing four different nucleotides using detection of fewer than four colors are described for example in U.S. Pat. App. Ser. Nos. 61/538,294 and 61/619,878, which are incorporated herein by reference in their entireties. U.S. application Ser. No. 13/624,200, which was filed on Sep. 21, 2012, is also incorporated by reference in its entirety.

The plurality of protocol modules may also include a sample-preparation (or generation) module 2537 that is configured to issue commands to the fluidic control system 2406 and the temperature control system 2410 for amplifying a product within the biosensor 2402. For example, the biosensor 2402 may be engaged to the base calling system 2400. The amplification module 2537 may issue instructions to the fluidic control system 2406 to deliver necessary amplification components to reaction chambers within the biosensor 2402. In other implementations, the reaction sites may already contain some components for amplification, such as the template DNA and/or primers. After delivering the amplification components to the reaction chambers, the amplification module 2537 may instruct the temperature control system 2410 to cycle through different temperature stages according to known amplification protocols. In some implementations, the amplification and/or nucleotide incorporation is performed isothermally.

The SBS module 2536 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing by synthesis method can be used as set forth above or as follows.

Each base calling or sequencing cycle can extend an sstDNA by a single base which can be accomplished for example by using a modified DNA polymerase and a mixture of four types of nucleotides. The different types of nucleotides can have unique fluorescent labels, and each nucleotide can further have a reversible terminator that allows only a single-base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar base calling or sequencing cycle may follow. In such a sequencing protocol, the SBS module 2536 may instruct the fluidic control system 2406 to direct a flow of reagent and enzyme solutions through the biosensor 2402. Exemplary reversible terminator-based SBS methods which can be utilized with the apparatus and methods set forth herein are described in US Patent Application Publication No. 2007/0166705 A1, US Patent Application Publication No. 2006/0188901 A1, U.S. Pat. No. 7,057,026, US Patent Application Publication No. 2006/0240439 A1, US Patent Application Publication No. 2006/02814714709 A1, PCT Publication No. WO 05/065814, PCT Publication No. WO 06/064199, each of which is incorporated herein by reference in its entirety. Exemplary reagents for reversible terminator-based SBS are described in U.S. Pat. Nos. 7,541,444; 7,057,026; 7,427,673; 7,566,537; and 7,592,435, each of which is incorporated herein by reference in its entirety.

In some implementations, the amplification and SBS modules may operate in a single assay protocol where, for example, template nucleic acid is amplified and subsequently sequenced within the same cartridge.

The base calling system 2400 may also allow the user to reconfigure an assay protocol. For example, the base calling system 2400 may offer options to the user through the user interface 2414 for modifying the determined protocol. For example, if it is determined that the biosensor 2402 is to be used for amplification, the base calling system 2400 may request a temperature for the annealing cycle. Furthermore, the base calling system 2400 may issue warnings to a user if a user has provided user inputs that are generally not acceptable for the selected assay protocol.

In implementations, the biosensor 2402 includes millions of sensors (or pixels), each of which generates a plurality of sequences of pixel signals over successive base calling cycles. The analysis module 2538 detects the plurality of sequences of pixel signals and attributes them to corresponding sensors (or pixels) in accordance to the row-wise and/or column-wise location of the sensors on an array of sensors.

Each sensor in the array of sensors can produce sensor data for a tile of the flow cell, where a tile in an area on the flow cell at which clusters of genetic material are disposed during the based calling operation. The sensor data can comprise image data in an array of pixels. For a given cycle, the sensor data can include more than one image, producing multiple features per pixel as the tile data.

Figure 26:
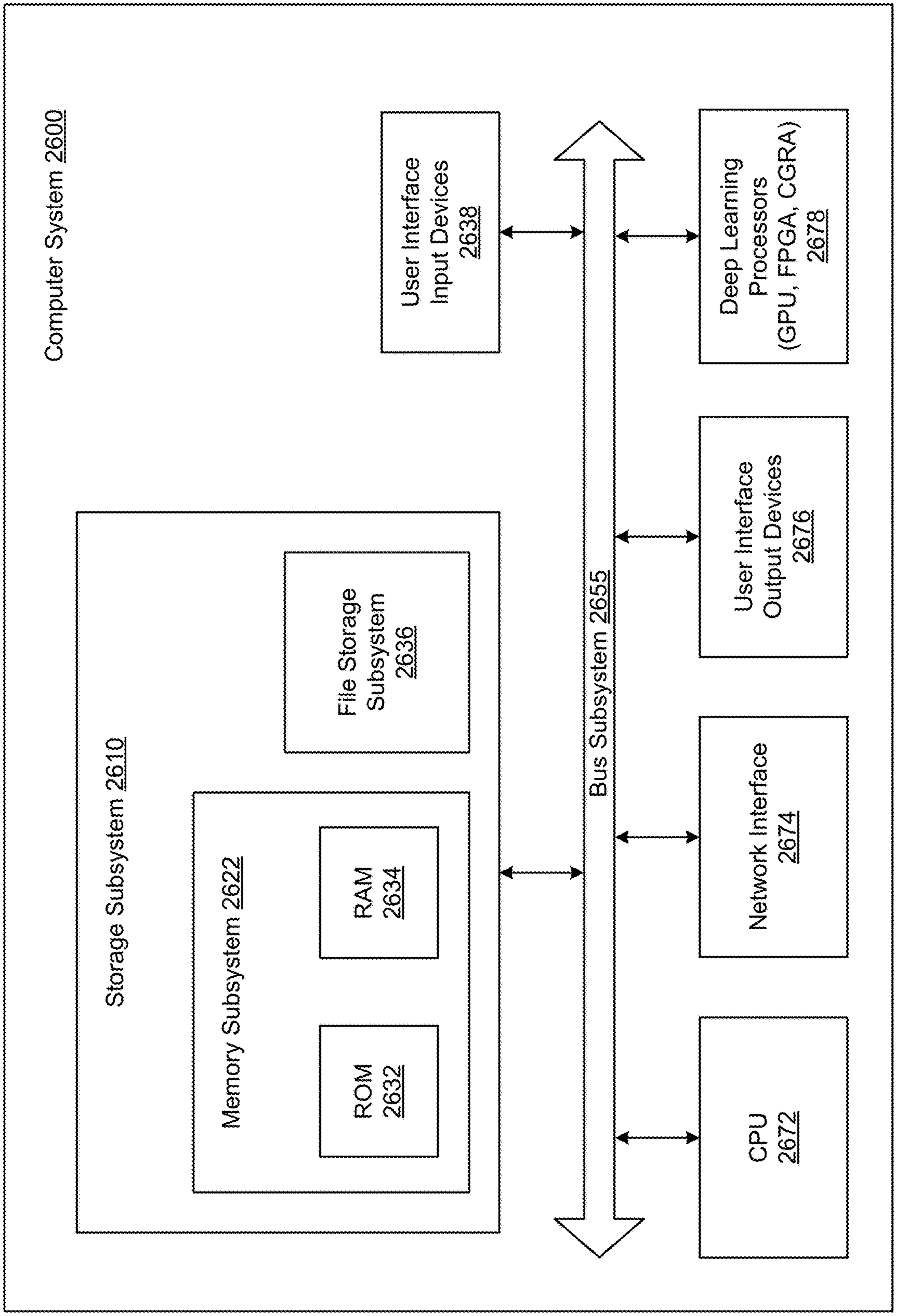
FIG. 26 is a simplified block diagram of a computer system that can be used to implement the technology disclosed.

FIG. 26 is a simplified block diagram of a computer 2600 system that can be used to implement the technology disclosed. Computer system 2600 includes at least one central processing unit (CPU) 2672 that communicates with a number of peripheral devices via bus subsystem 2655. These peripheral devices can include a storage subsystem 2610 including, for example, memory devices and a file storage subsystem 2636, user interface input devices 2638, user interface output devices 2676, and a network interface subsystem 2674. The input and output devices allow user interaction with computer system 2600. Network interface subsystem 2674 provides an interface to outside networks, including an interface to corresponding interface devices in other computer systems.

User interface input devices 2638 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 2600.

User interface output devices 2676 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 2600 to the user or to another machine or computer system.

Storage subsystem 2610 stores programming and data constructs that provide the functionality of some or all of the modules and methods described herein. These software modules are generally executed by deep learning processors 2678.

In one implementation, the neural networks are implemented using deep learning processors 2678 can be configurable and reconfigurable processors, field-programmable gate arrays (FPGAs), application-specific integrated circuits (ASICs), and/or coarse-grained reconfigurable architectures (CGRAs) and graphics processing units (GPUs) other configured devices. Deep learning processors 2678 can be hosted by a deep learning cloud platform such as Google Cloud Platform™, Xilinx™, and Cirrascale™. Examples of deep learning processors 14978 include Google's Tensor Processing Unit (TPU)™, rackmount solutions like GX4 Rackmount Series™, GX149 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, and others.

Memory subsystem 2622 used in the storage subsystem 2610 can include a number of memories including a main random access memory (RAM) 2634 for storage of instructions and data during program execution and a read only memory (ROM) 2632 in which fixed instructions are stored. A file storage subsystem 2636 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 2636 in the storage subsystem 2610, or in other machines accessible by the processor.

Bus subsystem 2655 provides a mechanism for letting the various components and subsystems of computer system 2600 communicate with each other as intended. Although bus subsystem 2655 is shown schematically as a single bus, alternative implementations of the bus subsystem can use multiple busses.

Computer system 2600 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 2600 depicted in FIG. 26 is intended only as a specific example for purposes of illustrating the preferred implementations of the present invention. Many other configurations of computer system 2600 are possible having more or less components than the computer system depicted in FIG. 26.

We claim as follows:

1. A system, comprising:

a host processor;

memory accessible by the host processor storing:

a topology of a neural network, a plurality of weight sets to configure the topology to execute a base calling operation, the plurality of weight sets comprising different weight sets trained on respective training data sets corresponding to respective sequencing events spanning i) temporal progression of the base calling operation through subseries of sensing cycles in a series of sensing cycles of the base calling operation, and/or ii) spatial progression of the base calling operation through locations on a biosensor, and sensor data for sensing cycles in the series of sensing cycles; and a configurable processor having access to the memory and configured with data flow logic to:

load the topology on processing elements of the configurable processor, select a weight set from the different weight sets based at least in part on a subject subseries of sensing cycles or a subject location on the biosensor, load, on the processing elements, subject sensor data for the subject subseries of sensing cycles and the subject location on the biosensor, load weights in the selected weight set on the processing elements to configure the topology with the weights, and cause the neural network to apply the weights in the selected weight set on the subject sensor data to produce base call classification data.

2. The system of claim 1, wherein the subseries of sensing cycles include a subseries of initial sensing cycles, a subseries of intermediate sensing cycles, and a subseries of final sensing cycles, and wherein the training data sets and the different weight sets respectively correspond to the subseries of initial sensing cycles, the subseries of intermediate sensing cycles, and the subseries of final sensing cycles.

3. The system of claim 1, wherein the locations on the biosensor include edge locations and non-edge locations, and wherein the training data sets and the different weight sets respectively correspond to the edge locations and the non-edge locations.

4. The system of claim 3, wherein the locations on the biosensor include first quadrant locations, second quadrant locations, third quadrant locations, and fourth quadrant locations, and wherein the training data sets and the different weight sets respectively correspond to the first quadrant locations, the second quadrant locations, the third quadrant locations, and the fourth quadrant locations.

5. The system of claim 4, wherein the biosensor is partitioned into a plurality of tiles, and individual ones of the edge locations, the non-edge locations, the first quadrant locations, the second quadrant locations, the third quadrant locations, and the fourth quadrant locations comprise corresponding one or more tiles of the plurality of tiles.

6. The system of claim 1, wherein the sequencing events span temporal progression of the base calling operation through base calling paired-end reads, and wherein the training data sets and the different weight sets respectively correspond to reads in the paired-end reads.

7. The system of claim 1, wherein:

the subseries of sensing cycles include a subseries of initial sensing cycles, a subseries of intermediate sensing cycles, and a subseries of final sensing cycles;

the locations on the biosensor include edge locations and non-edge locations; and the training data sets and therefore the different weight sets respectively correspond to (i) the subseries of initial sensing cycles and the edge locations, (ii) the subseries of intermediate sensing cycles and the edge locations, (iii) the subseries of final sensing cycles and the edge locations, (iv) the subseries of initial sensing cycles and the non-edge locations, (v) the subseries of intermediate sensing cycles and the non-edge locations, and (vi) the subseries of final sensing cycles and the non-edge locations.

8. The system of claim 1, wherein:

the subseries of sensing cycles include a subseries of initial sensing cycles, a subseries of intermediate sensing cycles, and a subseries of final sensing cycles;

the locations on the biosensor include first category of locations and second category of locations; and the training data sets and therefore the different weight sets respectively correspond to (i) the subseries of initial sensing cycles and the first category of locations, (ii) the subseries of intermediate sensing cycles and the first category of locations, (iii) the subseries of final sensing cycles and the first category of locations, (iv) the subseries of initial sensing cycles and the second category of locations, (v) the subseries of intermediate sensing cycles and the second category of locations, and (vi) the subseries of final sensing cycles and the second category of locations.

9. The system of claim 1, wherein the configurable processor is further configured to:

determine one or more parameters of a current sequencing run; and select the weight set from the different weight sets based further on the one or more determined parameters of the current sequencing run.

10. The system of claim 9, wherein the one or more determined parameters of the current sequencing run comprises one or more of a characteristic of reaction components used in the biosensor, or a phasing characteristic associated with the sensor data.

11. A system, comprising:

a host processor;

memory accessible by the host processor storing:

a topology of a neural network, first, second, and third weight sets for configuring the topology to execute a base calling operation, the first, second, and third weight sets respectively corresponding to first, second, and third subseries of sensing cycles in a series of sensing cycles, wherein the first, second, and third weight sets are different weight sets, and first, second, and third sensor data respectively corresponding to the first, second, and third subseries of sensing cycles; and a configurable processor having access to the memory and configured with data flow logic to:

load the topology on processing elements of the configurable processor, load the first sensor data on the processing elements, load the first weight set on the processing elements to configure the topology with weights in the first weight set, and cause the neural network to apply the weights in the first weight set on the first sensor data to produce first base call classification data for sensing cycles in the first subseries of sensing cycles, load the second sensor data on the processing elements, load the second weight set on the processing elements to configure the topology with weights in the second weight set, and cause the neural network to apply the weights in the second weight set on the second sensor data to produce second base call classification data for sensing cycles in the second subseries of sensing cycles, and load the third sensor data on the processing elements, load the third weight set on the processing elements to configure the topology with weights in the third weight set, and cause the neural network to apply the weights in the third weight set on the third sensor data to produce third base call classification data for sensing cycles in the third subseries of sensing cycles.

12. The system of claim 11, wherein the memory further stores:

fourth, fifth, and subsequent weight sets for configuring the topology to execute a base calling operation, the fourth, fifth, and subsequent weight sets respectively corresponding to fourth, fifth, and subsequent subseries of sensing cycles in the series of sensing cycles; and fourth, fifth, and subsequent sensor data for the fourth, fifth, and subsequent subseries of sensing cycles.

13. The system of claim 12, wherein the configurable processor is configured with data flow logic to:

load the fourth sensor data on the processing elements, load the fourth weight set on the processing elements to configure the topology with weights in the fourth weight set, and cause the neural network to apply the weights in the fourth weight set on the fourth sensor data to produce fourth base call classification data for sensing cycles in the fourth subseries of sensing cycles;

load the fifth sensor data on the processing elements, load the fifth weight set on the processing elements to configure the topology with weights in the fifth weight set, and cause the neural network to apply the weights in the fifth weight set on the fifth sensor data to produce fifth base call classification data for sensing cycles in the fifth subseries of sensing cycles; and load the subsequent sensor data, and the subsequent weight set on the processing elements to configure the topology with weights in the subsequent weight set, and to cause the neural network to apply the weights in the subsequent weight set on the subsequent sensor data to produce subsequent base call classification data for sensing cycles in the subsequent subseries of sensing cycles.

14. The system of claim 11, wherein the topology takes, as input, sensor data from successive sensing cycles, and the topology includes spatial layers that do not combine the sensor data and resulting feature maps between the successive sensing cycles, and temporal layers that combine resulting feature maps between the successive sensing cycles.

15. The system of claim 14, wherein the first weight set includes first spatial weights for the spatial layers and first temporal weights for the temporal layers, the second weight set includes second spatial weights for the spatial layers and second temporal weights for the temporal layers, and the third weight set includes third spatial weights for the spatial layers and third temporal weights for the temporal layers.

16. The system of claim 14, wherein the first weight set includes spatial weights for the spatial layers and first temporal weights for the temporal layers, the second weight set includes second temporal weights for the temporal layers, and the third weight set includes third temporal weights for the temporal layers, and wherein the configurable processor is configured with data flow logic to:

load the first sensor data on the processing elements, load the spatial weights and the first temporal weights on the processing elements to configure the spatial layers with the spatial weights and the temporal layers with the first temporal weights, and cause the neural network to apply the configured spatial and temporal layers on the first sensor data to produce first base call classification data for sensing cycles in the first subseries of sensing cycles;

load the second sensor data on the processing elements, load the second temporal weights on the processing elements to reconfigure the temporal layers with weights in the second temporal weights, without reconfiguring the spatial layers, and cause the neural network to apply the reconfigured temporal layers and the previously configured spatial layers on the second sensor data to produce second base call classification data for sensing cycles in the second subseries of sensing cycles; and load the third sensor data on the processing elements, load the third temporal weights on the processing elements to reconfigure the temporal layers with weights in the third temporal weights, without reconfiguring the spatial layers, and cause the neural network to apply the reconfigured temporal layers and the previously configured spatial layers on the third sensor data to produce third base call classification data for sensing cycles in the third subseries of sensing cycles.

17. The system of claim 11, wherein weights in the first, second, and third weight sets are quantized using different scaling factors.

18. The system of claim 11, wherein weights in the first, second, and third weight sets respectively correspond to first, second, and third sequencing chemistries.

19. The system of claim 11, wherein weights in the first, second, and third weight sets respectively correspond to first, second, and third sequencing assays.

20. The system of claim 11, wherein weights in the first, second, and third weight sets respectively correspond to first, second, and third sequencing configurations.

21. A computer-implemented method for generating base call classification data, comprising:

loading a topology of a neural network on processing elements of a processor, the processor to execute base call operations;

storing (i) first sensor data from clusters within first one or more tiles of a flow cell, (ii) second sensor data from clusters within second one or more tiles of the flow cell, (iii) a first weight set comprising first one or more weights, and (iv) a second weight set comprising second one or more weights different from the first one or more weights, wherein the first sensor data and the second sensor data correspond to a subset of sensing cycles in a series of sensing cycles;

configuring the topology of the neural network with the first weight set;

causing the neural network configured with the first weight set to process the first sensor data and to produce first base call classification data for the first one or more tiles and for the subset of sensing cycles;

configuring the topology of the neural network with the second weight set; and causing the neural network configured with the second weight set to process the second sensor data and to produce second base call classification data for the second one or more tiles and for the subset of sensing cycles.

22. The method of claim 21, wherein the subset of sensing cycles is a first subset of sensing cycles, and wherein the method further comprises:

storing (i) third sensor data from clusters within the first one or more tiles, (ii) fourth sensor data from clusters within the second one or more tiles, (iii) a third weight set, and (iv) a fourth weight set, wherein the third sensor data and the fourth sensor data are generated during a second subset of sensing cycles in the series of sensing cycles, the second subset of sensing cycles subsequent to the first subset of sensing cycles in the series of sensing cycles;

configuring the topology of the neural network with the third weight set, and causing the neural network configured with the third weight set to process the third sensor data and to produce third base call classification data for the first one or more tiles and for the second subset of sensing cycles; and configuring the topology of the neural network with the fourth weight set, and causing the neural network configured with the fourth weight set to process the fourth sensor data and to produce fourth base call classification data for the second one or more tiles and for the second subset of sensing cycles.

23. The method of claim 21, wherein:

the first one or more tiles are within a first area of the flow cell; and the second one or more tiles are within a second area of the flow cell.

24. The method of claim 21, wherein:

the first one or more tiles are edge tiles of the flow cell; and the second one or more tiles are non-edge tiles of the flow cell.

25. The method of claim 24, further comprising:

generating the first weight set by training the neural network on sensor data generated solely from edge tiles; and generating the second weight set by training the neural network on sensor data generated solely from non-edge tiles.

26. A system, comprising:

a host processor;

memory accessible by the host processor storing (i) a topology of a neural network, and (ii) a plurality of weight sets to configure the topology to execute a basecalling operation, wherein the plurality of weight sets comprise different weight sets based on tile locations, a series of sensing cycles, or sequencing configuration; and a configurable processor having access to the memory and configured with data flow logic to load the topology on processing elements of the configurable processor, load the plurality of weight sets on the processing elements to configure the topology with the plurality of weight sets, to cause the neural network to produce base call classification data.

27. The system of claim 26, wherein the plurality of weight sets comprises a first plurality of weights based on first tile locations, a first series of sensing cycles, or a first sequencing configuration, and wherein:

the plurality of weight sets further comprises a second plurality of weights to configure the topology to execute a basecalling operation, wherein the second plurality of weights are based on second tile locations, a second series of sensing cycles, or a second sequencing configuration; and the configurable processor is configured with data flow logic to:

load the second plurality of weights on the processing elements to configure the topology with the second plurality of weights, to cause the neural network to produce additional base call classification data.

28. The system of claim 27, wherein:

the first tile locations are on a first area within a flow cell; and the second tile locations are on a second area within the flow cell.

29. The system of claim 27, wherein:

the second series of sensing cycles occur subsequent to the first series of sensing cycles.

* * * * *